US006479271B1

(12) United States Patent
Ishii et al.

(10) Patent No.: US 6,479,271 B1
(45) Date of Patent: Nov. 12, 2002

(54) GENES ENCODING DESULFURIZATION ENZYMES

(75) Inventors: Yoshitaka Ishii, Shizuoka (JP); Jin Konishi, Shizuoka (JP); Kazuaki Hirasawa, Shizuoka (JP); Hideki Okada, Shizuoka (JP); Masanori Suzuki, Shizuoka (JP)

(73) Assignee: Petroleum Energy Center, Tokyo (JP)

( * ) Notice: Subject to any disclaimer, the term of this patent is extended or adjusted under 35 U.S.C. 154(b) by 0 days.

(21) Appl. No.: 10/119,600

(22) Filed: Apr. 10, 2002

Related U.S. Application Data

(62) Division of application No. 09/647,540, filed as application No. PCT/JP99/01756 on Apr. 2, 1999, now Pat. No. 6,420,158.

(30) Foreign Application Priority Data

Apr. 2, 1998 (JP) ............................. 10-090387
Oct. 30, 1998 (JP) ............................. 10-310545

(51) Int. Cl.$^7$ .............................. C12N 9/88; C12N 1/20; C12N 15/00; C10G 32/00; C07H 21/04
(52) U.S. Cl. .................... 435/232; 435/282; 435/252.3; 435/320.1; 536/23.2
(58) Field of Search ................................ 435/232, 282, 435/252.3, 320.1; 536/23.2

(56) References Cited

FOREIGN PATENT DOCUMENTS

JP          10036859          2/1998

OTHER PUBLICATIONS

Sequence search alignment between applicants SEQ ID NO: 1 and accession U08850.*
Denome et al. (1994) Characterization of the Desulfurization Genes from Rhodococcus sp. Strain IGTS8, Journal of Bacteriology, vol. 176, No. 21, 6707–6716.
Piddington et al. (1995) Sequence and Molecular Characterization of a DNA Region Encoding the Dibenzothiophene Desulfuization Operon of Rhodococcus sp. Strain IGTS8, vol. 61, No. 2, pp. 468–475, Applied micro (19.
Konishi et al. (1997) Thermophilic Carbon–Sulfur–Bond –Targeted Biodesulfurization, vol. 63, No. 8, pp. 3164–3169 Appl. Environ. Microbiol. (1997).

* cited by examiner

*Primary Examiner*—Tekchand Saidha
(74) *Attorney, Agent, or Firm*—Fish & Richardson P.C.

(57) ABSTRACT

This invention provides novel genes encoding enzymes which decompose difficult-to-decompose thiophene compounds. By using these genes, sulfur atoms can be released from the thiophene compounds in fossil fuel such as petroleum, and the diffusion of sulfur into the environment caused by the combustion of the fossil fuel can be prevented.

17 Claims, 7 Drawing Sheets

SEQUENCE LISTING

<160> NUMBER OF SEQ ID NOS: 21

Figure 1:
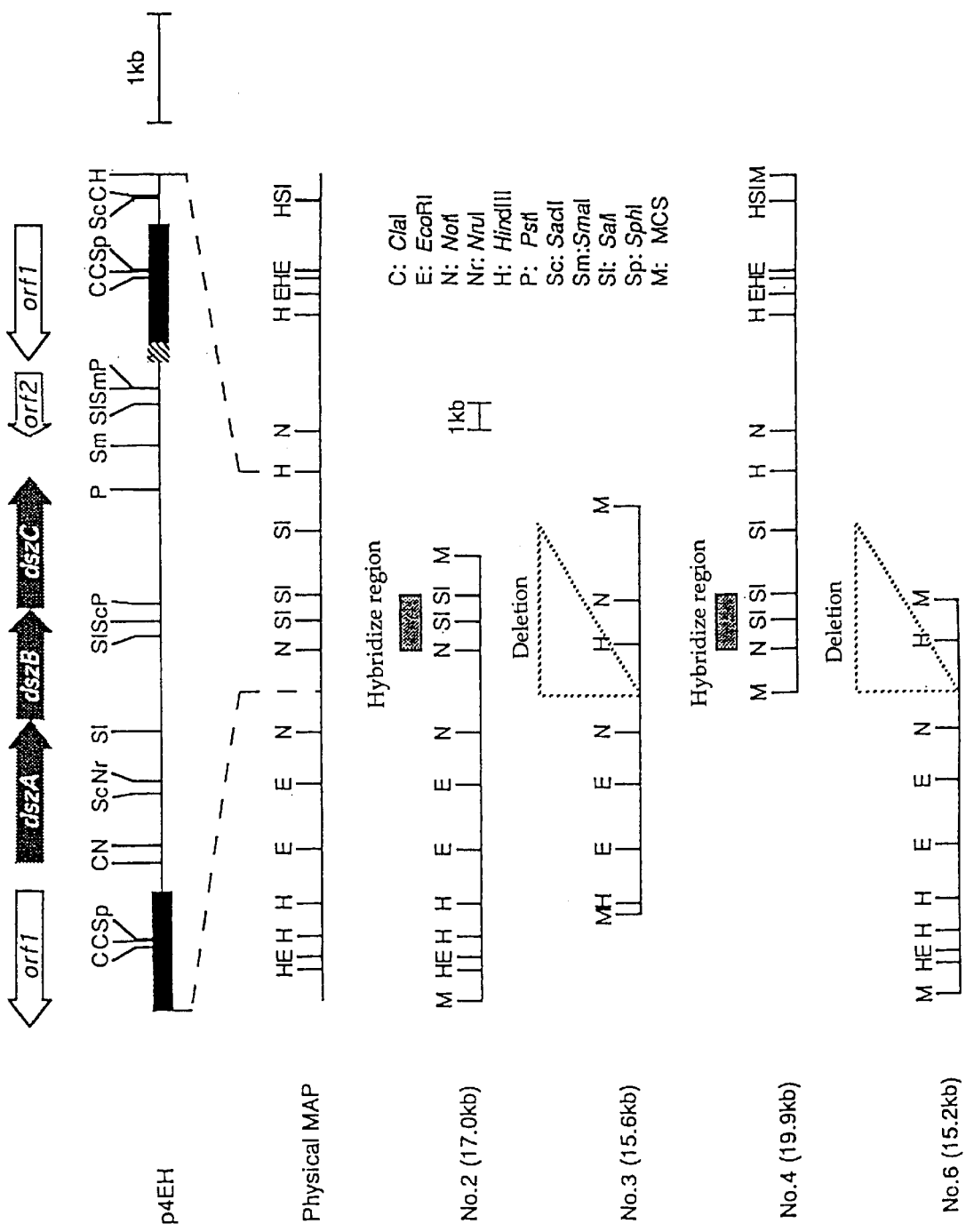
FIG. 1 shows a restriction map of insert DNA in DSZ probe positive clone.
Figure 2:
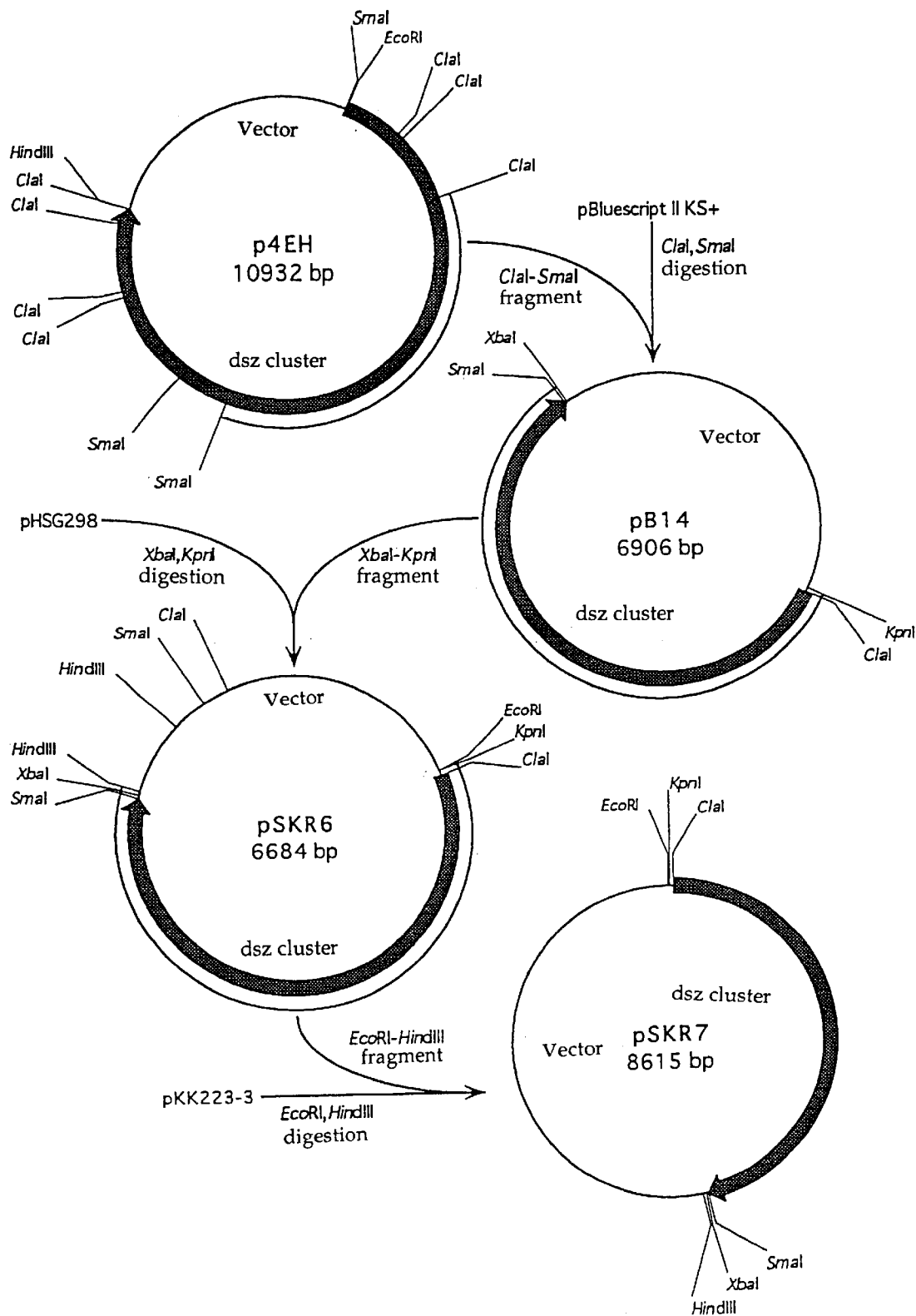
FIG. 2 shows a construction process of expression plasmid pSKR7.
Figure 3:
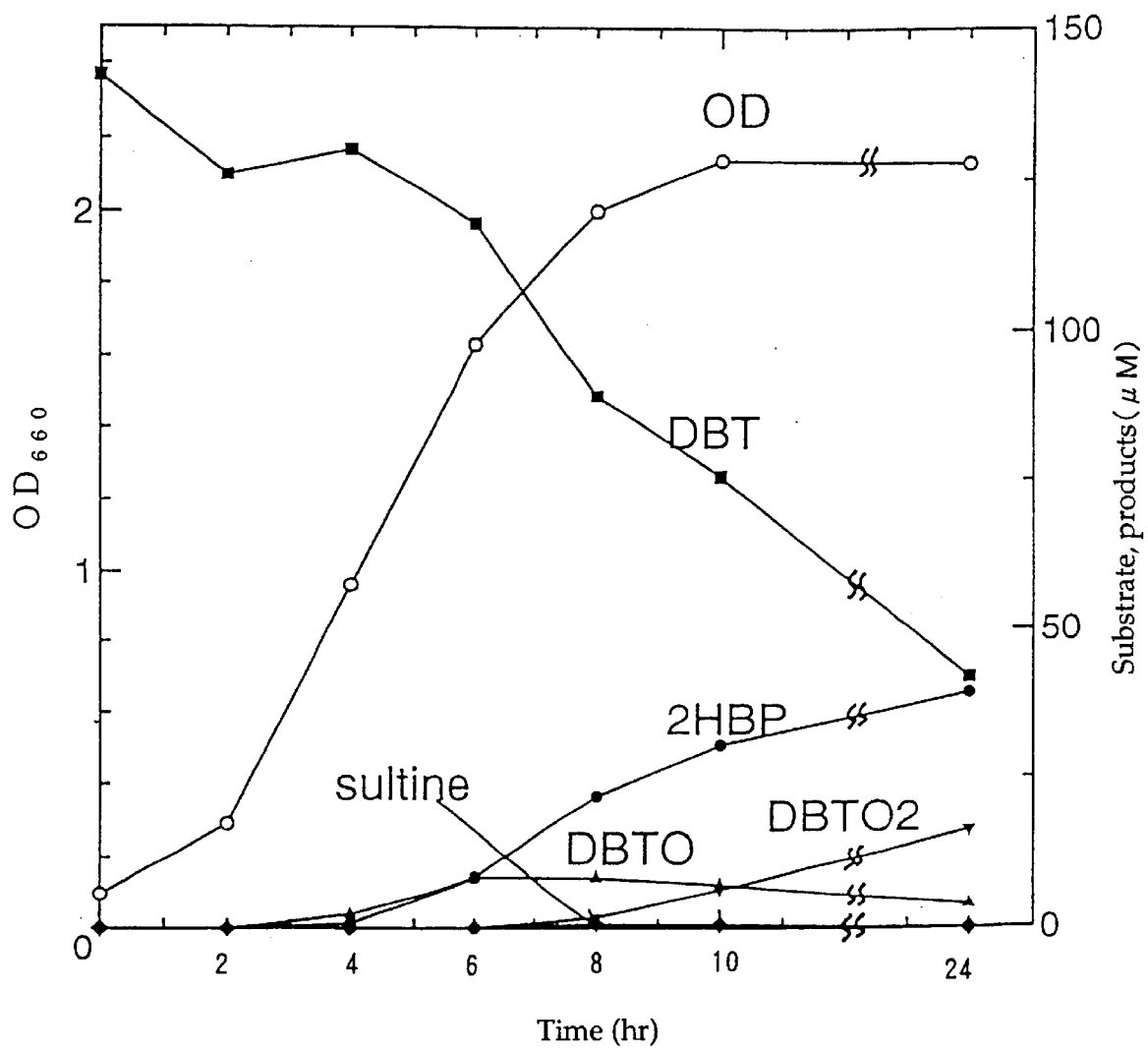
FIG. 3 shows a result of DBT decomposition by #361 strain.
Figure 4:
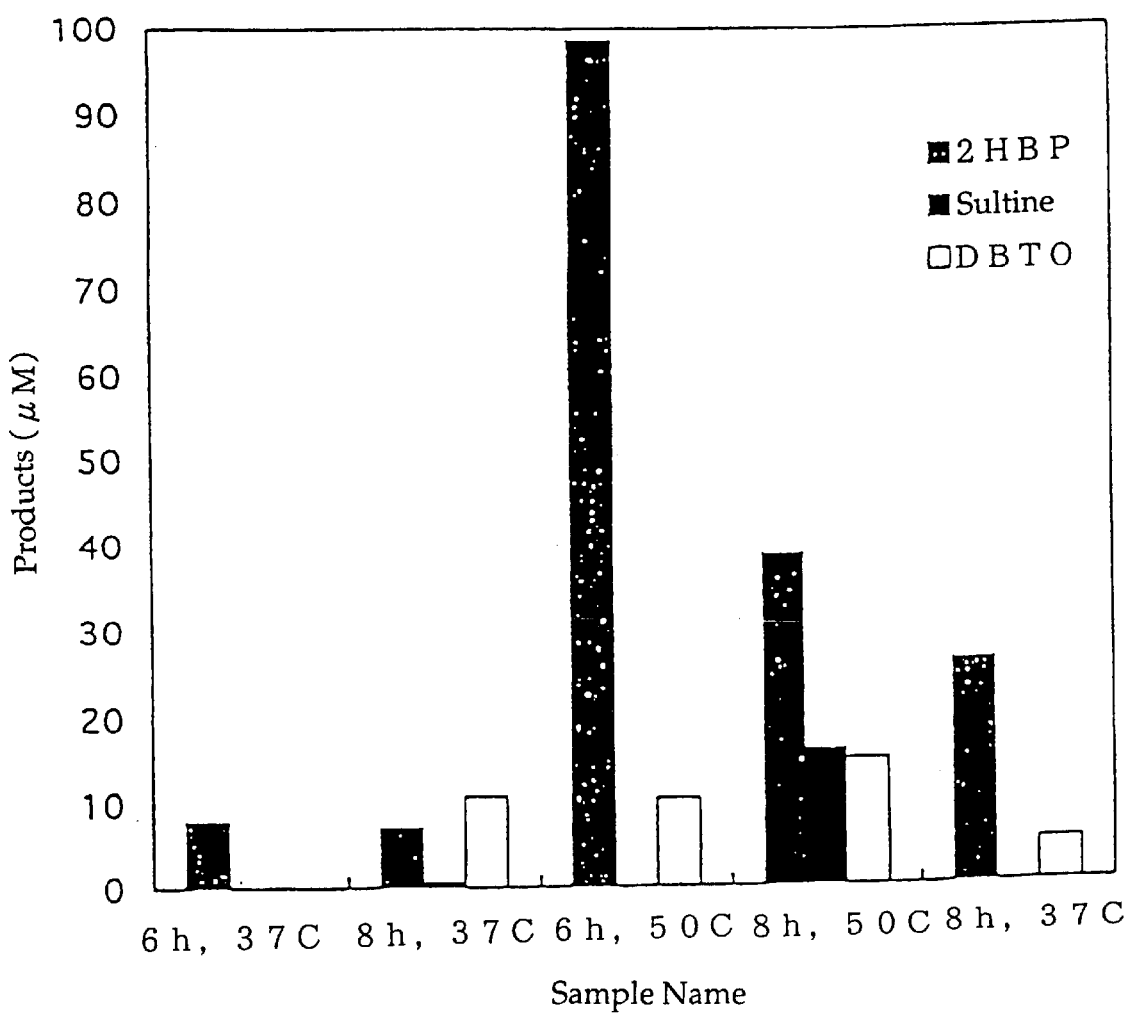
FIG. 4 shows a result of DBT decomposition reaction with cell free extracts from #361 strain.
Figure 5:
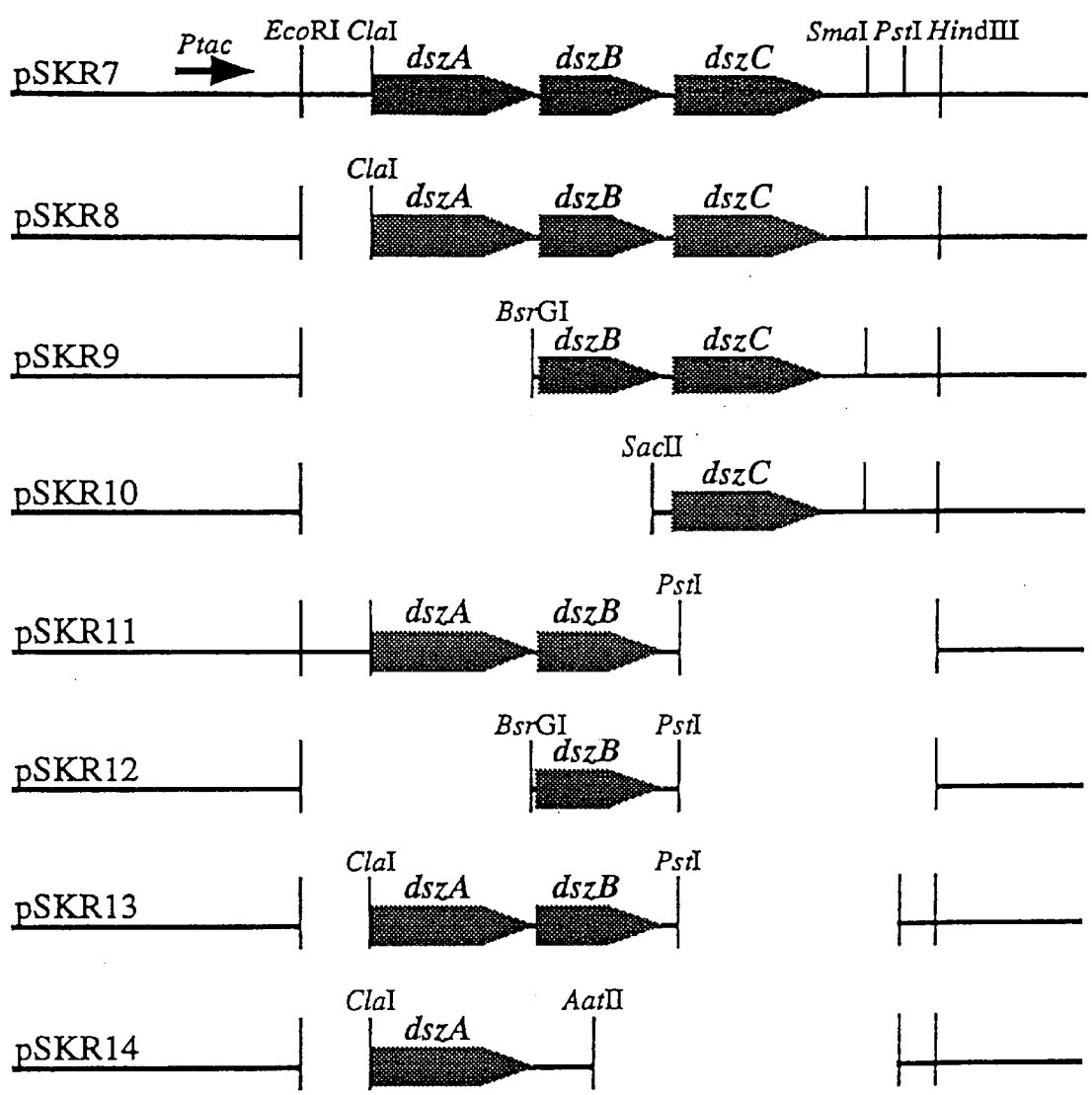
FIG. 5 shows a structure of deletion-expression plasmidd.
Figure 6:
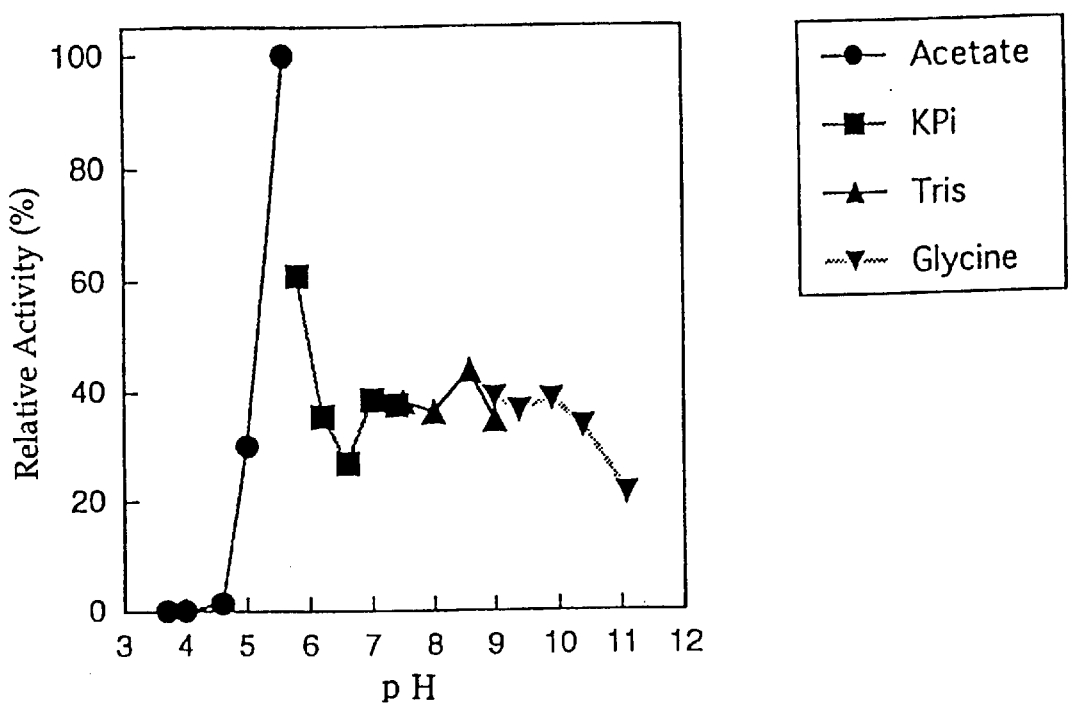
FIG. 6 shows a relation between temperature and the enzyme activity of protein A.
Figure 7:
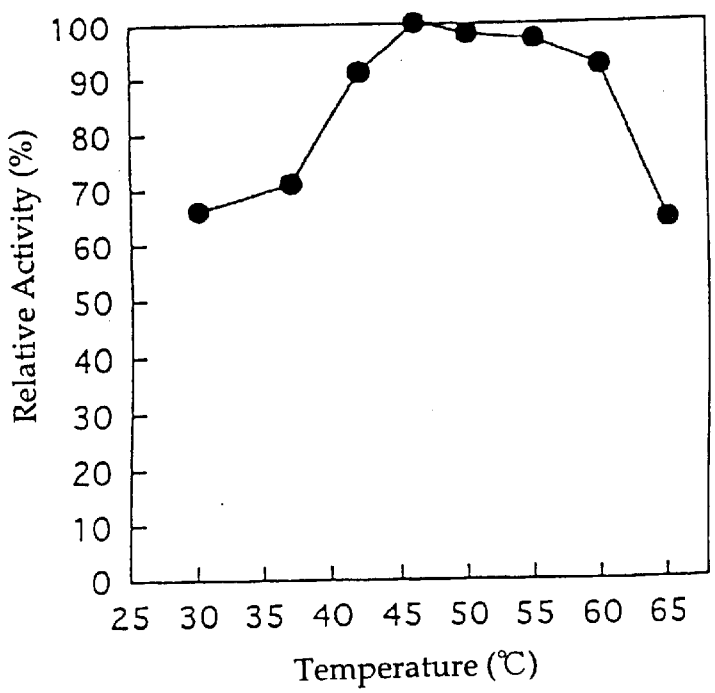
FIG. 7 shows a relation between pH and the enzyme activity of protein A.
Figure 8:
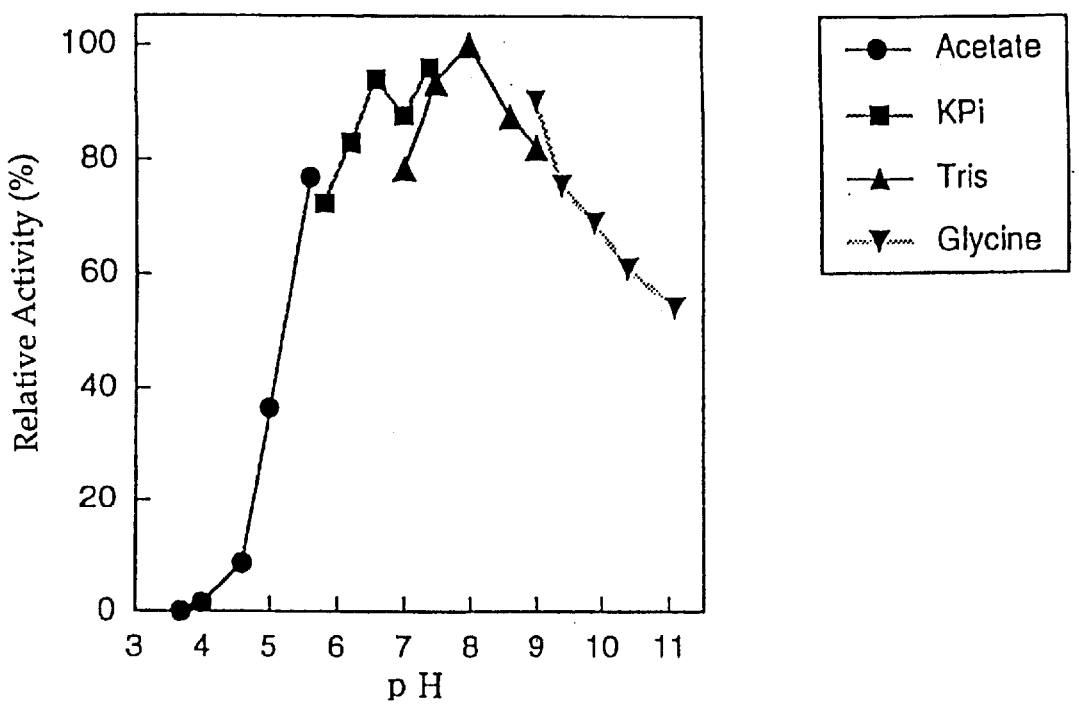
FIG. 8 shows a relation between temperature and the enzyme activity of protein B.
Figure 9:
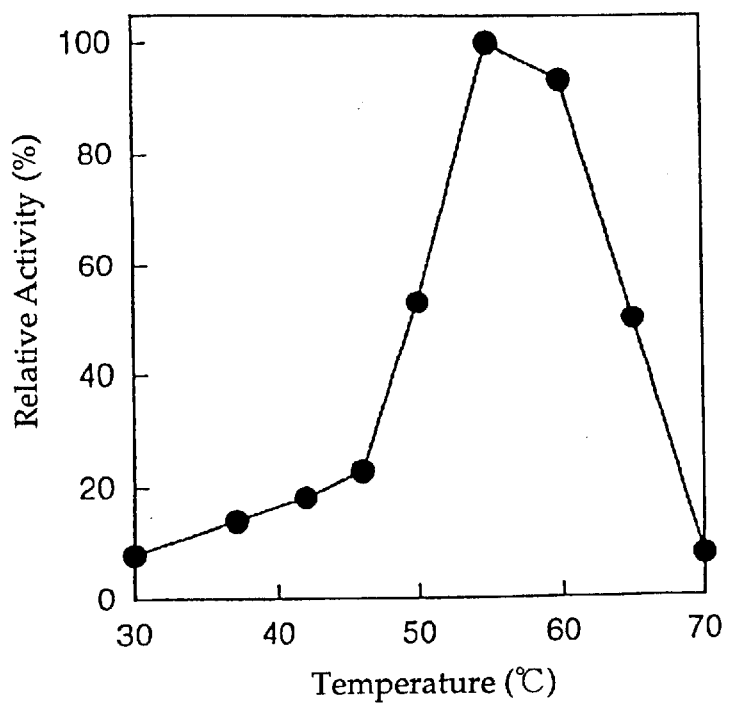
FIG. 9 shows a relation between pH and the enzyme activity of protein B.

<210> SEQ ID NO 1
<211> LENGTH: 9775
<212> TYPE: DNA
<213> ORGANISM: Paenibacillus sp.
<220> FEATURE:
<221> NAME/KEY: CDS
<222> LOCATION: (3031)...(4410)

<400> SEQUENCE: 1

```
gcggccgcgt catcttgccg ccgctcgatg cggtttatcc gatcaatgca aaggacgcaa      60
ttcctccttc gcattcctgc ggggtcgaac cgtatcagcc gcaacggatg atttccaatg     120
aaatggccgc gatgctgatt tcgaccgtcg tgaatgagct gttttcgtcg aacgccattc     180
tcgtccatta tgtcaatttt aatgcaaaga ccgggaactg caggccggtt tatgcagaag     240
atgtggccgg cgccaataac gattccgctt cggtagcagc tgcgccgtat gaccaggaag     300
ctgactccgg actgcaatca agcgagagtg gccaactcca acatgatccg acaatgctg      360 tatccccgtc tacaaaagag gaggacgctg aaatcctttc tgccgaggag cttcctgcgg     420
aacagggggg cgccgaggta gaggtcccgg aaagtggagt ggccggcgtt cgggagaatg     480
gtatcagggt aattcgcatc gaaccacttg acgagaaaca cgagaagacg caacacggat     540
acggggtacc tgtgctttat catctggaag acgggtccac gctccgtaag ttaattacgg     600
ggactcgact gagggacgct aaagcccgtg ttgaaaggct cagtcgcgat cctggcgacc     660
ggtggattga acgcaccgaa aacggactcg tgattgaaaa atcgtcgatc ggtcttgtcg     720
ggtaaggaaa attggggggcg tattttatgc cccttttct tttttttataa gggtggaaat     780 atcgcgcaag ttaaggggga gcttgagcaa atgaaggtgg ataccgcaaa aattttcaag     840
aagtttaaga aggtcattga tacccgcgac atcaatcaca tggacaagca gctttacaat     900
tatttgcatc ttcatgcagg cttcatcgcg cattatgaca tctatggctt caaagagaca     960
tattccgata aagggtttct tgatttcatt gagcattttg agcagtgcta ttatttgtgc    1020
tacggtgaat acggagagtt taaccgcgaa ctgaaggaat atgtgctgca acatgcggag    1080
cagatccgcg ctgaatttgc ttataaggcg cagcaacatg aattgaaact gctccagaag    1140
ctggcggcaa agcacggcaa aatcatttcc gacgttgcga tgaaccaaga tcaagacatg    1200
acggctgctg tggtaccgat gtcgcttgcc gcgaacgggc aattggaatt tgcgctgtga    1260
taaatgggaa gggtggagca ttccactctt cctatttatc ttttcaaatt tcggcagcat    1320
accacaattt tagagttttg gttggacaat ggctgggtaa tatgtcaagc gtctgtgaaa    1380
atgtcaggtt aactgttcta tgaaaatgtc agggatgata gttgattaaa cagccgccgt    1440
cctcttgcag actagccgga tgctgtgcta cgctgtaact gcttgctgga gaatggtttt    1500
```

-continued

```
ctccagggat ggtttgcagc gggcttgcgg ggggacgcag gcgccgcttc ttttttggcc      1560
gttgttggcg ccggggtctg tgtggcctgt gtctccacac aaggccaggc ccgcccttga      1620
tcccacagcc acacttgtcc atccatgccg acacgcactt cgacgacgct cttcgcttcc      1680
cagcgcggaa caccggggac gggctttggc atgtagcatt tcccttttcca gaagaacgtc    1740 tgcccgccgc tgatgcgccg gtattcccga cgcgtgaaga tatgctccaa aggcgtttcg      1800
ggcagcggcc ggtaggccgg ttcagcttct tgcggcgcga cggcaaactg acgattgtgc      1860
ttggcgataa gttccggtaa cacgcgattg gcttcctcca tcgtgcacac gttgcgcagc     1920
ctaagttcga tcaccaggcg atcctgaaag gtttgccaga gccgttcgat ccgtcctttg     1980
gcttggggtg acagcgcctc gatatgggta atgcccagat cggcgagggc ctgtccgaag     2040
gtggaaagcg acggcggctc accggccaat tcctgctcga gggttggctt gcccttgggc     2100
gggtgaaaaa tggagtgttg gtcgctgtag agcgcaagcg gtacgccttt gcgcctaagt     2160
ccctcgatca tgacggtcac gtagccctcc agtgtttcgg tcgggcggaa ggtggccgcg     2220
accacttccc cggtggcgtc atcgatgatg ccgtgcaggg tgagcatggg accgcgatcc     2280
tccagccagg catagggaga agcatcgatc tgccacagca tgcccgcctg aggtttgcgg     2340
ggccggggtc ggtgagcctt cggacgacgg cgcagccgcg cgggacgcaa cccgccttcc     2400
agcagaatgc ggcggaccga agagacgctt aaatggatgt tttcgtgttc ggccaacagc     2460
tcggcaaagt gggtggcatt gcttccgaag tagcgctcct gatacaggag cataacgcgt     2520
tgtttgagcg aatcggtcaa ggtgtgagcc ggcttacggc cccgattccc atgtgcgatc     2580
gcttgtgcac ctccgtgacg atatttggcc ttgagccgat acgcttgacg gacactgatg     2640
cccaggttgc gtgcaacatc ctgttccgtg agatggccgt cgatccattt ttcaatgacc     2700
ataacgcgtt tcagttcgtt ctttgtcaag gtgatctgct ccttgctcat actgacattt     2760
tctcggatca gttacaccct gacaatatca cagaacaaca acatgagtga ttgcgacggg     2820
ttgacaaaat gaatcctgaa cggtatactc cgattcataa atactaatca atttaatcgg     2880
gtttacctcg gctgactgga ccaccagagg ccctctgact ttgcggtaat tttgccggaa     2940 agcgggggc ttttctttt gcagaggagg gccgaaaaac agttttctgc tcctggatga     3000
```

```
ccattgaaga acattcacgc aggaacatac atg gga ggt gtt caa tcg atg cgt         3054
                                    Met Gly Gly Val Gln Ser Met Arg
                                      1               5 caa atg cat ctt gcc ggt ttt ttt gca gcg ggt aat gtg acc cat cac          3102
Gln Met His Leu Ala Gly Phe Phe Ala Ala Gly Asn Val Thr His His
     10                  15                  20 cac ggg gca tgg cgt cac ccg aaa act gat aat ggt ttt ttg tct att          3150
His Gly Ala Trp Arg His Pro Lys Thr Asp Asn Gly Phe Leu Ser Ile
 25                  30                  35                  40 tct tgg tat caa cac atc gcc cgt aca ctc gag cgc ggc cgc ttt gac          3198
Ser Trp Tyr Gln His Ile Ala Arg Thr Leu Glu Arg Gly Arg Phe Asp
                 45                  50                  55 ctg ctc ttt ctg cct gac ggt ttg gct att tgg gat agc tac gga aac          3246
Leu Leu Phe Leu Pro Asp Gly Leu Ala Ile Trp Asp Ser Tyr Gly Asn
             60                  65                  70 aat ctt gat gct gga ttg aga ttt gga ggc caa gga gcc gct ttt ctg          3294
Asn Leu Asp Ala Gly Leu Arg Phe Gly Gly Gln Gly Ala Ala Phe Leu
         75                  80                  85 gat ccc gtc ccc gtg ctc gcc acc atg gct gcg gcc acg gag aga ctg          3342
Asp Pro Val Pro Val Leu Ala Thr Met Ala Ala Ala Thr Glu Arg Leu
     90                  95                 100 ggc ctg ggg gcc acg att tcg aca acc tac tat cct cct tac cat gtg          3390
```

```
Gly Leu Gly Ala Thr Ile Ser Thr Thr Tyr Tyr Pro Pro Tyr His Val
105                 110                 115                 120 gca aga gtg ttt gct acg ctg gat cac tta aca aaa gga agg gca gcc    3438
Ala Arg Val Phe Ala Thr Leu Asp His Leu Thr Lys Gly Arg Ala Ala
            125                 130                 135 tgg aat gtc gtg acc tca ctc aac aac gcc gag gcc agg aac ttt ggg    3486
Trp Asn Val Val Thr Ser Leu Asn Asn Ala Glu Ala Arg Asn Phe Gly
                140                 145                 150 tat gag gaa cac ctg gat cac gat agt cgg tac gac cgt gcc gat gag    3534
Tyr Glu Glu His Leu Asp His Asp Ser Arg Tyr Asp Arg Ala Asp Glu
            155                 160                 165 ttt ctt gag att aca gat aaa ttg tgg agg agt tgg gat cag gat gca    3582
Phe Leu Glu Ile Thr Asp Lys Leu Trp Arg Ser Trp Asp Gln Asp Ala
170                 175                 180 ttg ctc ctc gac aaa aaa cag ggt ctt ttt gct gat ccc aga aag gtc    3630
Leu Leu Leu Asp Lys Lys Gln Gly Leu Phe Ala Asp Pro Arg Lys Val
185                 190                 195                 200 cac tat att gat cac tcc gga acc tgg ttc tcc gtc cgg ggc ccg tta    3678
His Tyr Ile Asp His Ser Gly Thr Trp Phe Ser Val Arg Gly Pro Leu
            205                 210                 215 caa gtc ccg cgg tcg cca cag ggt cgt cct gtc atc att cag gcg gga    3726
Gln Val Pro Arg Ser Pro Gln Gly Arg Pro Val Ile Ile Gln Ala Gly
            220                 225                 230 tcc tcc gcc cgt gga aag aca ttt gct gct cgg tgg gca gaa gcc gtt    3774
Ser Ser Ala Arg Gly Lys Thr Phe Ala Ala Arg Trp Ala Glu Ala Val
        235                 240                 245 ttc acc att gcg ccg aac cga gtc gcg atg cgg gcg ttt tac gaa gac    3822
Phe Thr Ile Ala Pro Asn Arg Val Ala Met Arg Ala Phe Tyr Glu Asp
        250                 255                 260 ttg aaa aaa cag gta atc gcc gca gga cgc cgt ccc gag aat tgc aaa    3870
Leu Lys Lys Gln Val Ile Ala Ala Gly Arg Arg Pro Glu Asn Cys Lys
265                 270                 275                 280 ata ctc cct gcc gtc att ccg att ctt ggc gat acg gag aag gaa gcg    3918
Ile Leu Pro Ala Val Ile Pro Ile Leu Gly Asp Thr Glu Lys Glu Ala
                285                 290                 295 cgc gag cgg cag gaa gaa gtg aat cag cta gtg ata cca gaa gct ggt    3966
Arg Glu Arg Gln Glu Glu Val Asn Gln Leu Val Ile Pro Glu Ala Gly
            300                 305                 310 ctc tct acc ctg tca agc cat tgc gga gtg gat ttt tcc cgc tat cct    4014
Leu Ser Thr Leu Ser Ser His Cys Gly Val Asp Phe Ser Arg Tyr Pro
            315                 320                 325 ttg gat gct cca att cgt gag gtg ctg gat gcg gtc ggt gag gtg ggt    4062
Leu Asp Ala Pro Ile Arg Glu Val Leu Asp Ala Val Gly Glu Val Gly
330                 335                 340 ggg acg aga ggt ctt tta gag atg gtg gtg aaa ctg aca gag aca gaa    4110
Gly Thr Arg Gly Leu Leu Glu Met Val Val Lys Leu Thr Glu Thr Glu
345                 350                 355                 360 aac tta acg ttg cgc gac cta ggg gtt cgc tat ggc tgg gta ctc gta    4158
Asn Leu Thr Leu Arg Asp Leu Gly Val Arg Tyr Gly Trp Val Leu Val
                365                 370                 375 ccg cag ttg gtt gga acc ccg gag cag gtg gca ggg gag ttg gaa tct    4206
Pro Gln Leu Val Gly Thr Pro Glu Gln Val Ala Gly Glu Leu Glu Ser
            380                 385                 390 ctg ttc aat gaa ccg gcg gcc gac ggc ttc gtg atc tct ccc tac tat    4254
Leu Phe Asn Glu Pro Ala Ala Asp Gly Phe Val Ile Ser Pro Tyr Tyr
            395                 400                 405 ctg ccc ggc gct tac gag gaa ttt gtc gac aaa gtg gtt cct att ttg    4302
Leu Pro Gly Ala Tyr Glu Glu Phe Val Asp Lys Val Val Pro Ile Leu
        410                 415                 420
```

```
cag gac cgg ggt ctt ttc aga cgg gag tat gaa ggg gat acc ttg cgc         4350
Gln Asp Arg Gly Leu Phe Arg Arg Glu Tyr Glu Gly Asp Thr Leu Arg
425                 430                 435                 440 cag cat ctc ggt ctg gaa gac gtt agc gaa gcc gaa gaa gct gta cag         4398
Gln His Leu Gly Leu Glu Asp Val Ser Glu Ala Glu Glu Ala Val Gln
                445                 450                 455 ggg gtg agc gaa tgagcacgct ctcagccatt ggcccgaccc gcgttgcgta             4450
Gly Val Ser Glu
            460 tagtaattgt ccggttgcaa acgctttgct cgtggcctca cggacgggga agctagagcg       4510 tcaaggtgtt cttctctcgc agatcgcctt tgcccaaggg gcgacacatt ttgcgtatga       4570 tcatgcagcc tacacccgat ttggcggcga gataccaccg ctggtgagcg aagggctgcg       4630 tgctccgggg cggacacgtt tgttgggaat cacggttctg aagcctcgcc aagggtttta      4690 tgtgcattct gccggtaaga ttgcttcacc atcggatctt agaggcgcc gcatcggcct        4750 gagccgagct gcacagagga tccttttcgg ccatctgggc gaggaatatc ggaaccttgg      4810 cccttgggag caaacgctcg tcgccctggg atcgtgggaa gttcgagcgc tcaagcatac      4870 gttggcggcc ggcggtttga gactgaatga cgtcattgtt gaagatgttg aaaacccatg      4930 ggtggatgtc ccgcgaccta aactggatga cagtagggac ttcagctccc gagagttgtt     4990 tgctacggcg gttgaatggc agagtcaaca gttgaaaagc gggcaggtag acgcctgtt       5050 ttcctggctt ccctatgctg ccgagcttga acttcaaggt gtggctaagc cggtcttttgc    5110 gttgacagga gaggagaatg cctgggcgag cgtttgacg gtcagcgcgg ctctagtgga      5170 gcgcaggccg gagatcgtcc aacgcttggt cgactccgtc gtggaggctg cgtcctgggc    5230 aaccgatcac gccaaggaga ccattgaaat ccatgccttg aaccttgggg tttccgtgaa    5290 ggccgtggag acgggatttg gcgaagggtt tcatagggac ctgcgaccgc ggctggatca    5350 ggcggctctg cgcattctgg agcagaccca gcaatttctt ttcgaccacg gctgatcga    5410 ccggttggtg gatatagagc gttgggcggc ccccgaattt ctggacaacg catctttgtg    5470 aggaggagtt tttctaatga gaacaatcca tgccaattca tctgcagtcc gtgaagatca    5530 tcgtgcttta gacgtggcga cagaactggc caagacgttt cgtgtgaccg ttcgggaaag    5590 ggagcgtgcg gggggaaccc cgaaggcgga gcgcgacgcg attcgccgta gtggcctcct   5650 tactctactt atcagtaaag agcgcggggg actcggagaa agttggccga ccgtatacga    5710 agccatcgct gagattgcca gcgccgacgc ctcccttggg cacctgtttg gttatcattt    5770 ttcaaatttt gcctatgtgg atctctttgc ttcacctgag cagaaggctc gttggtatcc    5830 acaggctgtc cgcgagcgtt ggttccttgg gaatgcatcc agcgaaaaca atgcgcacgt    5890 tctggattgg cgtgtgacgg cgaccccgtt accggacggc agttatgaga tcaacgggac    5950 caaggccttt tgcagcggct cggccgatgc ggacaggttg cttgtgtttg ccgtcaccag    6010 cagggatcca aacggagatg gcaggatcgt cgcggcactc atccctcgg atcgtgctgg    6070 ggttcaggta aatggcgatt gggacagcct gggtatgcgt caaaccgata gtgggagcgt     6130 tacattttcg ggtgtggtgg tctatcccga cgagttgctg gggacacccg gccaagtgac    6190 ggatgcgttt gcttccggtt cgaagcccag tctttggaca cccatcaccc aactgatctt    6250 tacccacctg tacctcggca ttgcccgtgg cgctcttgaa gaggccgctc actactcgag    6310 gtcccattcg agaccatta cactcgcagg ggtggagaaa gccaccgagg atccttatgt    6370 gctagcgatt tatggggaat ttgctgcaca acttcaggtc gcggaggctg gagcccgaga   6430 ggtggcgttg cgggttcagg aattgtggga gcggaatcac gtcactcctg agcagcgggg   6490
```

```
gcagttaatg gtacaagtgg ccagtgccaa aatcgtcgcc acgcgtttgg tgatcgaact   6550
gacaagccgt ctatatgaag cgatgggggc acgggctgca gcgagccgcc aattcggctt   6610
tgaccgcttt tggcgcgacg cgcgcacgca taccttacat gacccggtag cctataagat   6670
acgcgaagta ggaaactggt tcctcaatca ccggtttcca accccagct tttactcttg    6730 aaatttagtg tgaatagatt tatttgagga tgggattggg ggtaacgccg gatgagatcg   6790
acattccagt tccacaaaat gtatctccaa cagatcggcc agcaacaccc ccgtcgcatc   6850
ctcgcgcaga tggaacgtgc tgtgactctc aagcattttc gcccagtagt aaagggtccg   6910
cttctcgatg tcccaacggt tccacgtcga caacaggggg atggccggaa tcttcaaaca   6970
ccacgttgag aaaatggacc aggaccgaag cctctcggtt ccatcatacc ccgggccgga   7030
caggttcact ctagtgccgg ataaataccg aagggctgcc ccttggatgt gaggcagccc   7090
gaaaaacatt ttccctgacg ggagttttca tcggcgtttc tcttatctcc gcccgagcag   7150
ttcgtcgcgg gtattcaccc ggcggctcaa taattggtgc gggcggcgca ggcggtttgt   7210
ctccacttca tatatatatc cgttgatgat ggtgtccttc ggaatcagcg ggtggttgcg   7270
caggtattcg acttgggcca cggtcgcctc gtccacattg tcaaaggtac ggaaccattt   7330
ttcgaaagct gccggctcgc tcagtaccag ctcggggagg gagggatcca acggaacccg   7390
ttccacgtct atgttgagtt tggcccggag accgtcgaca acttcccggc cgccggcggt   7450
catcatgccg cattcggtgt gattgatcac gatgatttct ttcgtcccga agaagttcag   7510
ggtgagggcc gccgagcgga tgacgtcgtc ggtcacaacc cctccggcat gcggaacac    7570 atgggcatcc ccgggctgca gcccgagaat gtcttccacc ggaagtcgtt catccatgca   7630
ggccaggaca aacagccgca ggttattggg aatccccttc tgcctccgga gcacccattc   7690
ctcatgattt cggatcgctt cgtcaattcg ctcgctcaaa ctcatgatag ttccccctgt   7750
caagcgtctg tgaaaatgtc aggttaactg ttctatgaaa atgtcaggga tgatagttga   7810
ttaaacagcc gccgtcctct tgcagactag ccggatgctg tgctacgctg taactgcttg   7870
ctggagaatg gttttctcca gggatggttt gcagcgggct tgcgggggga cgcaggcgcc   7930
gcttcttttt tggccgttgt tggcgccggg gtctgtgtgg cctgtgtctc cacacaaggc   7990
caggcccgcc cttgatccca cagccacact tgtccatcca tgccgacacg cacttcgacg   8050
acgctcttcg cttcccagcg cggaacaccg gggacgggct ttggcatgta gcatttccct   8110
ttccagaaga acgtctgccc gccgctgatg cgccggtatt cccgacgcgt gaagatatgc   8170
tccaaaggcg tttcgggcag cggccggtag gccggttcag cttcttgcgg cgcgacggca   8230
aactgacgat tgtgcttggc gataagttcc ggtaacacgc gattggcttc ctccatcgtg   8290
cacacgttgc gcagcctaag ttcgatcacc aggcgatcct gaaaggtttg ccagagccgt   8350
tcgatccgtc ctttggcttg gggtgacagc gcctcgatat gggtaatgcc cagatcggcg   8410
agggcctgtc cgaaggtgga aagcgacggc ggctcaccgg ccaattcctg ctcgagggtt   8470
ggcttgccct tggcgggtg aaaaatggag tgttggtcgc tgtagagcgc aagcggtacg    8530
cctttgcgcc taagtccctc gatcatgacg gtcacgtagc cctccagtgt ttcggtcggg   8590
cggaaggtgg ccgcgaccac ttccccggtg gcgtcatcga tgatgccgtg cagggtgagc   8650
atgggaccgc gatcctccag ccaggcatag ggagaagcat cgatctgcca cagcatgccc   8710
gcctgaggtt tgcggggccg gggtcggtga gccttcggac gacggcgcag ccgcgcggga   8770
cgcaacccgc cttccagcag aatgcggcgg accgaagaga cgcttaaatg gatgttttcg   8830
```

-continued

```
tgttcggcca acagctcggc aaagtgggtg gcattgcttc cgaagtagcg ctcctgatac     8890
aggagcataa cgcgttgttt gagcgaatcg gtcaaggtgt gagccggctt acggccccga     8950
ttcccatgtg cgatcgcttg tgcacctccg tgacgatatt tggccttgag ccgatacgct     9010
tgacggacac tgatgcccag gttgcgtgca acatcctgtt ccgtgagatg gccgtcgatc     9070 cattttcaa tgaccataac gcgtttcagt tcgttctttg tcaaggtgat ctgctccttg      9130
ctcatactga cattttctcg gatcagttac accctgacaa tatcacagaa caacaacaac    9190
aatggctggg taatattgac gattttttt gcaaatgata cattaatagt attacaagct      9250
gttgtgattt tctttgtcgt tattaattcg acaaagaagg ggaatgtcgg tacgcttcaa     9310
ccgacgtata aataatgggc tttatttagc cgtggagaca ataggacacc taatttggtg    9370 tcttttgtg tttccgcggt tttttatgc ccaaaaaagg aggtaatcga tattggcttc       9430
aaatcgtgaa gaagtgcgga gcgcggaaca gtatgtgttg gcggagctgc cccaagaatt    9490
gctcgatatt cgctcttatg atgagtacca catcaatttt tcgggcgggg cagacagctt    9550
ggccgtagcc attttgatga aatacggcta taaagtgccg ccggagaagc ttatcgatac    9610
cgtcgacctc gagggggggc ccggtaccca gcttttgttc cctttagtga gggttaattg    9670
cgcgcttggc gtaatcatgg tcatagctgt ttcctgtgtg aaattgttat ccgctcacaa    9730
ttccacacaa catacgagcc gggagcataa agtgtaaagc ctggg                     9775
```

<210> SEQ ID NO 2
<211> LENGTH: 460
<212> TYPE: PRT
<213> ORGANISM: Paenibacillus sp.

<400> SEQUENCE: 2

```
Met Gly Gly Val Gln Ser Met Arg Gln Met His Leu Ala Gly Phe Phe
  1               5                  10                  15

Ala Ala Gly Asn Val Thr His His Gly Ala Trp Arg His Pro Lys
             20                  25                  30

Thr Asp Asn Gly Phe Leu Ser Ile Ser Trp Tyr Gln His Ile Ala Arg
         35                  40                  45

Thr Leu Glu Arg Gly Arg Phe Asp Leu Leu Phe Leu Pro Asp Gly Leu
     50                  55                  60

Ala Ile Trp Asp Ser Tyr Gly Asn Asn Leu Asp Ala Gly Leu Arg Phe
 65                  70                  75                  80

Gly Gly Gln Gly Ala Ala Phe Leu Asp Pro Val Pro Val Leu Ala Thr
                 85                  90                  95

Met Ala Ala Ala Thr Glu Arg Leu Gly Leu Gly Ala Thr Ile Ser Thr
            100                 105                 110

Thr Tyr Tyr Pro Pro Tyr His Val Ala Arg Val Phe Ala Thr Leu Asp
        115                 120                 125

His Leu Thr Lys Gly Arg Ala Ala Trp Asn Val Val Thr Ser Leu Asn
    130                 135                 140

Asn Ala Glu Ala Arg Asn Phe Gly Tyr Glu Glu His Leu Asp His Asp
145                 150                 155                 160

Ser Arg Tyr Asp Arg Ala Asp Glu Phe Leu Glu Ile Thr Asp Lys Leu
                165                 170                 175

Trp Arg Ser Trp Asp Gln Asp Ala Leu Leu Leu Asp Lys Lys Gln Gly
            180                 185                 190

Leu Phe Ala Asp Pro Arg Lys Val His Tyr Ile Asp His Ser Gly Thr
        195                 200                 205
```

-continued

| | | | | | | | | | | | |
|---|---|---|---|---|---|---|---|---|---|---|---|
|Trp|Phe|Ser|Val|Arg|Gly|Pro|Leu|Gln|Val|Pro|Arg|Ser|Pro|Gln|Gly|
| |210| | | | |215| | | | |220| | | | |

Arg Pro Val Ile Ile Gln Ala Gly Ser Ser Ala Arg Gly Lys Thr Phe
225                           230                        235                        240

Ala Ala Arg Trp Ala Glu Ala Val Phe Thr Ile Ala Pro Asn Arg Val
                        245                        250                        255

Ala Met Arg Ala Phe Tyr Glu Asp Leu Lys Lys Gln Val Ile Ala Ala
            260                        265                        270

Gly Arg Arg Pro Glu Asn Cys Lys Ile Leu Pro Ala Val Ile Pro Ile
        275                        280                        285

Leu Gly Asp Thr Glu Lys Glu Ala Arg Glu Arg Gln Glu Glu Val Asn
290                           295                        300

Gln Leu Val Ile Pro Glu Ala Gly Leu Ser Thr Leu Ser Ser His Cys
305                           310                        315                        320

Gly Val Asp Phe Ser Arg Tyr Pro Leu Asp Ala Pro Ile Arg Glu Val
                325                        330                        335

Leu Asp Ala Val Gly Glu Val Gly Gly Thr Arg Gly Leu Leu Glu Met
            340                        345                        350

Val Val Lys Leu Thr Glu Thr Glu Asn Leu Thr Leu Arg Asp Leu Gly
        355                        360                        365

Val Arg Tyr Gly Trp Val Leu Val Pro Gln Leu Val Gly Thr Pro Glu
            370                        375                        380

Gln Val Ala Gly Glu Leu Glu Ser Leu Phe Asn Glu Pro Ala Ala Asp
385                           390                        395                        400

Gly Phe Val Ile Ser Pro Tyr Tyr Leu Pro Gly Ala Tyr Glu Glu Phe
                405                        410                        415

Val Asp Lys Val Val Pro Ile Leu Gln Asp Arg Gly Leu Phe Arg Arg
            420                        425                        430

Glu Tyr Glu Gly Asp Thr Leu Arg Gln His Leu Gly Leu Glu Asp Val
        435                        440                        445

Ser Glu Ala Glu Glu Ala Val Gln Gly Val Ser Glu
        450                        455                        460

<210> SEQ ID NO 3
<211> LENGTH: 9775
<212> TYPE: DNA
<213> ORGANISM: Paenibacillus sp.
<220> FEATURE:
<221> NAME/KEY: CDS
<222> LOCATION: (4410)...(5468)

<400> SEQUENCE: 3

| | | |
|---|---|---|
|gcggccgcgt catcttgccg ccgctcgatg cggtttatcc gatcaatgca aaggacgcaa|      |60|
|ttcctccttc gcattcctgc ggggtcgaac cgtatcagcc gcaacggatg atttccaatg|      |120|
|aaatggccgc gatgctgatt tcgaccgtcg tgaatgagct gttttcgtcg aacgccattc|      |180|
|tcgtccatta tgtcaatttt aatgcaaaga ccgggaactg caggccggtt tatgcagaag|      |240|
|atgtggccgc cgccaataac gattccgctt cggtagcagc tgcgccgtat gaccaggaag|      |300|
|ctgactccgg actgcaatca agcgagagtg gccaactcca acatgatccg acaatgctg|      |360|
|tatcccgtc tacaaaagag gaggacgctg aaatcctttc tgccgaggag cttcctgcgg|      |420|
|aacaggggg cgccgaggta gaggtcccgg aaagtggagt ggccggcgtt cgggagaatg|      |480|
|gtatcaggt aattcgcatc gaaccacttg acgagaaaca cgagaagacg caacacggat|      |540|
|acggggtacc tgtgctttat catctggaag acgggtccac gctccgtaag ttaattacgg|      |600|

-continued

```
ggactcgact gagggacgct aaagcccgtg ttgaaaggct cagtcgcgat cctggcgacc      660
ggtggattga acgcaccgaa aacggactcg tgattgaaaa atcgtcgatc ggtcttgtcg      720
ggtaaggaaa attgggggcg tattttatgc ccctttttct tttttttataa gggtggaaat    780
atcgcgcaag ttaaggggga gcttgagcaa atgaaggtgg ataccgcaaa aattttcaag     840
aagtttaaga aggtcattga tacccgcgac atcaatcaca tggacaagca gctttacaat    900
tatttgcatc ttcatgcagg cttcatcgcg cattatgaca tctatggctt caaagagaca    960
tattccgata aagggtttct tgatttcatt gagcattttg agcagtgcta ttatttgtgc   1020
tacggtgaat acggagagtt taaccgcgaa ctgaaggaat atgtgctgca acatgcggag   1080
cagatccgcg ctgaatttgc ttataaggcg cagcaacatg aattgaaact gctccagaag   1140
ctggcggcaa agcacggcaa aatcattttcc gacgttgcga tgaaccaaga tcaagacatg   1200
acggctgctg tggtaccgat gtcgcttgcc gcgaacgggc aattggaatt tgcgctgtga   1260
taaatgggaa gggtggagca ttccactctt cctatttatc ttttcaaatt tcggcagcat   1320
accacaattt tagagttttg gttggacaat ggctgggtaa tatgtcaagc gtctgtgaaa   1380
atgtcaggtt aactgttcta tgaaaatgtc agggatgata gttgattaaa cagccgccgt   1440
cctcttgcag actagccgga tgctgtgcta cgctgtaact gcttgctgga gaatggtttt   1500
ctccagggat ggtttgcagc gggcttgcgg ggggacgcag gcgccgcttc tttttttggcc   1560
gttgttggcg ccggggtctg tgtggcctgt gtctccacac aaggccaggc ccgcccttga   1620
tcccacagcc acacttgtcc atccatgccg acacgcactt cgacgacgct cttcgcttcc   1680
cagcgcggaa caccggggac gggctttggc atgtagcatt tccctttcca gaagaacgtc   1740
tgcccgccgc tgatgcgccg gtattcccga cgcgtgaaga tatgctccaa aggcgtttcg   1800
ggcagcggcc ggtaggccgg ttcagcttct tgcggcgcga cggcaaactg acgattgtgc   1860
ttggcgataa gttccggtaa cacgcgattg gcttcctcca tcgtgcacac gttgcgcagc   1920
ctaagttcga tcaccaggcg atcctgaaag gtttgccaga gccgttcgat ccgtcctttg   1980
gcttggggtg acacgcctc gatatgggta atgcccagat cggcgagggc ctgtccgaag   2040
gtggaaagcg acggcggctc accggccaat tcctgctcga gggttggctt gcccttgggc   2100
gggtgaaaaa tggagtgttg gtcgctgtag agcgcaagcg gtacgccttt gcgcctaagt   2160
ccctcgatca tgacggtcac gtagccctcc agtgtttcgg tcgggcggaa ggtggccgcg   2220
accacttccc cggtggcgtc atcgatgatg ccgtgcaggg tgagcatggg accgcgatcc   2280
tccagccagg catagggaga agcatcgatc tgccacagca tgcccgcctg aggtttgcgg   2340
ggccggggtc ggtgagcctt cggacgacgg cgcagccgcg cgggacgcaa cccgccttcc   2400
agcagaatgc ggcggaccga agagacgctt aaatggatgt tttcgtgttc ggccaacagc   2460
tcggcaaagt gggtggcatt gcttccgaag tagcgctcct gatacaggag cataacgcgt   2520
tgtttgagcg aatcggtcaa ggtgtgagcc ggcttacggc cccgattccc atgtgcgatc   2580
gcttgtgcac ctccgtgacg atatttggcc ttgagccgat acgcttgacg gacactgatg   2640
cccaggttgc gtgcaacatc ctgttccgtg agatggccgt cgatccattt ttcaatgacc   2700
ataacgcgtt tcagttcgtt cttttgtcaag gtgatctgct ccttgctcat actgacattt   2760
tctcggatca gttacacct gacaatatca cagaacaaca acatgagtga ttgcgacggg   2820
ttgacaaaat gaatcctgaa cggtatactc cgattcataa atactaatca atttaatcgg   2880
gtttacctcg gctgactgga ccaccagagg ccctctgact ttgcggtaat tttgccggaa   2940
agcgggggggc tttttctttt gcagaggagg gccgaaaaac agttttctgc tcctggatga   3000
```

```
ccattgaaga acattcacgc aggaacatac atgggaggtg ttcaatcgat gcgtcaaatg    3060
catcttgccg ttttttttgc agcgggtaat gtgacccatc accacggggc atggcgtcac    3120
ccgaaaactg ataatggttt tttgtctatt tcttggtatc aacacatcgc ccgtacactc    3180
gagcgcggcc gctttgacct gctctttctg cctgacggtt tggctatttg ggatagctac    3240
ggaaacaatc ttgatgctgg attgagattt ggaggccaag gagccgcttt tctggatccc    3300
gtccccgtgc tcgccaccat ggctgcggcc acggagagac tgggcctggg ggccacgatt    3360
tcgacaacct actatcctcc ttaccatgtg caagagtgt ttgctacgct ggatcactta     3420
acaaaaggaa gggcagcctg gaatgtcgtg acctcactca acaacgccga ggccaggaac    3480
tttgggtatg aggaacacct ggatcacgat agtcggtacg accgtgccga tgagtttctt    3540
gagattacag ataaattgtg gaggagttgg gatcaggatg cattgctcct cgacaaaaaa    3600
cagggtcttt ttgctgatcc cagaaaggtc cactatattg atcactccgg aacctggttc    3660
tccgtccggg gcccgttaca agtcccgcgg tcgccacagg gtcgtcctgt catcattcag    3720
gcgggatcct ccgcccgtgg aaagacattt gctgctcggt gggcagaagc cgttttcacc    3780
attgcgccga accgagtcgc gatgcgggcg ttttacgaag acttgaaaaa acaggtaatc    3840
gccgcaggac gccgtcccga gaattgcaaa atactccctg ccgtcattcc gattcttggc    3900
gatacggaga aggaagcgcg cgagcggcag gaagaagtga atcagctagt gataccagaa    3960
gctggtctct ctaccctgtc aagccattgc ggagtggatt tttcccgcta tcctttggat    4020
gctccaattc gtgaggtgct ggatgcggtc ggtgaggtgg gtgggacgag aggtctttta    4080
gagatggtgg tgaaactgac agagacagaa aacttaacgt tgcgcgacct aggggttcgc    4140
tatggctggg tactcgtacc gcagttggtt ggaacccccgg agcaggtggc aggggagttg    4200
gaatctctgt tcaatgaacc ggcggccgac ggcttcgtga tctctcccta ctatctgccc    4260
ggcgcttacg aggaatttgt cgacaaagtg gttcctattt tgcaggaccg gggtcttttc    4320
agacgggagt atgaagggga taccttgcgc cagcatctcg gtctggaaga cgttagcgaa    4380
gccgaagaag ctgtacaggg ggtgagcga atg agc acg ctc tca gcc att ggc     4433
                                  Met Ser Thr Leu Ser Ala Ile Gly
                                    1               5
ccg acc cgc gtt gcg tat agt aat tgt ccg gtt gca aac gct ttg ctc     4481
Pro Thr Arg Val Ala Tyr Ser Asn Cys Pro Val Ala Asn Ala Leu Leu
        10                  15                  20
gtg gcc tca cgg acg ggg aag cta gag cgt caa ggt gtt ctt ctc tcg     4529
Val Ala Ser Arg Thr Gly Lys Leu Glu Arg Gln Gly Val Leu Leu Ser
 25                  30                  35                  40
cag atc gcc ttt gcc caa ggg gcg aca cat ttt gcg tat gat cat gca     4577
Gln Ile Ala Phe Ala Gln Gly Ala Thr His Phe Ala Tyr Asp His Ala
                    45                  50                  55
gcc tac acc cga ttt ggc ggc gag ata cca ccg ctg gtg agc gaa ggg     4625
Ala Tyr Thr Arg Phe Gly Gly Glu Ile Pro Pro Leu Val Ser Glu Gly
            60                  65                  70
ctg cgt gct ccg ggg cgg aca cgt ttg ttg gga atc acg gtt ctg aag     4673
Leu Arg Ala Pro Gly Arg Thr Arg Leu Leu Gly Ile Thr Val Leu Lys
        75                  80                  85
cct cgc caa ggg ttt tat gtg cat tct gcc ggt aag att gct tca cca     4721
Pro Arg Gln Gly Phe Tyr Val His Ser Ala Gly Lys Ile Ala Ser Pro
    90                  95                  100
tcg gat ctt aga ggg cgc cgc atc ggc ctg agc cga gct gca cag agg     4769
Ser Asp Leu Arg Gly Arg Arg Ile Gly Leu Ser Arg Ala Ala Gln Arg
105                 110                 115                 120
```

```
atc ctt ttc ggc cat ctg ggc gag gaa tat cgg aac ctt ggc cct tgg      4817
Ile Leu Phe Gly His Leu Gly Glu Glu Tyr Arg Asn Leu Gly Pro Trp
            125                 130                 135 gag caa acg ctc gtc gcc ctg gga tcg tgg gaa gtt cga gcg ctc aag      4865
Glu Gln Thr Leu Val Ala Leu Gly Ser Trp Glu Val Arg Ala Leu Lys
        140                 145                 150 cat acg ttg gcg gcc ggc ggt ttg aga ctg aat gac gtc att gtt gaa      4913
His Thr Leu Ala Ala Gly Gly Leu Arg Leu Asn Asp Val Ile Val Glu
        155                 160                 165 gat gtt gaa aac cca tgg gtg gat gtc ccg cga cct aaa ctg gat gac      4961
Asp Val Glu Asn Pro Trp Val Asp Val Pro Arg Pro Lys Leu Asp Asp
170                 175                 180 agt agg gac ttc agc tcc cga gag ttg ttt gct acg gcg gtt gaa tgg      5009
Ser Arg Asp Phe Ser Ser Arg Glu Leu Phe Ala Thr Ala Val Glu Trp
185                 190                 195                 200 cag agt caa cag ttg aaa agc ggg cag gta gac gcc ctg ttt tcc tgg      5057
Gln Ser Gln Gln Leu Lys Ser Gly Gln Val Asp Ala Leu Phe Ser Trp
                205                 210                 215 ctt ccc tat gct gcc gag ctt gaa ctt caa ggt gtg gct aag ccg gtc      5105
Leu Pro Tyr Ala Ala Glu Leu Glu Leu Gln Gly Val Ala Lys Pro Val
        220                 225                 230 ttt gcg ttg aca gga gag gag aat gcc tgg gcg agc gtt tgg acg gtc      5153
Phe Ala Leu Thr Gly Glu Glu Asn Ala Trp Ala Ser Val Trp Thr Val
        235                 240                 245 agc gcg gct cta gtg gag cgc agg ccg gag atc gtc caa cgc ttg gtc      5201
Ser Ala Ala Leu Val Glu Arg Arg Pro Glu Ile Val Gln Arg Leu Val
    250                 255                 260 gac tcc gtc gtg gag gct gcg tcc tgg gca acc gat cac gcc aag gag      5249
Asp Ser Val Val Glu Ala Ala Ser Trp Ala Thr Asp His Ala Lys Glu
265                 270                 275                 280 acc att gaa atc cat gcc ttg aac ctt ggg gtt tcc gtg aag gcc gtg      5297
Thr Ile Glu Ile His Ala Leu Asn Leu Gly Val Ser Val Lys Ala Val
                285                 290                 295 gag acg gga ttt ggc gaa ggg ttt cat agg gac ctg cga ccg cgg ctg      5345
Glu Thr Gly Phe Gly Glu Gly Phe His Arg Asp Leu Arg Pro Arg Leu
            300                 305                 310 gat cag gcg gct ctg cgc att ctg gag cag acc cag caa ttt ctt ttc      5393
Asp Gln Ala Ala Leu Arg Ile Leu Glu Gln Thr Gln Gln Phe Leu Phe
            315                 320                 325 gac cac ggg ctg atc gac cgg ttg gtg gat ata gag cgt tgg gcg gcc      5441
Asp His Gly Leu Ile Asp Arg Leu Val Asp Ile Glu Arg Trp Ala Ala
        330                 335                 340 ccc gaa ttt ctg gac aac gca tct ttg tgaggaggag tttttctaat            5488
Pro Glu Phe Leu Asp Asn Ala Ser Leu
345                 350 gagaacaatc catgccaatt catctgcagt ccgtgaagat catcgtgctt tagacgtggc    5548
gacagaactg gccaagacgt tcgtgtgac cgttcgggaa agggagcgtg cgggggggaac    5608 cccgaaggcg gagcgcgacg cgattcgccg tagtggcctc cttactctac ttatcagtaa    5668
agagcgcggg ggactcggag aaagttggcc gaccgtatac gaagccatcg ctgagattgc    5728
cagcgccgac gcctcccttg gcacctgtt tggttatcat ttttcaaatt ttgcctatgt     5788
ggatctcttt gcttcacctg agcagaaggc tcgttggtat ccacaggctg tccgcgagcg    5848
ttggttcctt gggaatgcat ccagcgaaaa caatgcgcac gttctggatt ggcgtgtgac    5908
ggcgaccccg ttaccggacg gcagttatga gatcaacggg accaaggcct tttgcagcgg    5968
ctcggccgat gcggacaggt tgcttgtgtt tgccgtcacc agcagggatc caaacggaga    6028
tggcaggatc gtcgcggcac tcatcccctc ggatcgtgct ggggttcagg taaatggcga    6088
```

```
ttgggacagc ctgggtatgc gtcaaaccga tagtgggagc gttacatttt cggtgtggt     6148
ggtctatccc gacgagttgc tggggacacc cggccaagtg acggatgcgt ttgcttccgg    6208
ttcgaagccc agtctttgga cacccatcac ccaactgatc tttacccacc tgtacctcgg    6268
cattgcccgt ggcgctcttg aagaggccgc tcactactcg aggtcccatt cgagaccatt    6328
tacactcgca ggggtggaga aagccaccga ggatccttat tgtgctagcga tttatgggga   6388
atttgctgca caacttcagg tcgcggaggc tggagcccga gaggtggcgt tgcgggttca    6448
ggaattgtgg gagcggaatc acgtcactcc tgagcagcgg gggcagttaa tggtacaagt    6508
ggccagtgcc aaaatcgtcg ccacgcgttt ggtgatcgaa ctgacaagcc gtctatatga    6568
agcgatgggg gcacgggctg cagcgagccg ccaattcggc tttgaccgct tttggcgcga    6628
cgcgcgcacg cataccttac atgacccggt agcctataag atacgcgaag taggaaactg    6688
gttcctcaat caccggtttc caaccccccag ctttttactct tgaaatttag tgtgaataga   6748
tttatttgag gatgggattg ggggtaacgc cggatgagat cgacattcca gttccacaaa    6808
atgtatctcc aacagatcgg ccagcaacac ccccgtcgca tcctcgcgca gatggaacgt    6868
gctgtgactc tcaagcattt tcgcccagta gtaaagggtc cgcttctcga tgtcccaacg    6928
gttccacgtc gaacaacagg ggatggccgg aatcttcaaa caccacgttg agaaaatgga    6988
ccaggaccga agcctctcgg ttccatcata ccccgggccg gacaggttca ctctagtgcc    7048
ggataaatac cgaagggctg ccccttggat gtgaggcagc ccgaaaaaca ttttccctga    7108
cgggagtttt catcggcgtt tctcttatct ccgcccgagc agttcgtcgc gggtattcac    7168
ccggcggctc aataattggt gcgggcggcg caggcggttt gtctccactt catatatata    7228
tccgttgatg atggtgtcct tcggaatcag cgggtggttg cgcaggtatt cgacttgggc    7288
cacggtcgcc tcgtccacat tgtcaaaggt acggaaccat ttttcgaaag ctgccggctc    7348
gctcagtacc agctcgggga gggagggatc caacggaacc cgttccacgt ctatgttgag    7408
tttggcccgg agaccgtcga caacttcccg gccgccggcg gtcatcatgc cgcattcggt    7468
gtgattgatc acgatgattt ctttcgtccc gaagaagttc agggtgaggg ccgccgagcg    7528
gatgacgtcg tcggtcacaa cccctccggc attgcggaac acatgggcat ccccgggctg    7588
cagcccgaga atgtcttcca ccggaagtcg ttcatccatg caggccagga caaacagccg    7648
caggttattg ggaatcccct tctgcctccg gagcacccat tcctcatgat ttcggatcgc    7708
ttcgtcaatt cgctcgctca aactcatgat agttccccct gtcaagcgtc tgtgaaaatg    7768
tcaggttaac tgttctatga aaatgtcagg gatgatagtt gattaaacag ccgccgtcct    7828
cttgcagact agccggatgc tgtgctacgc tgtaactgct tgctggagaa tggttttctc    7888
cagggatggt ttgcagcggg cttgcggggg gacgcaggcg ccgcttcttt tttggccgtt    7948
gttggcgccg ggtctgtgt ggcctgtgtc tccacacaag gccaggcccg cccttgatcc     8008
cacagccaca cttgtccatc catgccgaca cgcacttcga cgacgctctt cgcttcccag    8068
cgcggaacac cggggacggg ctttggcatg tagcatttcc ctttcagaa gaacgtctgc     8128
ccgccgctga tgcgccggta ttcccgacgc gtgaagatat gctccaaagg cgtttcgggc    8188
agcggccggt aggccggttc agcttcttgc ggcgcgacgc caaactgacg attgtgcttg    8248
gcgataagtt ccggtaacac gcgattggct tcctccatcg tgcacacgtt gcgcagccta    8308
agttcgatca ccagcgatc ctgaaaggtt tgccagagcc gttcgatccg tcctttggct      8368
tggggtgaca gcgcctcgat atgggtaatg cccagatcgg cgagggcctg tccgaaggtg    8428
```

-continued

```
gaaagcgacg gcggctcacc ggccaattcc tgctcgaggg ttggcttgcc cttgggcggg    8488
tgaaaatgg agtgttggtc gctgtagagc gcaagcggta cgcctttgcg cctaagtccc     8548
tcgatcatga cggtcacgta gccctccagt gtttcggtcg ggcggaaggt ggccgcgacc    8608
acttccccgg tggcgtcatc gatgatgccg tgcagggtga gcatgggacc gcgatcctcc    8668
agccaggcat agggagaagc atcgatctgc acagcatgc ccgcctgagg tttgcggggc     8728
cggggtcggt gagccttcgg acgacggcgc agccgcgcgg gacgcaaccc gccttccagc    8788
agaatgcggc ggaccgaaga gacgcttaaa tggatgtttt cgtgttcggc aacagctcg     8848
gcaaagtggg tggcattgct tccgaagtag cgctcctgat acaggagcat aacgcgttgt    8908
ttgagcgaat cggtcaaggt gtgagccggc ttacggcccc gattcccatg tgcgatcgct    8968
tgtgcacctc cgtgacgata tttggccttg agccgatacg cttgacggac actgatgccc    9028
aggttgcgtg caacatcctg ttccgtgaga tggccgtcga tccattttc aatgaccata     9088
acgcgtttca gttcgttctt tgtcaaggtg atctgctcct tgctcatact gacattttct    9148
cggatcagtt acaccctgac aatatcacag aacaacaaca acaatggctg gtaatattg     9208
acgattttt ttgcaaatga tacattaata gtattacaag ctgttgtgat tttctttgtc    9268
gttattaatt cgacaaagaa ggggaatgtc ggtacgcttc aaccgacgta taaataatgg    9328
gctttattta gccgtggaga caataggaca cctaatttgg tgtctttttg tgtttccgcg    9388
gttttttat gcccaaaaaa ggaggtaatc gatattggct tcaaatcgtg aagaagtgcg    9448
gagcgcggaa cagtatgtgt tggcggagct gccccaagaa ttgctcgata ttcgctctta    9508
tgatgagtac cacatcaatt tttcgggcgg ggcagacagc ttggccgtag ccattttgat    9568
gaaatacggc tataaagtgc cgccggagaa gcttatcgat accgtcgacc tcgaggggg    9628
gcccggtacc cagcttttgt tccctttagt gagggttaat tgcgcgcttg gcgtaatcat    9688
ggtcatagct gtttcctgtg tgaaattgtt atccgctcac aattccacac aacatacgag    9748
ccgggagcat aaagtgtaaa gcctggg                                        9775
```

<210> SEQ ID NO 4
<211> LENGTH: 353
<212> TYPE: PRT
<213> ORGANISM: Paenibacillus sp.

<400> SEQUENCE: 4

```
Met Ser Thr Leu Ser Ala Ile Gly Pro Thr Arg Val Ala Tyr Ser Asn
  1               5                  10                  15

Cys Pro Val Ala Asn Ala Leu Leu Val Ala Ser Arg Thr Gly Lys Leu
                 20                  25                  30

Glu Arg Gln Gly Val Leu Leu Ser Gln Ile Ala Phe Ala Gln Gly Ala
             35                  40                  45

Thr His Phe Ala Tyr Asp His Ala Ala Tyr Thr Arg Phe Gly Gly Glu
         50                  55                  60

Ile Pro Pro Leu Val Ser Glu Gly Leu Arg Ala Pro Gly Arg Thr Arg
 65                  70                  75                  80

Leu Leu Gly Ile Thr Val Leu Lys Pro Arg Gln Gly Phe Tyr Val His
                 85                  90                  95

Ser Ala Gly Lys Ile Ala Ser Pro Ser Asp Leu Arg Gly Arg Arg Ile
                100                 105                 110

Gly Leu Ser Arg Ala Ala Gln Arg Ile Leu Phe Gly His Leu Gly Glu
            115                 120                 125

Glu Tyr Arg Asn Leu Gly Pro Trp Glu Gln Thr Leu Val Ala Leu Gly
```

```
                130                 135                 140
Ser Trp Glu Val Arg Ala Leu Lys His Thr Leu Ala Ala Gly Gly Leu
145                 150                 155                 160

Arg Leu Asn Asp Val Ile Val Glu Asp Val Glu Asn Pro Trp Val Asp
                165                 170                 175

Val Pro Arg Pro Lys Leu Asp Asp Ser Arg Asp Phe Ser Ser Arg Glu
            180                 185                 190

Leu Phe Ala Thr Ala Val Glu Trp Gln Ser Gln Gln Leu Lys Ser Gly
        195                 200                 205

Gln Val Asp Ala Leu Phe Ser Trp Leu Pro Tyr Ala Ala Glu Leu Glu
210                 215                 220

Leu Gln Gly Val Ala Lys Pro Val Phe Ala Leu Thr Gly Glu Glu Asn
225                 230                 235                 240

Ala Trp Ala Ser Val Trp Thr Val Ser Ala Ala Leu Val Glu Arg Arg
                245                 250                 255

Pro Glu Ile Val Gln Arg Leu Val Asp Ser Val Val Glu Ala Ala Ser
                260                 265                 270

Trp Ala Thr Asp His Ala Lys Glu Thr Ile Glu Ile His Ala Leu Asn
            275                 280                 285

Leu Gly Val Ser Val Lys Ala Val Glu Thr Gly Phe Gly Glu Gly Phe
        290                 295                 300

His Arg Asp Leu Arg Pro Arg Leu Asp Gln Ala Ala Leu Arg Ile Leu
305                 310                 315                 320

Glu Gln Thr Gln Gln Phe Leu Phe Asp His Gly Leu Ile Asp Arg Leu
                325                 330                 335

Val Asp Ile Glu Arg Trp Ala Ala Pro Glu Phe Leu Asp Asn Ala Ser
            340                 345                 350

Leu
```

<210> SEQ ID NO 5
<211> LENGTH: 9775
<212> TYPE: DNA
<213> ORGANISM: Paenibacillus sp.
<220> FEATURE:
<221> NAME/KEY: CDS
<222> LOCATION: (5487)...(6728)

<400> SEQUENCE: 5

```
gcggccgcgt catcttgccg ccgctcgatg cggtttatcc gatcaatgca aaggacgcaa    60
ttcctccttc gcattcctgc ggggtcgaac cgtatcagcc gcaacggatg atttccaatg   120
aaatggccgc gatgctgatt tcgaccgtcg tgaatgagct gttttcgtcg aacgccattc   180
tcgtccatta tgtcaatttt aatgcaaaga ccgggaactg caggccggtt tatgcagaag   240
atgtggccgg cgccaataac gattccgctt cggtagcagc tgcgccgtat gaccaggaag   300
ctgactccgg actgcaatca agcgagagtg gccaactcca acatgatccg acaatgctg   360
tatccccgtc tacaaaagag gaggacgctg aaatcctttc tgccgaggag cttcctgcgg   420
aacaggggg cgccgaggta gaggtcccgg aaagtggagt ggccggcgtt cgggagaatg   480
gtatcagggt aattcgcatc gaaccacttg acgagaaaca cgagaagacg caacacggat   540
acggggtacc tgtgctttat catctggaag acgggtccac gctccgtaag ttaattacgg   600
ggactcgact gagggacgct aaagcccgtt tgaaaggct cagtcgcgat cctggcgacc   660
ggtggattga acgcaccgaa aacggactcg tgattgaaaa atcgtcgatc ggtcttgtcg   720
ggtaaggaaa attgggggcg tattttatgc ccctttttct tttttttataa gggtggaaat   780
```

-continued

```
atcgcgcaag ttaagggga gcttgagcaa atgaaggtgg ataccgcaaa aattttcaag      840
aagtttaaga aggtcattga tacccgcgac atcaatcaca tggacaagca gctttacaat      900
tatttgcatc ttcatgcagg cttcatcgcg cattatgaca tctatggctt caaagagaca      960
tattccgata aagggtttct tgatttcatt gagcattttg agcagtgcta ttatttgtgc     1020
tacggtgaat acggagagtt taaccgcgaa ctgaggaat atgtgctgca acatgcggag      1080
cagatccgcg ctgaatttgc ttataaggcg cagcaacatg aattgaaact gctccagaag     1140
ctggcggcaa agcacggcaa aatcatttcc gacgttgcga tgaaccaaga tcaagacatg     1200
acggctgctg tggtaccgat gtcgcttgcc gcgaacgggc aattggaatt tgcgctgtga     1260
taaatgggaa gggtggagca ttccactctt cctatttatc ttttcaaatt tcggcagcat     1320
accacaattt tagagttttg gttggacaat ggctgggtaa tatgtcaagc gtctgtgaaa     1380
atgtcaggtt aactgttcta tgaaaatgtc agggatgata gttgattaaa cagccgccgt     1440
cctcttgcag actagccgga tgctgtgcta cgctgtaact gcttgctgga gaatggtttt     1500
ctccagggat ggtttgcagc gggcttgcgg ggggacgcag gcgccgcttc tttttttggcc     1560
gttgttggcg ccggggtctg tgtggcctgt gtctccacac aaggccaggc ccgcccttga     1620
tcccacagcc acacttgtcc atccatgccg acacgcactt cgacgacgct cttcgcttcc     1680
cagcgcggaa caccggggac gggctttggc atgtagcatt tccctttcca gaagaacgtc     1740
tgcccgccgc tgatgcgccg gtattcccga cgcgtgaaga tatgctccaa aggcgtttcg     1800
ggcagcggcc ggtaggccgg ttcagcttct tgcggcgcga cggcaaactg acgattgtgc     1860
ttggcgataa gttccggtaa cacgcgattg gcttcctcca tcgtgcacac gttgcgcagc     1920
ctaagttcga tcaccaggcg atcctgaaag gtttgccaga gccgttcgat ccgtcctttg     1980
gcttggggtg acagcgcctc gatatgggta atgcccagat cggcgagggc ctgtccgaag     2040
gtggaaagcg acggcggctc accggccaat tcctgctcga gggttggctt gcccttgggc     2100
gggtgaaaaa tggagtgttg gtcgctgtag agcgcaagcg gtacgccttt gcgcctaagt     2160
ccctcgatca tgacggtcac gtagccctcc agtgtttcgg tcgggcggaa ggtggccgcg     2220
accacttccc cggtggcgtc atcgatgatg ccgtgcaggg tgagcatggg accgcgatcc     2280
tccagccagg cataggagaa agcatcgatc tgccacagca tgcccgcctg aggtttgcgg     2340
ggccggggtc ggtgagcctt cggacgacgg cgcagccgcg cgggacgcaa cccgcctttcc     2400
agcagaatgc ggcggaccga agagacgctt aaatggatgt tttcgtgttc ggccaacagc     2460
tcggcaaagt gggtggcatt gcttccgaag tagcgctcct gatacaggag cataacgcgt     2520
tgtttgagcg aatcggtcaa ggtgtgagcc ggcttacggc cccgattccc atgtgcgatc     2580
gcttgtgcac ctccgtgacg atatttggcc ttgagccgat acgcttgacg gacactgatg     2640
cccaggttgc gtgcaacatc ctgttccgtg agatggccgt cgatccattt ttcaatgacc     2700
ataacgcgtt tcagttcgtt ctttgtcaag gtgatctgct ccttgctcat actgacattt     2760
tctcggatca gttacaccct gacaatatca cagaacaaca acatgagtga ttgcgacggg     2820
ttgacaaaat gaatcctgaa cggtatactc cgattcataa atactaatca atttaatcgg     2880
gtttacctcg gctgactgga ccaccagagg ccctctgact ttgcggtaat tttgccggaa     2940
agcgggggc ttttcttttt gcagaggagg gccgaaaaac agttttctgc tcctggatga     3000
ccattgaaga acattcacgc aggaacatac atgggaggtg ttcaatcgat gcgtcaaatg     3060
catcttgccg ttttttttgc agcgggtaat gtgacccatc accacggggc atggcgtcac     3120
```

-continued

```
ccgaaaactg ataatggttt tttgtctatt tcttggtatc aacacatcgc ccgtacactc    3180
gagcgcggcc gctttgacct gctctttctg cctgacggtt tggctatttg ggatagctac    3240
ggaaacaatc ttgatgctgg attgagattt ggaggccaag gagccgcttt tctggatccc    3300
gtccccgtgc tcgccaccat ggctgcggcc acggagagac tgggcctggg ggccacgatt    3360
tcgacaacct actatcctcc ttaccatgtg gcaagagtgt ttgctacgct ggatcactta    3420
acaaaaggaa gggcagcctg aatgtcgtg acctcactca acaacgccga ggccaggaac     3480
tttgggtatg aggaacacct ggatcacgat agtcggtacg accgtgccga tgagtttctt    3540
gagattacag ataaattgtg gaggagttgg gatcaggatg cattgctcct cgacaaaaaa    3600
cagggtcttt ttgctgatcc cagaaaggtc cactatattg atcactccgg aacctggttc    3660
tccgtccggg gcccgttaca agtcccgcgg tcgccacagg gtcgtcctgt catcattcag    3720
gcgggatcct ccgcccgtgg aaagacattt gctgctcggt gggcagaagc cgttttcacc    3780
attgcgccga accgagtcgc gatgcgggcg ttttacgaag acttgaaaaa acaggtaatc    3840
gccgcaggac gccgtcccga gaattgcaaa atactccctg ccgtcattcc gattcttggc    3900
gatacggaga aggaagcgcg cgagcggcag gaagaagtga atcagctagt gataccagaa    3960
gctggtctct ctaccctgtc aagccattgc ggagtggatt tttcccgcta tccttttggat   4020
gctccaattc gtgaggtgct ggatgcgtc ggtgaggtgg gtgggacgag aggtcttttta   4080
gagatggtgg tgaaactgac agagacagaa aacttaacgt tgcgcgacct agggggttcgc    4140
tatggctggg tactcgtacc gcagttggtt ggaaccccgg agcaggtggc aggggagttg    4200
gaatctctgt tcaatgaacc ggcggccgac ggcttcgtga tctctcccta ctatctgccc     4260
ggcgcttacg aggaatttgt cgacaaagtg gttcctattt gcaggaccg gggtcttttc    4320
agacgggagt atgaagggga taccttgcgc cagcatctcg gtctggaaga cgttagcgaa    4380
gccgaagaag ctgtacaggg ggtgagcgaa tgagcacgct ctcagccatt ggcccgaccc    4440
gcgttgcgta tagtaattgt ccggttgcaa acgctttgct cgtggcctca cggacgggga    4500
agctagagcg tcaaggtgtt cttctctcgc agatcgcctt tgcccaaggg gcgacacatt    4560
ttgcgtatga tcatgcagcc tacacccgat ttggcggcga gataccaccg ctggtgagcg    4620
aagggctgcg tgctccgggg cggacacgtt tgttgggaat cacggttctg aagcctcgcc    4680
aagggttttta tgtgcattct gccggtaaga ttgcttcacc atcggatctt agagggcgcc    4740
gcatcggcct gagccgagct gcacagagga tccttttcgg ccatctgggc gaggaatatc    4800
ggaaccttgg cccttgggag caaacgctcg tcgccctggg atcgtgggaa gttcgagcgc    4860
tcaagcatac gttggcggcc ggcggtttga gactgaatga cgtcattgtt gaagatgttg    4920
aaaacccatg ggtggatgtc ccgcgaccta aactggatga cagtagggac ttcagctccc    4980
gagagttgtt tgctacggcg gttgaatggc agagtcaaca gttgaaaagc gggcaggtag    5040
acgccctgtt ttcctggctt ccctatgctg ccgagcttga acttcaaggt gtggctaagc    5100
cggtctttgc gttgacagga gaggagaatg cctgggcgag cgtttggacg gtcagcgcgg    5160
ctctagtgga gcgcaggccg gagatcgtcc aacgcttggt cgactccgtc gtggaggctg    5220
cgtcctgggc aaccgatcac gccaaggaga ccattgaaat ccatgccttg aaccttgggg    5280
tttccgtgaa ggccgtggag acgggatttg gcgaagggtt tcatagggac ctgcgaccgc    5340
ggctggatca gcggctctg cgcattctgg agcagaccca gcaatttctt ttcgaccacg    5400
ggctgatcga ccggttggtg gatatagagc gttggcggcg cccgaatttt ctggacaacg    5460
catctttgtg aggaggagtt tttcta atg aga aca atc cat gcc aat tca tct    5513
```

-continued

```
                    Met Arg Thr Ile His Ala Asn Ser Ser
                      1               5
gca gtc cgt gaa gat cat cgt gct tta gac gtg gcg aca gaa ctg gcc    5561
Ala Val Arg Glu Asp His Arg Ala Leu Asp Val Ala Thr Glu Leu Ala
 10              15                  20                  25 aag acg ttt cgt gtg acc gtt cgg gaa agg gag cgt gcg ggg gga acc    5609
Lys Thr Phe Arg Val Thr Val Arg Glu Arg Glu Arg Ala Gly Gly Thr
             30                  35                  40 ccg aag gcg gag cgc gac gcg att cgc cgt agt ggc ctc ctt act cta    5657
Pro Lys Ala Glu Arg Asp Ala Ile Arg Arg Ser Gly Leu Leu Thr Leu
                 45                  50                  55 ctt atc agt aaa gag cgc ggg gga ctc gga gaa agt tgg ccg acc gta    5705
Leu Ile Ser Lys Glu Arg Gly Gly Leu Gly Glu Ser Trp Pro Thr Val
         60                  65                  70 tac gaa gcc atc gct gag att gcc agc gcc gac gcc tcc ctt ggg cac    5753
Tyr Glu Ala Ile Ala Glu Ile Ala Ser Ala Asp Ala Ser Leu Gly His
     75                  80                  85 ctg ttt ggt tat cat ttt tca aat ttt gcc tat gtg gat ctc ttt gct    5801
Leu Phe Gly Tyr His Phe Ser Asn Phe Ala Tyr Val Asp Leu Phe Ala
 90                  95                 100                 105 tca cct gag cag aag gct cgt tgg tat cca cag gct gtc cgc gag cgt    5849
Ser Pro Glu Gln Lys Ala Arg Trp Tyr Pro Gln Ala Val Arg Glu Arg
                110                 115                 120 tgg ttc ctt ggg aat gca tcc agc gaa aac aat gcg cac gtt ctg gat    5897
Trp Phe Leu Gly Asn Ala Ser Ser Glu Asn Asn Ala His Val Leu Asp
            125                 130                 135 tgg cgt gtg acg gcg acc ccg tta ccg gac ggc agt tat gag atc aac    5945
Trp Arg Val Thr Ala Thr Pro Leu Pro Asp Gly Ser Tyr Glu Ile Asn
        140                 145                 150 ggg acc aag gcc ttt tgc agc ggc tcg gcc gat gcg gac agg ttg ctt    5993
Gly Thr Lys Ala Phe Cys Ser Gly Ser Ala Asp Ala Asp Arg Leu Leu
    155                 160                 165 gtg ttt gcc gtc acc agc agg gat cca aac gga gat ggc agg atc gtc    6041
Val Phe Ala Val Thr Ser Arg Asp Pro Asn Gly Asp Gly Arg Ile Val
170                 175                 180                 185 gcg gca ctc atc ccc tcg gat cgt gct ggg gtt cag gta aat ggc gat    6089
Ala Ala Leu Ile Pro Ser Asp Arg Ala Gly Val Gln Val Asn Gly Asp
                190                 195                 200 tgg gac agc ctg ggt atg cgt caa acc gat agt ggg agc gtt aca ttt    6137
Trp Asp Ser Leu Gly Met Arg Gln Thr Asp Ser Gly Ser Val Thr Phe
            205                 210                 215 tcg ggt gtg gtg gtc tat ccc gac gag ttg ctg ggg aca ccc ggc caa    6185
Ser Gly Val Val Val Tyr Pro Asp Glu Leu Leu Gly Thr Pro Gly Gln
        220                 225                 230 gtg acg gat gcg ttt gct tcc ggt tcg aag ccc agt ctt tgg aca ccc    6233
Val Thr Asp Ala Phe Ala Ser Gly Ser Lys Pro Ser Leu Trp Thr Pro
    235                 240                 245 atc acc caa ctg atc ttt acc cac ctg tac ctc ggc att gcc cgt ggc    6281
Ile Thr Gln Leu Ile Phe Thr His Leu Tyr Leu Gly Ile Ala Arg Gly
250                 255                 260                 265 gct ctt gaa gag gcc gct cac tac tcg agg tcc cat tcg aga cca ttt    6329
Ala Leu Glu Glu Ala Ala His Tyr Ser Arg Ser His Ser Arg Pro Phe
                270                 275                 280 aca ctc gca ggg gtg gag aaa gcc acc gag gat cct tat gtg cta gcg    6377
Thr Leu Ala Gly Val Glu Lys Ala Thr Glu Asp Pro Tyr Val Leu Ala
            285                 290                 295 att tat ggg gaa ttt gct gca caa ctt cag gtc gcg gag gct gga gcc    6425
Ile Tyr Gly Glu Phe Ala Ala Gln Leu Gln Val Ala Glu Ala Gly Ala
        300                 305                 310
```

-continued

| | | |
|---|---|---|
| cga gag gtg gcg ttg cgg gtt cag gaa ttg tgg gag cgg aat cac gtc<br>Arg Glu Val Ala Leu Arg Val Gln Glu Leu Trp Glu Arg Asn His Val<br>315                    320                    325 | | 6473 |
| act cct gag cag cgg ggg cag tta atg gta caa gtg gcc agt gcc aaa<br>Thr Pro Glu Gln Arg Gly Gln Leu Met Val Gln Val Ala Ser Ala Lys<br>330                    335                    340                    345 | | 6521 |
| atc gtc gcc acg cgt ttg gtg atc gaa ctg aca agc cgt cta tat gaa<br>Ile Val Ala Thr Arg Leu Val Ile Glu Leu Thr Ser Arg Leu Tyr Glu<br>                    350                    355                    360 | | 6569 |
| gcg atg ggg gca cgg gct gca gcg agc cgc caa ttc ggc ttt gac cgc<br>Ala Met Gly Ala Arg Ala Ala Ala Ser Arg Gln Phe Gly Phe Asp Arg<br>              365                    370                    375 | | 6617 |
| ttt tgg cgc gac gcg cgc acg cat acc tta cat gac ccg gta gcc tat<br>Phe Trp Arg Asp Ala Arg Thr His Thr Leu His Asp Pro Val Ala Tyr<br>380                    385                    390 | | 6665 |
| aag ata cgc gaa gta gga aac tgg ttc ctc aat cac cgg ttt cca acc<br>Lys Ile Arg Glu Val Gly Asn Trp Phe Leu Asn His Arg Phe Pro Thr<br>              395                    400                    405 | | 6713 |
| ccc agc ttt tac tct tgaaatttag tgtgaataga tttatttgag gatgggattg<br>Pro Ser Phe Tyr Ser<br>410 | | 6768 |
| ggggtaacgc cggatgagat cgacattcca gttccacaaa atgtatctcc aacagatcgg | | 6828 |
| ccagcaacac ccccgtcgca tcctcgcgca gatggaacgt gctgtgactc tcaagcattt | | 6888 |
| tcgcccagta gtaaagggtc cgcttctcga tgtcccaacg gttccacgtc gaacaacagg | | 6948 |
| ggatggccgg aatcttcaaa caccacgttg agaaaatgga ccaggaccga agcctctcgg | | 7008 |
| ttccatcata ccccgggccg gacaggttca ctctagtgcc ggataaatac cgaagggctg | | 7068 |
| cccccttggat gtgaggcagc ccgaaaaaca ttttccctga cgggagtttt catcggcgtt | | 7128 |
| tctcttatct ccgcccgagc agttcgtcgc gggtattcac ccggcggctc aataattggt | | 7188 |
| gcgggcggcg caggcggttt gtctccactt catatatata tccgttgatg atggtgtcct | | 7248 |
| tcggaatcag cgggtggttg cgcaggtatt cgacttgggc cacggtcgcc tcgtccacat | | 7308 |
| tgtcaaaggt acgaaccat ttttcgaaag ctgccggctc gctcagtacc agctcgggga | | 7368 |
| gggagggatc caacggaacc cgttccacgt ctatgttgag tttggcccgg agaccgtcga | | 7428 |
| caacttcccg gccgccggcg gtcatcatgc cgcattcggt gtgattgatc acgatgattt | | 7488 |
| ctttcgtccc gaagaagttc agggtgaggg ccgccgagcg gatgacgtcg tcggtcacaa | | 7548 |
| cccctccggc attgcggaac acatgggcat ccccgggctg cagcccgaga atgtcttcca | | 7608 |
| ccggaagtcg ttcatccatg caggccagga caaacagccg caggttattg ggaatcccct | | 7668 |
| tctgcctccg gagcacccat tcctcatgat ttccggatcgc ttcgtcaatt cgctcgctca | | 7728 |
| aactcatgat agttcccct gtcaagcgtc tgtgaaaatg tcaggttaac tgttctatga | | 7788 |
| aaatgtcagg gatgatagtt gattaaacag ccgccgtcct cttgcagact agccggatgc | | 7848 |
| tgtgctacgc tgtaactgct tgctggagaa tggttttctc cagggatggt ttgcagcggg | | 7908 |
| cttgcggggg gacgcaggcg ccgcttcttt tttggccgtt gttggcgccg ggtctgtgt | | 7968 |
| ggcctgtgtc tccacacaag gccaggcccg cccttgatcc cacagccaca cttgtccatc | | 8028 |
| catgccgaca cgcacttcga cgacgctctt cgcttcccag cgcggaacac cggggacggg | | 8088 |
| cttttggcatg tagcatttcc ctttccagaa gaacgtctgc ccgccgctga tgcgccggta | | 8148 |
| ttcccgacgc gtgaagatat gctccaaagg cgtttcgggc agcggccggt aggccggttc | | 8208 |
| agcttcttgc ggcgcgacgg caaactgacg attgtgcttg cgataagtt ccggtaacac | | 8268 |
| gcgattggct tcctccatcg tgcacacgtt gcgcagccta agttcgatca ccaggcgatc | | 8328 |

-continued

```
ctgaaaggtt tgccagagcc gttcgatccg tcctttggct tggggtgaca gcgcctcgat    8388
atgggtaatg cccagatcgg cgagggcctg tccgaaggtg gaaagcgacg gcggctcacc    8448
ggccaattcc tgctcgaggg ttggcttgcc cttgggcggg tgaaaatgg agtgttggtc    8508 gctgtagagc gcaagcggta cgcctttgcg cctaagtccc tcgatcatga cggtcacgta    8568
gccctccagt gtttcggtcg ggcggaaggt ggccgcgacc acttccccgg tggcgtcatc    8628
gatgatgccg tgcagggtga gcatgggacc gcgatcctcc agccaggcat agggagaagc    8688
atcgatctgc cacagcatgc ccgcctgagg tttgcggggc cggggtcggt gagccttcgg    8748
acgacggcgc agccgcgcgg gacgcaaccc gccttccagc agaatgcggc ggaccgaaga    8808
gacgcttaaa tggatgtttt cgtgttcggc aacagctcg gcaaagtggg tggcattgct    8868
tccgaagtag cgctcctgat acaggagcat aacgcgttgt tgagcgaat cggtcaaggt    8928 gtgagccggc ttacgccccc gattcccatg tgcgatcgct tgtgcacctc cgtgacgata    8988
tttggccttg agccgatacg cttgacggac actgatgccc aggttgcgtg caacatcctg    9048
ttccgtgaga tggccgtcga tccattttc aatgaccata acgcgtttca gttcgttctt    9108
tgtcaaggtg atctgctcct tgctcatact gacatttct cggatcagtt acaccctgac    9168
aatatcacag aacaacaaca acaatggctg gtaatattg acgatttttt ttgcaaatga    9228
tacattaata gtattacaag ctgttgtgat tttctttgtc gttattaatt cgacaaagaa    9288
ggggaatgtc ggtacgcttc aaccgacgta taaataatgg gctttattta gccgtggaga    9348
caataggaca cctaatttgg tgtcttttg tgtttccgcg gttttttat gcccaaaaaa    9408 ggaggtaatc gatattggct tcaaatcgtg aagaagtgcg gagcgcggaa cagtatgtgt    9468 tgcggagct gccccaagaa ttgctcgata ttcgctctta tgatgagtac cacatcaatt    9528
tttcgggcgg ggcagacagc ttggccgtag ccatttgat gaaatacggc tataaagtgc    9588
cgccggagaa gcttatcgat accgtcgacc tcaggggggg gcccggtacc cagcttttgt    9648 tcccttagt gagggttaat tgcgcgcttg gcgtaatcat ggtcatagct gtttcctgtg    9708
tgaaattgtt atccgctcac aattccacac aacatacgag ccgggagcat aaagtgtaaa    9768
gcctggg                                                            9775
```

<210> SEQ ID NO 6
<211> LENGTH: 414
<212> TYPE: PRT
<213> ORGANISM: Paenibacillus sp.

<400> SEQUENCE: 6

```
Met Arg Thr Ile His Ala Asn Ser Ser Ala Val Arg Glu Asp His Arg
  1               5                  10                  15

Ala Leu Asp Val Ala Thr Glu Leu Ala Lys Thr Phe Arg Val Thr Val
                 20                  25                  30

Arg Glu Arg Glu Arg Ala Gly Gly Thr Pro Lys Ala Glu Arg Asp Ala
             35                  40                  45

Ile Arg Arg Ser Gly Leu Leu Thr Leu Leu Ile Ser Lys Glu Arg Gly
         50                  55                  60

Gly Leu Gly Glu Ser Trp Pro Thr Val Tyr Glu Ala Ile Ala Glu Ile
     65                  70                  75                  80

Ala Ser Ala Asp Ala Ser Leu Gly His Leu Phe Gly Tyr His Phe Ser
                 85                  90                  95

Asn Phe Ala Tyr Val Asp Leu Phe Ala Ser Pro Glu Gln Lys Ala Arg
                100                 105                 110
```

```
Trp Tyr Pro Gln Ala Val Arg Glu Arg Trp Phe Leu Gly Asn Ala Ser
        115                 120                 125

Ser Glu Asn Asn Ala His Val Leu Asp Trp Arg Val Thr Ala Thr Pro
    130                 135                 140

Leu Pro Asp Gly Ser Tyr Glu Ile Asn Gly Thr Lys Ala Phe Cys Ser
145                 150                 155                 160

Gly Ser Ala Asp Ala Asp Arg Leu Leu Val Phe Ala Val Thr Ser Arg
                165                 170                 175

Asp Pro Asn Gly Asp Gly Arg Ile Val Ala Ala Leu Ile Pro Ser Asp
            180                 185                 190

Arg Ala Gly Val Gln Val Asn Gly Asp Trp Asp Ser Leu Gly Met Arg
        195                 200                 205

Gln Thr Asp Ser Gly Ser Val Thr Phe Ser Gly Val Val Tyr Pro
    210                 215                 220

Asp Glu Leu Leu Gly Thr Pro Gly Gln Val Thr Asp Ala Phe Ala Ser
225                 230                 235                 240

Gly Ser Lys Pro Ser Leu Trp Thr Pro Ile Thr Gln Leu Ile Phe Thr
                245                 250                 255

His Leu Tyr Leu Gly Ile Ala Arg Gly Ala Leu Glu Glu Ala Ala His
            260                 265                 270

Tyr Ser Arg Ser His Ser Arg Pro Phe Thr Leu Ala Gly Val Glu Lys
        275                 280                 285

Ala Thr Glu Asp Pro Tyr Val Leu Ala Ile Tyr Gly Glu Phe Ala Ala
    290                 295                 300

Gln Leu Gln Val Ala Glu Ala Gly Ala Arg Glu Val Ala Leu Arg Val
305                 310                 315                 320

Gln Glu Leu Trp Glu Arg Asn His Val Thr Pro Glu Gln Arg Gly Gln
                325                 330                 335

Leu Met Val Gln Val Ala Ser Ala Lys Ile Val Ala Thr Arg Leu Val
            340                 345                 350

Ile Glu Leu Thr Ser Arg Leu Tyr Glu Ala Met Gly Ala Arg Ala Ala
        355                 360                 365

Ala Ser Arg Gln Phe Gly Phe Asp Arg Phe Trp Arg Asp Ala Arg Thr
    370                 375                 380

His Thr Leu His Asp Pro Val Ala Tyr Lys Ile Arg Glu Val Gly Asn
385                 390                 395                 400

Trp Phe Leu Asn His Arg Phe Pro Thr Pro Ser Phe Tyr Ser
                405                 410
```

<210> SEQ ID NO 7
<211> LENGTH: 9775
<212> TYPE: DNA
<213> ORGANISM: Paenibacillus sp.
<220> FEATURE:
<221> NAME/KEY: CDS
<222> LOCATION: (641)...(1936)
<220> FEATURE:
<221> NAME/KEY: CDS
<222> LOCATION: (7026)...(8321)

<400> SEQUENCE: 7

```
cccaggcttt acactttatg ctcccggctc gtatgttgtg tggaattgtg agcggataac    60
aatttcacac aggaaacagc tatgaccatg attacgccaa gcgcgcaatt aaccctcact   120
aaagggaaca aaagctgggt accgggcccc ccctcgaggt cgacggtatc gataagcttc   180
tccggcggca ctttatagcc gtatttcatc aaaatggcta cggccaagct gtctgccccg   240
```

-continued

```
cccgaaaaat tgatgtggta ctcatcataa gagcgaatat cgagcaattc ttggggcagc    300
tccgccaaca catactgttc cgcgctccgc acttcttcac gatttgaagc caatatcgat    360
tacctccttt tttgggcata aaaaaccgc ggaaacacaa aaagacacca aattaggtgt     420
cctattgtct ccacggctaa ataaagccca ttatttatac gtcggttgaa gcgtaccgac    480
attccccttc tttgtcgaat aataacgac aaagaaaatc acaacagctt gtaatactat    540
taatgtatca tttgcaaaaa aaatcgtcaa tattacccag ccattgttgt tgttgttctg    600
tgatattgtc agggtgtaac tgatccgaga aaatgtcagt atg agc aag gag cag     655
                                             Met Ser Lys Glu Gln
                                              1               5 atc acc ttg aca aag aac gaa ctg aaa cgc gtt atg gtc att gaa aaa    703
Ile Thr Leu Thr Lys Asn Glu Leu Lys Arg Val Met Val Ile Glu Lys
         10                  15                  20 tgg atc gac ggc cat ctc acg gaa cag gat gtt gca cgc aac ctg ggc    751
Trp Ile Asp Gly His Leu Thr Glu Gln Asp Val Ala Arg Asn Leu Gly
             25                  30                  35 atc agt gtc cgt caa gcg tat cgg ctc aag gcc aaa tat cgt cac gga    799
Ile Ser Val Arg Gln Ala Tyr Arg Leu Lys Ala Lys Tyr Arg His Gly
         40                  45                  50 ggt gca caa gcg atc gca cat ggg aat cgg ggc cgt aag ccg gct cac    847
Gly Ala Gln Ala Ile Ala His Gly Asn Arg Gly Arg Lys Pro Ala His
 55                  60                  65 acc ttg acc gat tcg ctc aaa caa cgc gtt atg ctc ctg tat cag gag    895
Thr Leu Thr Asp Ser Leu Lys Gln Arg Val Met Leu Leu Tyr Gln Glu
 70                  75                  80                  85 cgc tac ttc gga agc aat gcc acc cac ttt gcc gag ctg ttg gcc gaa    943
Arg Tyr Phe Gly Ser Asn Ala Thr His Phe Ala Glu Leu Leu Ala Glu
             90                  95                 100 cac gaa aac atc cat tta agc gtc tct tcg gtc cgc cgc att ctg ctg    991
His Glu Asn Ile His Leu Ser Val Ser Ser Val Arg Arg Ile Leu Leu
            105                 110                 115 gaa ggc ggg ttg cgt ccc gcg cgg ctg cgc cgt cgt ccg aag gct cac   1039
Glu Gly Gly Leu Arg Pro Ala Arg Leu Arg Arg Arg Pro Lys Ala His
        120                 125                 130 cga ccc cgg ccc cgc aaa cct cag gcg ggc atg ctg tgg cag atc gat   1087
Arg Pro Arg Pro Arg Lys Pro Gln Ala Gly Met Leu Trp Gln Ile Asp
135                 140                 145 gct tct ccc tat gcc tgg ctg gag gat cgc ggt ccc atg ctc acc ctg   1135
Ala Ser Pro Tyr Ala Trp Leu Glu Asp Arg Gly Pro Met Leu Thr Leu
150                 155                 160                 165 cac ggc atc atc gat gac gcc acc ggg gaa gtg gtc gcg gcc acc ttc   1183
His Gly Ile Ile Asp Asp Ala Thr Gly Glu Val Val Ala Ala Thr Phe
            170                 175                 180 cgc ccg acc gaa aca ctg gag ggc tac gtg acc gtc atg atc gag gga   1231
Arg Pro Thr Glu Thr Leu Glu Gly Tyr Val Thr Val Met Ile Glu Gly
        185                 190                 195 ctt agg cgc aaa ggc gta ccg ctt gcg ctc tac agc gac caa cac tcc   1279
Leu Arg Arg Lys Gly Val Pro Leu Ala Leu Tyr Ser Asp Gln His Ser
    200                 205                 210 att ttt cac ccg ccc aag ggc aag cca acc ctc gag cag gaa ttg gcc   1327
Ile Phe His Pro Pro Lys Gly Lys Pro Thr Leu Glu Gln Glu Leu Ala
215                 220                 225 ggt gag ccg ccg tcg ctt tcc acc ttc gga cag gcc ctc gcc gat ctg   1375
Gly Glu Pro Pro Ser Leu Ser Thr Phe Gly Gln Ala Leu Ala Asp Leu
230                 235                 240                 245 ggc att acc cat atc gag gcg ctg tca ccc caa gcc aaa gga cgg atc   1423
Gly Ile Thr His Ile Glu Ala Leu Ser Pro Gln Ala Lys Gly Arg Ile
```

-continued

| | | | | | | | | | | | | | | | | |
|---|---|---|---|---|---|---|---|---|---|---|---|---|---|---|---|---|
| | | | | 250 | | | | | 255 | | | | | 260 | | |

```
gaa cgg ctc tgg caa acc ttt cag gat cgc ctg gtg atc gaa ctt agg      1471
Glu Arg Leu Trp Gln Thr Phe Gln Asp Arg Leu Val Ile Glu Leu Arg
            265                     270                     275 ctg cgc aac gtg tgc acg atg gag gaa gcc aat cgc gtg tta ccg gaa      1519
Leu Arg Asn Val Cys Thr Met Glu Glu Ala Asn Arg Val Leu Pro Glu
            280                     285                     290 ctt atc gcc aag cac aat cgt cag ttt gcc gtc gcg ccg caa gaa gct      1567
Leu Ile Ala Lys His Asn Arg Gln Phe Ala Val Ala Pro Gln Glu Ala
            295                     300                     305 gaa ccg gcc tac cgg ccg ctg ccc gaa acg cct ttg gag cat atc ttc      1615
Glu Pro Ala Tyr Arg Pro Leu Pro Glu Thr Pro Leu Glu His Ile Phe
310                     315                     320                 325 acg cgt cgg gaa tac cgg cgc atc agc ggc ggg cag acg ttc ttc tgg      1663
Thr Arg Arg Glu Tyr Arg Arg Ile Ser Gly Gly Gln Thr Phe Phe Trp
                330                     335                     340 aaa ggg aaa tgc tac atg cca aag ccc gtc ccc ggt gtt ccg cgc tgg      1711
Lys Gly Lys Cys Tyr Met Pro Lys Pro Val Pro Gly Val Pro Arg Trp
            345                     350                     355 gaa gcg aag agc gtc gtc gaa gtg cgt gtc ggc atg gat gga caa gtg      1759
Glu Ala Lys Ser Val Val Glu Val Arg Val Gly Met Asp Gly Gln Val
            360                     365                     370 tgg ctg tgg gat caa ggg cgg gcc tgg cct tgt gtg gag aca cag gcc      1807
Trp Leu Trp Asp Gln Gly Arg Ala Trp Pro Cys Val Glu Thr Gln Ala
375                     380                     385 aca cag acc ccg gcg cca aca acg gcc aaa aaa gaa gcg gcg cct gcg      1855
Thr Gln Thr Pro Ala Pro Thr Thr Ala Lys Lys Glu Ala Ala Pro Ala
390         395                     400                     405 tcc ccc cgc aag ccc gct gca aac cat ccc tgg aga aaa cca ttc tcc      1903
Ser Pro Arg Lys Pro Ala Ala Asn His Pro Trp Arg Lys Pro Phe Ser
                410                     415                     420 agc aag cag tta cag cgt agc aca gca tcc ggc tagtctgcaa gaggacggcg    1956
Ser Lys Gln Leu Gln Arg Ser Thr Ala Ser Gly
            425                     430 gctgtttaat caactatcat ccctgacatt tcatagaac agttaacctg acattttcac     2016
agacgcttga caggggaac tatcatgagt ttgagcgagc gaattgacga agcgatccga     2076
aatcatgagg aatgggtgct ccggaggcag aaggggattc ccaataacct gcggctgttt   2136
gtcctggcct gcatggatga acgacttccg gtggaagaca ttctcgggct gcagcccggg   2196
gatgcccatg tgttccgcaa tgccggaggg gttgtgaccg acgacgtcat ccgctcggcg   2256
gccctcaccc tgaacttctt cgggacgaaa gaaatcatcg tgatcaatca caccgaatgc   2316
ggcatgatga ccgccggcgg ccgggaagtt gtcgacggtc tccgggccaa actcaacata   2376
gacgtggaac gggttccgtt ggatccctcc ctccccgagc tggtactgag cgagccggca   2436
gctttcgaaa atggttccg tacctttgac aatgtggacg aggcgaccgt ggcccaagtc    2496
gaatacctgc gcaaccaccc gctgattccg aaggacacca tcatcaacgg atatatatat   2556
gaagtgagga caaaccgcct gcgccgcccg caccaattat tgagccgccg ggtgaatacc   2616
cgcgacgaac tgctcgggcg gagataagag aaacgccgat gaaaactccc gtcagggaaa   2676
atgtttttcg ggctgcctca catccaaggg gcagcccttc ggtatttatc cggcactaga   2736
gtgaacctgt ccgcccggg gtatgatgga accgagaggc ttcggtcctg gtccattttc    2796
tcaacgtggt gttttgaagat tccggccatc ccctgttgtt cgacgtggaa ccgttgggac   2856
atcgagaagc ggacccttta ctactgggcg aaaatgcttg agagtcacag cacgttccat   2916
ctgcgcgagg atgcgacggg ggtgttgctg gccgatctgt tggagataca ttttgtggaa   2976
```

```
ctggaatgtc gatctcatcc ggcgttaccc ccaatcccat cctcaaataa atctattcac   3036
actaaatttc aagagtaaaa gctgggggtt ggaaaccggt gattgaggaa ccagtttcct   3096
acttcgcgta tcttataggc taccgggtca tgtaaggtat gcgtgcgcgc gtcgcgccaa   3156
aagcggtcaa agccgaattg gcggctcgct gcagcccgtg cccccatcgc ttcatataga   3216
cggcttgtca gttcgatcac caaacgcgtg gcgacgattt tggcactggc cacttgtacc   3276
attaactgcc cccgctgctc aggagtgacg tgattccgct cccacaattc ctgaacccgc   3336
aacgccacct ctcgggctcc agcctccgcg acctgaagtt gtgcagcaaa ttccccataa   3396
atcgctagca cataaggatc ctcggtggct ttctccaccc ctgcgagtgt aaatggtctc   3456
gaatgggacc tcgagtagtg agcggcctct tcaagagcgc cacgggcaat gccgaggtac   3516
aggtgggtaa agatcagttg ggtgatgggt gtccaaagac tgggcttcga accggaagca   3576
aacgcatccg tcacttggcc gggtgtcccc agcaactcgt cgggatagac caccacaccc   3636
gaaaatgtaa cgctcccact atcggtttga cgcatacccc ggctgtccca atcgccattt   3696
acctgaaccc cagcacgatc cgaggggatg agtgccgcga cgatcctgcc atctccgttt   3756
ggatccctgc tggtgacggc aaacacaagc aacctgtccg catcggccga gccgctgcaa   3816
aaggccttgg tcccgttgat ctcataactg ccgtccggta acgggtcgc cgtcacacgc    3876
caatccagaa cgtgcgcatt gttttcgctg gatgcattcc caaggaacca acgctcgcgg   3936
acagcctgtg gataccaacg agccttctgc tcaggtgaag caaagagatc cacataggca   3996
aaatttgaaa aatgataacc aaacaggtgc ccaagggagg cgtcggcgct ggcaatctca   4056
gcgatggctt cgtatacggt cggccaactt tctccgagtc ccccgcgctc tttactgata   4116
agtagagtaa ggaggccact acggcgaatc gcgtcgcgct ccgccttcgg ggttcccccc   4176
gcacgctccc tttcccgaac ggtcacacga aacgtcttgg ccagttctgt cgccacgtct   4236
aaagcacgat gatcttcacg gactgcagat gaattggcat ggattgttct cattagaaaa   4296
actcctcctc acaaagatgc gttgtccaga aattcggggg ccgcccaacg ctctatatcc   4356
accaaccggt cgatcagccc gtggtcgaaa agaaattgct gggtctgctc cagaatgcgc   4416
agagccgcct gatccagccg cggtcgcagg tccctatgaa acccttcgcc aaatcccgtc   4476
tccacggcct tcacggaaac cccaaggttc aaggcatgga tttcaatggt ctccttggcg   4536
tgatcggttg cccaggacgc agcctccacg acggagtcga ccaagcgttg gacgatctcc   4596
ggcctgcgct ccactagagc cgcgctgacc gtccaaacgc tcgcccaggc attctcctct   4656
cctgtcaacg caaagaccgg cttagccaca ccttgaagtt caagctcggc agcataggga   4716
agccaggaaa acagggcgtc tacctgcccg cttttcaact gttgactctg ccattcaacc   4776
gccgtagcaa acaactctcg ggagctgaag tccctactgt catccagttt aggtcgcggg   4836
acatccaccc atgggttttc aacatcttca acaatgacgt cattcagtct caaaccgccg   4896
gccgccaacg tatgcttgag cgctcgaact tcccacgatc ccaggcgac gagcgtttgc    4956
tcccaagggc caaggttccg atattcctcg cccagatggc cgaaaaggat cctctgtgca   5016
gctcggctca ggccgatgcg gcgccctcta agatccgatg gtgaagcaat cttaccggca   5076
gaatgcacat aaaaccttg gcgaggcttc agaaccgtga ttcccaacaa acgtgtccgc    5136
cccggagcac gcagcccttc gctcaccagc ggtggtatct cgccgccaaa tcgggtgtag   5196
gctgcatgat catacgcaaa atgtgtcgcc ccttgggcaa aggcgatctg cgagagaaga   5256
acaccttgac gctctagctt ccccgtccgt gaggccacga gcaaagcgtt tgcaaccgga   5316
```

-continued

```
caattactat acgcaacgcg gtcgggcca atggctgaga gcgtgctcat cgctcaccc    5376 cctgtacagc ttcttcggct tcgctaacgt cttccagacc gagatgctgg cgcaaggtat    5436 cccccttcata ctcccgtctg aaaagacccc ggtcctgcaa aataggaacc actttgtcga   5496
caaattcctc gtaagcgccg ggcagatagt agggagagat cacgaagccg tcggccgccg    5556
gttcattgaa cagagattcc aactcccctg ccacctgctc cggggttcca accaactgcg    5616
gtacgagtac ccagccatag cgaacccta ggtcgcgcaa cgttaagttt tctgtctctg     5676
tcagtttcac caccatctct aaaagacctc tcgtcccacc cacctcaccg accgcatcca    5736
gcacctcacg aattggagca tccaaaggat agcgggaaaa atccactccg caatggcttg    5796
acagggtaga gagaccagct tctggtatca ctagctgatt cacttcttcc tgccgctcgc    5856
gcgcttcctt ctccgtatcg ccaagaatcg gaatgacggc agggagtatt ttgcaattct    5916
cgggacggcg tcctgcggcg attacctgtt ttttcaagtc ttcgtaaaac gcccgcatcg    5976
cgactcggtt cggcgcaatg gtgaaaacgg cttctgccca ccgagcagca aatgtctttc    6036
cacgggcgga ggatcccgcc tgaatgatga caggacgacc ctgtggcgac cgcgggactt    6096
gtaacgggcc ccggacggag aaccaggttc cggagtgatc aatatagtgg acctttctgg    6156
gatcagcaaa aagaccctgt tttttgtcga ggagcaatgc atcctgatcc caactcctcc    6216
acaatttatc tgtaatctca agaaactcat cggcacggtc gtaccgacta tcgtgatcca    6276
ggtgttcctc atacccaaag ttcctggcct cggcgttgtt gagtgaggtc acgacattcc    6336
aggctgccct tccttttgtt aagtgatcca gcgtagcaaa cactcttgcc acatggtaag    6396
gaggatagta ggttgtcgaa atcgtggccc ccaggcccag tctctccgtg gccgcagcca    6456
tggtggcgag cacggggacg ggatccagaa aagcggctcc ttggcctcca aatctcaatc    6516
cagcatcaag attgtttccg tagctatccc aaatagccaa accgtcaggc agaaagagca    6576
ggtcaaagcg gccgcgctcg agtgtacggg cgatgtgttg ataccaagaa atagacaaaa    6636
aaccattatc agttttcggg tgacgccatg ccccgtggtg atgggtcaca ttacccgctg    6696
caaaaaaacc ggcaagatgc atttgacgca tcgattgaac cctcccatg tatgttcctg     6756 cgtgaatgtt cttcaatggt catccaggag cagaaaactg tttttcggcc tcctctgca    6816 aaagaaaaag ccccccgctt tccggcaaaa ttaccgcaaa gtcagagggc ctctggtggt    6876
ccagtcagcc gaggtaaacc cgattaaatt gattagtatt tatgaatcgg agtataccgt    6936
tcaggattca ttttgtcaac ccgtcgcaat cactcatgtt gttgttctgt gatattgtca    6996
gggtgtaact gatccgagaa aatgtcagt atg agc aag gag cag atc acc ttg      7049
                                Met Ser Lys Glu Gln Ile Thr Leu
                                                435             440 aca aag aac gaa ctg aaa cgc gtt atg gtc att gaa aaa tgg atc gac      7097
Thr Lys Asn Glu Leu Lys Arg Val Met Val Ile Glu Lys Trp Ile Asp
            445                 450                 455 ggc cat ctc acg gaa cag gat gtt gca cgc aac ctg ggc atc agt gtc      7145
Gly His Leu Thr Glu Gln Asp Val Ala Arg Asn Leu Gly Ile Ser Val
        460                 465                 470 cgt caa gcg tat cgg ctc aag gcc aaa tat cgt cac gga ggt gca caa      7193
Arg Gln Ala Tyr Arg Leu Lys Ala Lys Tyr Arg His Gly Gly Ala Gln
    475                 480                 485 gcg atc gca cat ggg aat cgg ggc cgt aag ccg gct cac acc ttg acc      7241
Ala Ile Ala His Gly Asn Arg Gly Arg Lys Pro Ala His Thr Leu Thr
490                 495                 500 gat tcg ctc aaa caa cgc gtt atg ctc ctg tat cag gag cgc tac ttc      7289
Asp Ser Leu Lys Gln Arg Val Met Leu Leu Tyr Gln Glu Arg Tyr Phe
505                 510                 515                 520
```

```
gga agc aat gcc acc cac ttt gcc gag ctg ttg gcc gaa cac gaa aac    7337
Gly Ser Asn Ala Thr His Phe Ala Glu Leu Leu Ala Glu His Glu Asn
                525                 530                 535 atc cat tta agc gtc tct tcg gtc cgc cgc att ctg ctg gaa ggc ggg    7385
Ile His Leu Ser Val Ser Ser Val Arg Arg Ile Leu Leu Glu Gly Gly
            540                 545                 550 ttg cgt ccc gcg cgg ctg cgc cgt cgt ccg aag gct cac cga ccc cgg    7433
Leu Arg Pro Ala Arg Leu Arg Arg Arg Pro Lys Ala His Arg Pro Arg
        555                 560                 565 ccc cgc aaa cct cag gcg ggc atg ctg tgg cag atc gat gct tct ccc    7481
Pro Arg Lys Pro Gln Ala Gly Met Leu Trp Gln Ile Asp Ala Ser Pro
    570                 575                 580 tat gcc tgg ctg gag gat cgc ggt ccc atg ctc acc ctg cac ggc atc    7529
Tyr Ala Trp Leu Glu Asp Arg Gly Pro Met Leu Thr Leu His Gly Ile
585                 590                 595                 600 atc gat gac gcc acc ggg gaa gtg gtc gcg gcc acc ttc cgc ccg acc    7577
Ile Asp Asp Ala Thr Gly Glu Val Val Ala Ala Thr Phe Arg Pro Thr
                605                 610                 615 gaa aca ctg gag ggc tac gtg acc gtc atg atc gag gga ctt agg cgc    7625
Glu Thr Leu Glu Gly Tyr Val Thr Val Met Ile Glu Gly Leu Arg Arg
            620                 625                 630 aaa ggc gta ccg ctt gcg ctc tac agc gac caa cac tcc att ttt cac    7673
Lys Gly Val Pro Leu Ala Leu Tyr Ser Asp Gln His Ser Ile Phe His
        635                 640                 645 ccg ccc aag ggc aag cca acc ctc gag cag gaa ttg gcc ggt gag ccg    7721
Pro Pro Lys Gly Lys Pro Thr Leu Glu Gln Glu Leu Ala Gly Glu Pro
    650                 655                 660 ccg tcg ctt tcc acc ttc gga cag gcc ctc gcc gat ctg ggc att acc    7769
Pro Ser Leu Ser Thr Phe Gly Gln Ala Leu Ala Asp Leu Gly Ile Thr
665                 670                 675                 680 cat atc gag gcg ctg tca ccc caa gcc aaa gga cgg atc gaa cgg ctc    7817
His Ile Glu Ala Leu Ser Pro Gln Ala Lys Gly Arg Ile Glu Arg Leu
                685                 690                 695 tgg caa acc ttt cag gat cgc ctg gtg atc gaa ctt agg ctg cgc aac    7865
Trp Gln Thr Phe Gln Asp Arg Leu Val Ile Glu Leu Arg Leu Arg Asn
            700                 705                 710 gtg tgc acg atg gag gaa gcc aat cgc gtg tta ccg gaa ctt atc gcc    7913
Val Cys Thr Met Glu Glu Ala Asn Arg Val Leu Pro Glu Leu Ile Ala
        715                 720                 725 aag cac aat cgt cag ttt gcc gtc gcg ccg caa gaa gct gaa ccg gcc    7961
Lys His Asn Arg Gln Phe Ala Val Ala Pro Gln Glu Ala Glu Pro Ala
    730                 735                 740 tac cgg ccg ctg ccc gaa acg cct ttg gag cat atc ttc acg cgt cgg    8009
Tyr Arg Pro Leu Pro Glu Thr Pro Leu Glu His Ile Phe Thr Arg Arg
745                 750                 755                 760 gaa tac cgg cgc atc agc ggc ggg cag acg ttc ttc tgg aaa ggg aaa    8057
Glu Tyr Arg Arg Ile Ser Gly Gly Gln Thr Phe Phe Trp Lys Gly Lys
                765                 770                 775 tgc tac atg cca aag ccc gtc ccc ggt gtt ccg cgc tgg gaa gcg aag    8105
Cys Tyr Met Pro Lys Pro Val Pro Gly Val Pro Arg Trp Glu Ala Lys
            780                 785                 790 agc gtc gtc gaa gtg cgt gtc ggc atg gat gga caa gtg tgg ctg tgg    8153
Ser Val Val Glu Val Arg Val Gly Met Asp Gly Gln Val Trp Leu Trp
        795                 800                 805 gat caa ggg cgg gcc tgg cct tgt gtg gag aca cag gcc aca cag acc    8201
Asp Gln Gly Arg Ala Trp Pro Cys Val Glu Thr Gln Ala Thr Gln Thr
    810                 815                 820 ccg gcg cca aca acg gcc aaa aaa gaa gcg gcg cct gcg tcc ccc cgc    8249
Pro Ala Pro Thr Thr Ala Lys Lys Glu Ala Ala Pro Ala Ser Pro Arg
```

```
825                830                835                840
aag ccc gct gca aac cat ccc tgg aga aaa cca ttc tcc agc aag cag    8297
Lys Pro Ala Ala Asn His Pro Trp Arg Lys Pro Phe Ser Ser Lys Gln
                845                850                855 tta cag cgt agc aca gca tcc ggc tagtctgcaa gaggacggcg gctgtttaat  8351
Leu Gln Arg Ser Thr Ala Ser Gly
            860 caactatcat ccctgacatt ttcatagaac agttaacctg acattttcac agacgcttga 8411 catattaccc agccattgtc caaccaaaac tctaaaattg tggtatgctg ccgaaatttg 8471 aaaagataaa taggaagagt ggaatgctcc acccttccca tttatcacag cgcaaattcc 8531 aattgcccgt tcgcggcaag cgacatcggt accacagcag ccgtcatgtc ttgatcttgg 8591 ttcatcgcaa cgtcggaaat gattttgccg tgctttgccg ccagcttctg gagcagtttc 8651 aattcatgtt gctgcgcctt ataagcaaat tcagcgcgga tctgctccgc atgttgcagc 8711 acatattcct tcagttcgcg gttaaactct ccgtattcac cgtagcacaa ataatagcac 8771 tgctcaaaat gctcaatgaa atcaagaaac cctttatcgg aatatgtctc tttgaagcca 8831 tagatgtcat aatgcgcgat gaagcctgca tgaagatgca ataattgta aagctgcttg 8891 tccatgtgat tgatgtcgcg ggtatcaatg accttcttaa acttcttgaa attttttgcg 8951 gtatccacct tcatttgctc aagctccccc ttaacttgcg cgatatttcc acccttataa 9011 aaaaagaaaa aggggcataa aatacgcccc caatttttcct tacccgacaa gaccgatcga 9071 cgattttttca atcacgagtc cgttttcggt gcgttcaatc caccggtcgc caggatcgcg 9131 actgagcctt tcaacacggg ctttagcgtc cctcagtcga gtccccgtaa ttaacttacg 9191 gagcgtggac ccgtcttcca gatgataaag cacaggtacc ccgtatccgt gttgcgtctt 9251 ctcgtgtttc tcgtcaagtg gttcgatgcg aattaccctg ataccattct cccgaacgcc 9311 ggccactcca ctttccggga cctctacctc ggcgcccccc tgttccgcag gaagctcctc 9371 ggcagaaagg atttcagcgt cctcctcttt tgtagacggg gatacagcat tgtccggatc 9431 atgttggagt tggccactct cgcttgattg cagtccggag tcagcttcct ggtcatacgg 9491 cgcagctgct accgaagcgg aatcgttatt ggcgccggcc acatcttctg cataaaccgg 9551 cctgcagttc ccggtctttg cattaaaatt gacataatgg acgagaatgg cgttcgacga 9611 aaacagctca ttcacgacgg tcgaaatcag catcgcggcc atttcattgg aaatcatccg 9671 ttgcggctga tacggttcga ccccgcagga atgcgaagga ggaattgcgt cctttgcatt 9731 gatcggataa accgcatcga gcggcggcaa gatgacgcgg ccgc                 9775

<210> SEQ ID NO 8
<211> LENGTH: 432
<212> TYPE: PRT
<213> ORGANISM: Paenibacillus sp.

<400> SEQUENCE: 8

Met Ser Lys Glu Gln Ile Thr Leu Thr Lys Asn Glu Leu Lys Arg Val
  1               5                  10                  15

Met Val Ile Glu Lys Trp Ile Asp Gly His Leu Thr Glu Gln Asp Val
                 20                  25                  30

Ala Arg Asn Leu Gly Ile Ser Val Arg Gln Ala Tyr Arg Leu Lys Ala
             35                  40                  45

Lys Tyr Arg His Gly Gly Ala Gln Ala Ile Ala His Gly Asn Arg Gly
         50                  55                  60

Arg Lys Pro Ala His Thr Leu Thr Asp Ser Leu Lys Gln Arg Val Met
```

-continued

```
                65                  70                  75                  80
         Leu Leu Tyr Gln Glu Arg Tyr Phe Gly Ser Asn Ala Thr His Phe Ala
                             85                  90                  95

Glu Leu Leu Ala Glu His Glu Asn Ile His Leu Ser Val Ser Ser Val
                         100                 105                 110

Arg Arg Ile Leu Leu Glu Gly Gly Leu Arg Pro Ala Arg Leu Arg Arg
                     115                 120                 125

Arg Pro Lys Ala His Arg Pro Arg Pro Arg Lys Pro Gln Ala Gly Met
                 130                 135                 140

Leu Trp Gln Ile Asp Ala Ser Pro Tyr Ala Trp Leu Glu Asp Arg Gly
         145                 150                 155                 160

Pro Met Leu Thr Leu His Gly Ile Ile Asp Asp Ala Thr Gly Glu Val
                             165                 170                 175

Val Ala Ala Thr Phe Arg Pro Thr Glu Thr Leu Glu Gly Tyr Val Thr
                         180                 185                 190

Val Met Ile Glu Gly Leu Arg Arg Lys Gly Val Pro Leu Ala Leu Tyr
                     195                 200                 205

Ser Asp Gln His Ser Ile Phe His Pro Pro Lys Gly Lys Pro Thr Leu
                 210                 215                 220

Glu Gln Glu Leu Ala Gly Glu Pro Pro Ser Leu Ser Thr Phe Gly Gln
         225                 230                 235                 240

Ala Leu Ala Asp Leu Gly Ile Thr His Ile Glu Ala Leu Ser Pro Gln
                             245                 250                 255

Ala Lys Gly Arg Ile Glu Arg Leu Trp Gln Thr Phe Gln Asp Arg Leu
                         260                 265                 270

Val Ile Glu Leu Arg Leu Arg Asn Val Cys Thr Met Glu Glu Ala Asn
                     275                 280                 285

Arg Val Leu Pro Glu Leu Ile Ala Lys His Asn Arg Gln Phe Ala Val
                 290                 295                 300

Ala Pro Gln Glu Ala Glu Pro Ala Tyr Arg Pro Leu Pro Glu Thr Pro
         305                 310                 315                 320

Leu Glu His Ile Phe Thr Arg Arg Glu Tyr Arg Arg Ile Ser Gly Gly
                             325                 330                 335

Gln Thr Phe Phe Trp Lys Gly Lys Cys Tyr Met Pro Lys Pro Val Pro
                         340                 345                 350

Gly Val Pro Arg Trp Glu Ala Lys Ser Val Val Glu Val Arg Val Gly
                     355                 360                 365

Met Asp Gly Gln Val Trp Leu Trp Asp Gln Gly Arg Ala Trp Pro Cys
                 370                 375                 380

Val Glu Thr Gln Ala Thr Gln Thr Pro Ala Pro Thr Thr Ala Lys Lys
         385                 390                 395                 400

Glu Ala Ala Pro Ala Ser Pro Arg Lys Pro Ala Ala Asn His Pro Trp
                             405                 410                 415

Arg Lys Pro Phe Ser Ser Lys Gln Leu Gln Arg Ser Thr Ala Ser Gly
                         420                 425                 430

<210> SEQ ID NO 9
<211> LENGTH: 432
<212> TYPE: PRT
<213> ORGANISM: Paenibacillus sp.

<400> SEQUENCE: 9

Met Ser Lys Glu Gln Ile Thr Leu Thr Lys Asn Glu Leu Lys Arg Val
         1               5                   10                  15
```

-continued

```
Met Val Ile Glu Lys Trp Ile Asp Gly His Leu Thr Glu Gln Asp Val
            20                  25                  30

Ala Arg Asn Leu Gly Ile Ser Val Arg Gln Ala Tyr Arg Leu Lys Ala
        35                  40                  45

Lys Tyr Arg His Gly Gly Ala Gln Ala Ile Ala His Gly Asn Arg Gly
 50                  55                  60

Arg Lys Pro Ala His Thr Leu Thr Asp Ser Leu Lys Gln Arg Val Met
 65                  70                  75                  80

Leu Leu Tyr Gln Glu Arg Tyr Phe Gly Ser Asn Ala Thr His Phe Ala
                85                  90                  95

Glu Leu Leu Ala Glu His Glu Asn Ile His Leu Ser Val Ser Ser Val
                100                 105                 110

Arg Arg Ile Leu Leu Glu Gly Gly Leu Arg Pro Ala Arg Leu Arg Arg
            115                 120                 125

Arg Pro Lys Ala His Arg Pro Arg Pro Arg Lys Pro Gln Ala Gly Met
        130                 135                 140

Leu Trp Gln Ile Asp Ala Ser Pro Tyr Ala Trp Leu Glu Asp Arg Gly
145                 150                 155                 160

Pro Met Leu Thr Leu His Gly Ile Ile Asp Asp Ala Thr Gly Glu Val
                165                 170                 175

Val Ala Ala Thr Phe Arg Pro Thr Glu Thr Leu Glu Gly Tyr Val Thr
            180                 185                 190

Val Met Ile Glu Gly Leu Arg Arg Lys Gly Val Pro Leu Ala Leu Tyr
        195                 200                 205

Ser Asp Gln His Ser Ile Phe His Pro Pro Lys Gly Lys Pro Thr Leu
    210                 215                 220

Glu Gln Glu Leu Ala Gly Glu Pro Pro Ser Leu Ser Thr Phe Gly Gln
225                 230                 235                 240

Ala Leu Ala Asp Leu Gly Ile Thr His Ile Glu Ala Leu Ser Pro Gln
                245                 250                 255

Ala Lys Gly Arg Ile Glu Arg Leu Trp Gln Thr Phe Gln Asp Arg Leu
            260                 265                 270

Val Ile Glu Leu Arg Leu Arg Asn Val Cys Thr Met Glu Glu Ala Asn
        275                 280                 285

Arg Val Leu Pro Glu Leu Ile Ala Lys His Asn Arg Gln Phe Ala Val
    290                 295                 300

Ala Pro Gln Glu Ala Glu Pro Ala Tyr Arg Pro Leu Pro Glu Thr Pro
305                 310                 315                 320

Leu Glu His Ile Phe Thr Arg Arg Glu Tyr Arg Arg Ile Ser Gly Gly
                325                 330                 335

Gln Thr Phe Phe Trp Lys Gly Lys Cys Tyr Met Pro Lys Pro Val Pro
            340                 345                 350

Gly Val Pro Arg Trp Glu Ala Lys Ser Val Val Glu Val Arg Val Gly
        355                 360                 365

Met Asp Gly Gln Val Trp Leu Trp Asp Gln Gly Arg Ala Trp Pro Cys
    370                 375                 380

Val Glu Thr Gln Ala Thr Gln Thr Pro Ala Pro Thr Thr Ala Lys Lys
385                 390                 395                 400

Glu Ala Ala Pro Ala Ser Pro Arg Lys Pro Ala Ala Asn His Pro Trp
                405                 410                 415

Arg Lys Pro Phe Ser Ser Lys Gln Leu Gln Arg Ser Thr Ala Ser Gly
            420                 425                 430
```

```
<210> SEQ ID NO 10
<211> LENGTH: 21
<212> TYPE: PRT
<213> ORGANISM: Paenibacillus sp
<220> FEATURE:
<221> NAME/KEY: VARIANT
<222> LOCATION: 2, 5, 17-19
<223> OTHER INFORMATION: Xaa = any amino acid

<400> SEQUENCE: 10

Met Xaa Gln Met Xaa Leu Ala Gly Phe Phe Ala Ala Gly Asn Val Thr
 1               5                  10                  15

Xaa Xaa Xaa Gly Ala
            20

<210> SEQ ID NO 11
<211> LENGTH: 21
<212> TYPE: PRT
<213> ORGANISM: Paenibacillus sp.
<220> FEATURE:
<221> NAME/KEY: VARIANT
<222> LOCATION: 15, 20
<223> OTHER INFORMATION: Xaa = any amino acid

<400> SEQUENCE: 11

Thr Lys Ser Ala Ile Gly Pro Thr Arg Val Ala Tyr Ser Asn Xaa Pro
 1               5                  10                  15

Val Ala Asn Xaa Leu
            20

<210> SEQ ID NO 12
<211> LENGTH: 23
<212> TYPE: PRT
<213> ORGANISM: Rhodococcus sp

<400> SEQUENCE: 12

Met Thr Gln Gln Thr Gln Met His Ala Gly Phe Phe Ser Ala Gly Asn
 1               5                  10                  15

Val Thr His Ala His Gly Ala
            20

<210> SEQ ID NO 13
<211> LENGTH: 23
<212> TYPE: PRT
<213> ORGANISM: Rhodococcus sp.

<400> SEQUENCE: 13

Gly Ser Glu Leu Asp Ser Ala Ile Arg Asp Thr Leu Thr Tyr Ser Asn
 1               5                  10                  15

Cys Pro Val Pro Asn Ala Leu
            20

<210> SEQ ID NO 14
<211> LENGTH: 26
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 3, 12, 15, 18, 24
<223> OTHER INFORMATION: n = a, t, g, or c

<400> SEQUENCE: 14
ggnttyttyg cngcnggnaa ygtnac                                    26
```

<210> SEQ ID NO 15
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 6, 9, 12
<223> OTHER INFORMATION: n = a, t, g, or c

<400> SEQUENCE: 15
ttygcngcng gnaaygt                                                17

<210> SEQ ID NO 16
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 9, 12, 15
<223> OTHER INFORMATION: n = a, t, g, or c

<400> SEQUENCE: 16
ttyttygcng cnggnaa                                                17

<210> SEQ ID NO 17
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 3, 6, 15
<223> OTHER INFORMATION: n = a, t, g, or c

<400> SEQUENCE: 17
gcnggnttyt tygcngc                                                17

<210> SEQ ID NO 18
<211> LENGTH: 26
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 3, 6, 12, 15, 18, 24
<223> OTHER INFORMATION: n = a, t, g, or c

<400> SEQUENCE: 18
tangcnacyc tngtnggncc datngc                                      26

<210> SEQ ID NO 19
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 3, 6, 12, 15
<223> OTHER INFORMATION: n = a, t, g, or c

<400> SEQUENCE: 19
tangcnacyc tngtngg                                                17

```
<210> SEQ ID NO 20
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 6, 9, 12
<223> OTHER INFORMATION: n = a, t, g, or c

<400> SEQUENCE: 20
tcrttnacng cngtytc                                                17

<210> SEQ ID NO 21
<211> LENGTH: 17
<212> TYPE: DNA
<213> ORGANISM: Artificial Sequence
<220> FEATURE:
<223> OTHER INFORMATION: Synthetically generated primer
<220> FEATURE:
<221> NAME/KEY: misc_feature
<222> LOCATION: 6, 9, 12
<223> OTHER INFORMATION: n = a, t, g, or c

<400> SEQUENCE: 21
acyctngtng gnccdat                                                17
```

GENES ENCODING DESULFURIZATION ENZYMES

This is a divisional application of U.S. patent application No. 09/647,540, filed Sep. 29, 2001 now U.S. Pat. No. 6,420,158 which was the National Stage of International Application No. A PCT/JP99/01756, filed Apr. 2, 1999, which in turn claims the benefit of Japanese Application No. 090387/1998, filed Apr. 2, 1998, and Japanese Application No. 310545/1998, filed Oct. 30, 1998.

TECHNICAL FIELD

The present invention relates to ecysmes having the function of decomposing, using microorganisms, thiophene compounds, namely benzothiophene, dibenzothiophene (hereinafter referred to as "DBT") and their substituted compounds, or derivatives thereof, and genes encoding the enzymes. By using the enzymes and the gene defined in the present invention, sulfur can be released from benzothiophene, DBT and their substituted compounds, or derivatives thereof which are contained in fossil fuels such as petroleum. As a result, sulfur, which is generally diffused in the air when fossil fuels such as petroleum and coal are burned, can be easily removed from the fossil fuel.

PRIOR ART

In order to remove sulfur from hydrocarbon fuel such as petroleum, methods including alkali treating or solvent desulfurization are known. However, at present, mainly hydrodesulfurization is used. Hydrodesulfurization is a method for reacting sulfur compounds in a petroleum fraction with hydrogen in the presence of a catalyst and removing the produced hydrogen sulfide so as to obtain low-sulfur products. As a catalyst, metallic catalysts such as cobalt, moltybdenum, nickel and tungsten are used with alumina as a carrier. When the molybdenum on alumina is used as the catalyst, usually cobalt or nickel is added as a promoter to enhance catalysis performance. The hydrodesulfurization with metallic catalysts is undoubtedly a fine process which is widely used throughout the world at the moment. However, as a process for producing petroleum products adapted to more strict environmental regulations, there are some problems. Some examples, are discussed below briefly.

Generally the substrate specificity of a metallic catalyst is low, and so it is suitable for decomposing various kinds of sulfur compounds and lowering the amount of sulfur contained in the fossil fuel as a whole. However, it is considered that the effect of desulfurization with metallic catalyst is sometimes insufficient for a specific group of sulfur compounds, i.e., heterocyclic sulfur compounds such as benzothiophene, DBT and their alkyl derivatives. For example, after desulfurizing light oil, various heterocyclic organic sulfur compounds still remain. One reason why the effect of desulfurization with metallic catalyst is insufficient would be steric hindrance caused by substituents which are around the sulfur atoms of the organic sulfur compounds. Among these substituted compounds, the influence of a methyl substituted compound on the reaction of a metallic catalyst has been studied in relation to thiophene, benzothiophene, DBT and so on. According to such studies, it is generally said that, as the number of substituted compounds increases, desulfurization reaction rates decreases. However, it is also said that the position of the substituents have a very large influence on the reactivity. One of the reports which have shown that the steric hindrance has the significant influence on the reaction of metallic catalyst is, for example, Houalla, M., Broderick, D. H., Sapre, A. V., Nag, N. K., de Beer, V. H., Gates, B. C., Kwart, H. J., Catalt., 61, 523–527(1980). In fact, it is known that a considerable amount of various alkyl derivatives of DBT exists in light oil (e.g. Kabe, T., Ishihara, A. and Tajima, H. Ind. Eng. Chem. Res., 31, 1577–1580(1992)).

As stated above, it is considered that, in order to desulfurize organic sulfur compounds which are resistant against hydrodesulfurization, higher reaction temperature and pressure than that usually used are required, and also the amount of hydrogen added to be increased remarkably. It is thus expected that enormous capital investment and operating costs are needed to improve a hydrodesulfurization process such as this. For example, light oil contains organic sulfur compounds resisting such hydrodesulfurization as a major compound species, and as stated above, a substantial improvement on the hydrodesulfurization process is required to carry out more sophisticated desulfurization of light oil (an ultra deep desulfurization).

On the other hand, the enzyme-reaction in an organism proceeds under relatively mild conditions, and further, the rate of enzyme reaction in an organism compares favorably with that of a chemical catalyst. Moreover, there are so many kinds of enzymes in vivo to conform appropriately to various kinds of vital reactions occurring therein, and those enzymes usually show a very high substrate specificity. These characteristics are expected to be utilized for so-called biodesulfurization reaction, which removes sulfur from sulfur compounds in fossil fuel by using-microorganisms (Monticello, D. J., Hydrocarbon Processing 39–45(1994)).

There are a large number of reports on methods for removing sulfur from heterocyclic sulfur compounds which are ingredients of petroleum by using bacteria, and these methods are broadly divided into the reaction of decomposing a ring (C—C bond cleavage) and the C—S bond cleavage reaction. As bacteria having C—C-bond—attacking desulfurization activity, for example, strains belonging to Pseudomonas sp., *Pseudomonas aeruginosa*, Beijerinckia sp., *Pseudomonas alcaligenes, Pseudomonas stutzeri, Pseudomonas putida*, Brevibacterium sp. are known. These bacteria carry out the cleavage of C—C bond in heterocyclic sulfur compounds of which a representative example is DBT, decompose a benzene ring, thereafter, by oxidative reaction cascade, they conduct a metabolism in which salt containing sulfur atom(s) is released. As the reaction mechanism of the carbon-backbone-attacking pathway, there are the hydroxylation of aromatic ring (DBT→→1,2-dihydroxyDBT), the cleavage of a ring, and the oxidation to water-soluble product (1,2-dihydroxy DBT→→trans-4[2-(3-hydroxy) thianaphthenyl]-2-oxobutenoic acid, 3-hydroxy-2-formylbenzothiophene), and this reaction mechanism is called "Kodama pathway". The C—C bond in a benzene ring of DBT is attacked by this kind of reaction to generate various water-soluble substances which are extractable from the oil. Due to this reaction, however, other aromatic molecules in the oil are also attacked, and as a result, a significant amount of hydrocarbons move to water phase (Hartdegen, F. J., Coburn, J. M. and Roberts, R. L. Chem. Eng. Progress, 80, 63–67(1984)). This causes the reduction of total calories of petroleum and so it is an industrially ineffective reaction. Furthermore, as Kodama et al. has reported, this type of bacteria oxidatively decomposing DBT provides water-soluble thiophene compounds (mainly 3-hydroxy-2-formylbensothiophene) as oxidized products, but this is a substance difficult to remove from water phase. In addition, since the attack to the carbon ring of DBT often occurs at position 2 or 3 of DBT, DBT substituted with an alkyl or alkyl groups at these positions does not become the substrate of the Kodama pathway.

It has been reported that there are microorganisms which decompose not only crude oil or coal but also model compounds containing sulfur, remove. selectively heteroatom sulfur, and generate sulfate and hydroxyl compounds. Taking the structure of the metabolites into consideration, this kind of reaction is considered to be one which cleaves specifically C—S bond in sulfur compounds and accordingly releases sulfur in the form of sulfate. As shown in Table 1, to date, some biodesulfurization reaction systems which are characterized by attacking sulfur have been reported.

Kargi, F., Biotechnol. Lett., 9, 478–482(1987)) and so on. According to Kargi and Robinson (Kargi, F and Robinson, J. M., Appl. Environ. Microbiol., 44, 878–883(1982)), a certain strain of *Sulfolobus acidocaldarius* isolated from an acidic thermal spring of Yellowstone National Park in U.S.A. grows at 45–70° C. and oxidizes elemental sulfur at an optimum pH2. Furthermore, it has been also reported that two other kinds of *Sulfolobus acidocaldarius* stains oxidize pyrite (Tobita, M., Yokozeki, M., Nishikawa, N. & Kawakami, Y., Biosci. Biotech. Biochem. 58, 771–772 (1994)).

It is known that, among the organic sulfur compounds contained in fossil fuel, DBT and its substituted compounds, or derivatives thereof, are generally resistant to hydrodes-

TABLE 1

C-S bond attacking bacteria

| STRAIN | SUBSTRATE | DECOMPOSED PRODUCT | REFERENCE DOCUMENTS |
|---|---|---|---|
| Pseudomonas sp. CB1 | dibenzothiophene; coal | hydroxybiphenyl + sulfate | Isbister et al. (1985) |
| Acinetobacter sp. CB2 | dibenzothiophene | hydroxybiphenyl + sulfate | Isbister et al. (1985) |
| Gram-positive bacteria | coal | sulfate | Crwaford et al. (1990) |
| Rhodococcus rhodochrous IGTS8 (ATCC 53968) | dibenzothiophene coal; petroleum | hydroxybiphenyl + sulfate | Kilbane (1989) |
| Desulfovibrio desulfuricans | dibenzothiophene | biphenyl + hydrogen sulfide | Kim et al. (1990) |
| Corynebacterium sp. | dibenzothiophene | hydroxybiphenyl + sulfate | Omori et al. (1992) |
| Brevibacterium sp. DO | dibenzothiophene | benzoic acid + sulfite | van Afferden et al. (1990) |
| Gram-positive bacterium FE-9 | dibenzothiophene thianthrene | biphenyl + hydrogen sulfide benzene + hydrogen sulfide | Finnerty (1993) |
| Pseudomonas sp. OS1 | benzilmetylsulfide | benzaldehyde | van Afferden (1993) |
| Rhodococcus erythropolis | dibenzothiophene | hydroxybiphenyl | Wang et al. (1994) |
| Rhodococcus erydtropolis D-1, H-2 | dibenzothiophene | hydroxybiphenyl | Izumi et al. (1994)., Ohshiro et al. (1995) |
| Agrobacterium sp. | dibenzothiophene | hydroxybiphenyl | Constantl et al. (1994) |
| Xanthomonas sp. | dibenzothiophene | hydroxybiphenyl | Constantl et al. (1994) |
| Arthrobacter K3b | dibenzothiophenesulfone | benzoic acid + sulfite | Dahlberg (1992) |

For all biodesulfurizations stated above, a metabolic reaction of microorganism cultured at around 30° C. is used. On the other hand, it is known that generally the rate of chemical reaction increases as the temperature becomes higher. Regarding the desulfurization in petroleum refining process, fractional distillation or desulfurization reaction is carried out under conditions of high temperature and high pressure. Therefore, when biodesulfurization is incorporated into the petroleum refining process, it is desirable that the desulfurization reaction is carried out at higher temperature in the mid course of cooling process, without cooling the fraction to room temperature. Some reports on high-temperature biodesulfurization are as follows.

Most attempts to carry out the desulfurization reaction using microorganisms at room temperature are directed to coal desulfurization. Coal contains various kinds of sulfur compounds. The main inorganic sulfur compound is pyrite. On the other hand, the organic sulfur compounds vary widely in type, and it is known that the majority of these contain thiol, sulfide, disulfide and thiophene groups. The microorganisms used are Sulfolobus bacteria which are all thermnophiles. There are several reports that various Sulfolobus strains were used in the leaching of metal out of mineral sulfide (Brierley C. L. & Murr, L. E., Science 179, 448–490(1973)), the desulfurization of pyrite in coal (Kargi, F. & Robinson, J. M., Biotechnol. Bioeng, 24, 2115–2121 (1982); Kargi, F. & Robinson, J. M., Appl. Environ. Microbiol., 44, 878–883(1982); Kargi, F. & Cervoni, T. D., Biotechnol. Letters 5, 33–38(1983); Kargi, F. and Robinson, J. M., Biotechnol. Bioeng., 26, 687–690(1984); Kargi, F. & Robinson, J. M., Biotechnol. Bioeng. 27, 41–49(1985);

ulfurization in the petroleum refining process. High-temperature decomposition by *Sulfolobus acidocaldarius* (hereinafter, referred to as "*S. acidocaldarius*") of the said DBT has been also reported (Kargi, & Robinson, J. M., Biotechnol. Bioeng, 26, 687–690(1984); Kargi, F., Biotechnol. Letters 9, 478–482(1987)).

According to these reports, when model aromatic heterocyclic sulfur compounds such as thianthrene, thioxanthene, DBT and the like are reacted with *S. acidocaldarius* at high temperature, these sulfur compounds are oxidized and decomposed. Oxidation of these aromatic heterocyclic sulfur compounds by this microorganism is observed at 70° C. and it results in the formation of sulfate ions as the reaction product. However, because this reaction is carried out in a medium which does not contain any carbon source other than sulfur compounds, these sulfur compounds would be also used as the carbon sources. That is to say, it is clear that C—C bond in sulfur compounds was decomposed. Furthermore, *S. acidocaldarius* can be grown only in an acidic medium, and the oxidative decomposition reaction require under severely acidic conditions (e.g. pH2.5) to continue. Since such conditions cause the degradation of petroleum products and at the same time requires acid-resistant materials in the desulfurization-associated step, it is considered not to be desirable for the process. When *S. acidocaldarius* is grown under autotrophic conditions, the microorganism acquires necessary energy from reduced iron-sulfur compounds and uses carbon dioxide as the carbon source. Alternatively, when *S. acidocaldarius* is grown under heterotrophic conditions, it can use various organic compounds as carbon and energy sources. In other words, it can be said when fossil fuel exists, it can be used as a carbon source.

Finnerty et al. has reported that the strains belonging to *Pseudoinonas stutzeri, Pseudomnonas alcaligenes* and *Pseudomonas putida* decompose DBT, benzothiophene, thioxanthene and thianthrene, and convert them into water-soluble substances (Finnerty, W. R., Shockiey, K., Attaway, H. in *Microbial Enhanced Oil Recovery*, Zajic, J. E. et al.(eds.) *Penwell. Tuisa, Okia*, 83–91(1983)). In this case, the oxidative reaction can proceed at 55° C. However, the decomposed products of DBT by these Pseudonionas strains are 3-hydroxy-2-formylbenzothiophene reported by Kodama et al. (Monticello, D. J., Bakker, D., Finnerty, W. R. *Appl. Environ. Microbiol.*, 49, 756–760(1985)). The oxidation activity of DBT by the Pseudomonas strains is induced by an aromatic hydrocarbon without sulfur such as naphthalene or salicylic acid, and is blocked by chloramphenicol. From this fact, it was found that the decomposition reaction of DBT by the Pseudomonas strains is based on the cleavage of a C—C bond in aromatic ring. Moreover, there is the risk that valuable aromatic hydrocarbons other than sulfur compounds in the petroleum fraction are also decomposed together with them, and if this occurs, it results in lowering of fuel value or petroleum fraction quality.

As stated above, the known strains which can decompose DBT at high temperature are the ones which catalyze the reaction of cleaving a C—C bond in the DBT molecule and use the resulting compounds as carbon sources. As mentioned above, the decomposition reaction of organic sulfur compounds which cleaves specifically C—S bond but leaves C—C bond unchangeable is desirable as a real method for desulfurizing petroleum. In other words, the most desirable biodesulfurization process is one which has an activity of cleaving C—S bond in the molecule of DBT and its alkyl-substituted compounds, or their derivatives at high temperature and uses microorganisms which generate desulfurization products in the form of water-soluble substances.

As stated above, several families of bacteria are known as microorganisms conducting the C—S bond cleavage to decompose DBT. However, of all these bacteria, there were found no examples described to have an activity of decomposing DBT under high temperature conditions of more than 42° C. For example, ATCC53968 (Rhodococcus sp). is a thoroughly studied DBT-decomposing strain and conducts an addition of an oxygen atom to the sulfur atom of DBT, generating DBT sulfone (hereinafter referred to as "DBTO2") from DBT sulfoxide (hereinafter referred to as "DBTO"), and further generating 2-hydroxybiphenyl (hereinafter referred to as "2-HBP") via 2-(2'-hydroxyphenyl) benzensulfinate. However, it has been reported that even this strain grows very slowly or stops growing, when it is cultured for 48 hours at a temperature of 37° C. or 43° C. which is slightly higher than 30° C. (an ordinary culturing temperature) (Japanese Patent Application Laying-Open (kokai) No. 6-54695). Therefore, it has been presumed that the use of the microorganism, which can grow under high temperatures condition and can cleave specifically the C—S bond of heterocyclic sulfur compounds including organic sulfur compounds, especially DBT, its substituted compounds, or their derivatives at high temperature, is more suitable for conducting the desulfurization reaction at high temperature. The present inventors have conducted a wide range of screenings, has amplified the microorganisms under high temperature conditions, nearly 60° C., and has already isolated 2 strains of Paenibacillus sp., which are high-temperature desulfurizing strains having a function of decomposing and desulfurizing DBT families for the first time in the world (Japanese Patent Application Laying-Open (kokai) No. 10-036859). If genes which are associated with high-temperature desulfurization activity can be isolated from this strain, it is possible to endow a wide range of microbes with the function of high-temperature desulfurization by using genetic engineering such as recombinant DNA technology.

Among the bacteria known for their function of conducting C—S bond cleavages in the decomposition reaction, genes thereof, which encode enzyme activities involved in DBT decomposition reaction that are identified and whose nucleotide sequences are determined are, to the best of the present inventors' knowledge, only dsz genes of Rhodococcus sp. IGTS8 strain (Denome, S., Oldfield., C., Nash, L. J. and Young, K. D. J. Bacteriol., 176:6707–6716, 1994; Piddington, C. S., Kovacevich, B. R. and Rambosek, J. Appl. Environ. Microbiol., 61:468–475, 1995). The DBT decomposition reaction by IGTS8 strain is catalyzed by three enzymes: DszC catalyzing the conversion from DBT to DBTO2 via DBTO, DszA catalyzing the conversion from DBTO2 to 2-(2'-hydroxyphenyl) benzensulfinic acid, and DszB catalyzing the conversion from 2-(2'-hydroxyphenyl) benzensulfinic acid to 2-HBP (Denome, S., Oldfield., C., Nash, L. J. and Young, K. D. J. Bacteriol., 176:6707–6716, 1994; Gray, K. A., Pogrebinshy, O.S., Mrachko, G. T., Xi, L. Monticello, D. J. and Squires, C. H. Nat Biotechnol., 14:1705–1709, 1996; Oldfield, C., Pogrebinsky, O., Simmonds, J., Olson, E. S. and Kulpa, C. F., Microbiology, 143:2961–2973, 1997). The genes corresponding to the above enzymes are called dszA, dszB and dszC. It is known that the enzymes DszC and DszA are monooxygenases, and both enzymes need the coexistence of NADH-FMN oxidoreductase activity for their oxygenation reaction (Gray, K. A., Pogrebinsky, O. S., Mrachko, G. T., Xi, L. Monticello, D. J. and Squires, C. H. Nat Biotechnol., 14:1705–1709, 1996; Xi, L. Squires, C. H., Monticello, D. J. and Childs, J. D. Biochem. Biophys. Res Commun., 230:73–76, 1997) It has been reported that when the dsz genes are induced and expressed in *Escherichia coli* by shifting the temperature, DszA activity by cell culture reaches the maximum at 39° C., but remarkably decreases at 42° C. (Denome, S., Oldfield., D., Nash, L. J. and Young, K. D. J. Bacteriol., 176:6707–6716, 1994). This report corresponds to the result of an experiment on resting cell reaction system which shows that the desulfurization enzyme activity of IGTS8 strain reaches the maximum around room temperature, but activity decreases at higher temperature and there is no desulfurization activity at temperatures of more than 50° C. (Konishi, J., Ishii, Y., Onaka, T., Okumura, K. and Suzuki, M. Appl. Environ. Microbiol., 63:3164–3169, 1997). Therefore, the genes which direct DBT-decomposing activity specific for C—S bond under high temperature conditions, more than 50° C., have not been previously reported.

Objects to be Achieved by the Invention

One object of the present invention is to isolate the genes involved in high-temperature desulfurization reaction from a microorganism having an ability of acting on benzothiophene and DBT compounds and decomposing them at high temperature, to specify the structure (especially the nucleotide sequences), and to create novel desulfuirizting microorganisms by introducing the genes into a heterologous microorganism and endowing it with the ability of desulfurization. Another object of the present invention is to establish a method for removing sulfur by actually contacting such a microorganism with benzothiophene, DBT and their alkyl derivatives and cleaving the C—S bonds of these compounds.

Means to Achieve the Objects

After thorough studies directed to achieve the above objects, the present inventors have succeeded in isolating the genes involved in desulfurization reaction from high-temperature desulfurization bacteria, Paenibacillus sp., and have completed the present invention.

That is to say, the first aspect of the present invention relates to genes encoding desulfurization enzymes.

The second aspect of the present invention relates to vectors containing the said genes.

The third aspect of the present invention relates to transformants containing the said vectors.

The forth aspect of the present invention relates to desulfurization enzymes.

The fifth aspect of the present invention relates to genes encoding transposase.

The sixth aspect of the present invention relates to transposase.

This specification includes part or all of the contents as disclosed in the specifications and/or drawings of Japanese Patent Application Nos. 10-090387 and 10-310545 which are priority documents of the present application.

Disclosure of the Invention

The details of the present invention are disclosed below.

(1) Gene Encoding a Desulfurization Enzyme

The genes of the present invention comprise the following three types of genes.

The first gene encodes (a) a protein represented by an amino acid sequence shown in SEQ ID NO: 2; or (b) a protein comprising a deletion, substitution or addition of one or more amino acids in the amino acid sequence of SEQ ID NO: 2, and having a function of converting DBTO2 into 2-(2'-hydroxyphenyl) benzenesulfinic acid.

The second gene encodes (a) a protein represented by an amino acid sequence shown in SEQ ID NO: 4; or (b) a protein comprising a deletion, substitution or addition of one or more amino acids in the amino acid sequence of SEQ ID NO: 4, and having a function of converting 2-(2'-hydroxyphenyl) benzenesulfinic acid into 2-HBP.

The third gene encodes (a) a protein represented by an amino acid sequence shown in SEQ ID NO: 6; or (b) a protein comprising a deletion, substitution or addition of one or more amino acids in the amino acid sequence of SEQ ID NO: 6, and having a function of converting DBT into DBTO2 via DBTO.

The above-described first, second and third genes have a certain homology to dszA, dszB or dszC derived from Rhodococcus sp. IGTS8 strain. However, the proteins encoded by these genes are different from the ones encoded by dszA, dszB and dszC in terms of their properties.

Among the genes of the present invention, the ones which encode amino acid sequences as shown in SEQ ID NOS: 2, 4 and 6 can be obtained by the methods described later in Examples. Since the nucleotide sequences of these genes have been already determined as shown in SEQ ID NOS: 1, 3 and 5, they can also be obtained by synthesizing primers on the basis of these nucleotide sequences, and carrying out PCR using the primers and a DNA as a template, the DNA being prepared from Paenibacillus sp. A11-1 strain (which was deposited with the National Institute of Bioscience and Human-Technology, Agency of Industrial Science and Technology under accession No. FERM BP-6025 on Jul. 22, 1997) or A11-2 strain (which was deposited with the same international depositary authority under accession No. FERM BP-6026 on Jul. 22, 1997).

The genes encoding amino acid sequences comprising a deletion, substitution or addition of one or more amino acids in the amino acid sequence of SEQ ID NOS: 2, 4 and 6 can be obtained by modifying the genes encoding amino acid sequences shown in SEQ ID NOS: 2, 4 and 6, by techniques in common use at the time of the filing date of the present application, for example site-directed mutagenesis (Zoller et al., *Nucleic Acids Res.* 10: 6487–6500, 1982.

Since the genes of the present invention encode enzymes which are associated with the decomposition of DBT, they can be used to desulfurize petroleum.

(2) Vector Comprising a Gene which Encodes a Desulfurization Enzyme

The vector of the present invention comprises the above-described first, second or third gene. Such a vector can be prepared by inserting a DNA fragment containing the first, second or third gene of the present invention into a known vector. The vector into which the DNA fragment is inserted is determined depending on the type of host being transformed. If *Escherichia coli* is used as the host, the following vector can preferably be used. It is preferable to use vectors such as pUR, pGEX, pUC, pET, pT7, pBluescript, pKK, pBS, pBC, pCAL and the like, which carry lac, lacUV5, trp, tac, trc, $\lambda$pL, T7, rrnB or the like as a strong promoter.

(3) Transformant Comprising a Vector Containing Genes which Encode a Desulfurization Enzyme The transformant of the present invention comprises a said vector. The cells used as a transformation host may be from a plant or animal, but microorganisms such as *Escherichia coli* are more preferable. Typical strains include, for example, 71/18, BB4, BHB2668, BHB2690, BL21(DE3), BNN102(C600hflA), C-1a, C600(BNN93), CES200, CES201, CJ236, CSH18, DH1, DH5, DH5 α, DP50supF, ED8654, ED8767, HB101, HMS174, JM101, JM105, JM107, JM109, JM110, K802, KK2186, LE392, LG90, M5219, MBM7014.5, MC1061, MM294, MV1184, MV1193, MZ-1, NM531, NM538, NM539, Q358, Q359, R594, RB791, RR1, SMR10, TAP90, TG1, TG2, XL1-Blue, XS101, XS127, Y1089, Y1090hsdR, YK537, and the like, which are all described in Sambrook et al., *Molecular Cloning A Laboratory Manual* 2nd ed.

(4) Desulfurization Enzyme

The desulfurization enzymes of the present invention includes the following three proteins.

The first protein is a protein represented by an amino acid sequence shown in SEQ ID NO: 2, or a protein comprising a deletion, substitution or addition of one or more amino acids in the amino acid sequence shown in SEQ ID NO: 2, and having a function of converting DBTO2 into 2-(2'-hydroxyphenyl) benzenesulfinic acid.

The second protein is a protein represented by an amino acid sequence shown in SEQ ID NO: 4, or a protein comprising a deletion, substitution or addition of one or more amnino acids in the amnino acid sequence shown in SEQ ID NO: 4, and having a function of converting 2-(2'-hydroxyphenyl) benzenesulfinic acid into 2-HBP.

The third protein is a protein represented by an amino acid sequence shown in SEQ ID NO: 6, or a protein comprising a deletion, substitution or addition of one or more amnino acids in the amnino acid sequence shown in SEQ ID NO: 6, and having a function of converting DBT into DBTO2.

The said first, second and third proteins have a certain homology to the desulfurization enzyme DszA, DszB or DszC derived from Rhodococcus sp. IGTS8 strain, and their function as an enzyme is also identical. However, they are apparently distinct in respect of the following.

(1) DszA, DszB and DszC cannot desulfurize benzothiophene which is a desulfurization-resistant substance, but the first, second and third proteins of the present invention can do so.
(2) DszA, DszB and DszC have the desulfurization activity at around room-temperature region, but the first, second and third proteins have activity at a high-temperature region.

The desulfurization enzymes of the present invention can be prepared by using the genes encoding the said desulfurization enzymes of the present invention. Further, the desulfurization enzymes represented by amino acid sequences as shown in SEQ ID NOS: 2, 4 and 6 can also be prepared from the strains Paenibacillus sp. A11-1 (which was deposited with the National Institute of Bioscience and Human-Technology, Agency of Industrial Science and Technology under accession No. FERM BP-6025 on Jul. 22, 1997) or Paenibacillus sp. A11-2 (which was deposited with the same international depositary authority under accession No. FERM BP-6026 on Jul. 22, 1997) according to the conventional methods.

The characteristics of one example of the first protein of the present invention are as follows:

(i) Function: the first protein converts DBTO2 into 2-(2'-hydroxyphenyl) benzenesulfinic acid;
(ii) pH: as shown in FIG. 6, optimum pH: 5.5, stable pH: 5–10;
(iii) Temperature: as shown in FIG. 7, optimum temperature: 45° C.;
(iv) Molecular weight: 120,000 (as determined by gel filtration);
(v) Inhibition of activity: the first protein is inhibited by chelating agents or SH inhibitors, but not by 2-HBP or sulfate; and
(vi) Requirement for coenzyme: NADH and FMN are required, NADPH can be substituted for NADH, but FAD cannot be substituted for FMN.

The characteristics of one example of the second protein of the present invention are as follows:

(i) Function: the second protein converts 2-(2'-hydroxyphenyl) benzenesulfinic acid into 2-HBP;
(ii) pH: as shown in FIG. 8, optimum pH: 8, stable pH: 5.5–9.5;
(iii) Temperature: as shown in FIG. 9, optimum temperature: 55° C.;
(iv) Molecular weight: 31,000 (as determined by gel filtration)
(v) Inhibition of activity: the second protein is inhibited by chelating agents or SH inhibitors, but not by 2-HBP or sulfate; and
(vi) Requirement for coenzyme: no coenzyme is required.

(5) Gene Encoding Transposase

The transposase genes of the present invention encodes any of the following proteins:

(a) a protein represented by an amino acid sequence as shown in SEQ ID NO: 8,
(b) a protein represented by an amino acid sequence as shown in SEQ ID NO: 9, or
(c) a protein comprising a deletion, substitution or addition of one or more amino acids in the amino acid sequence shown in SEQ ID NO: 8 or SEQ ID NO: 9, and having a transposase activity.

Among the transposase genes of the present invention, the ones encoding amino acid sequences set forth in SEQ ID NOS: 8 and 9 have been determined, as shown in SEQ ID NO: 7. So such genes can also be obtained by synthesizing appropriate primers on the basis of the determined sequence and carrying out PCR using, as a template, DNA prepared from Paeniibacillus sp. A11-1 strain (which was deposited with the National Institute of Bioscience and Human-Technology, Agency of Industrial Science and Technology under accession No. FERM BP-6025 on Jul. 22, 1997) or A 11-2 strain (which was deposited with the same international depositary authority under accession No. FERM BP-6026 on Jul. 22, 1997).

The gene encoding an amino acid sequence comprising a deletion, substitution or addition of one or more amino acids in the amino acid sequence of SEQ ID NO: 8 or NO: 9 can be obtained by modifying the genes which encode an amino acid sequence shown in SEQ ID NO: 8 or NO: 9, according to the conventional art as of the filing date of the present application, e.g. site-directed mutagenesis (Zoller et al., *Nucleic Acids Res.* 10: 6487–6500, 1982)

Since this gene has transposase activity, it is possible to transfer any gene unit from a certain DNA molecule to a different DNA molecule by using this gene. By the way, it has not experimentally been determined that the polypeptide represented by an anino acid sequence as shown in SEQ ID NO: 8 or NO: 9 has transposase activity. However, there seems to be an extremely high possibility that each of the two polypeptide has transposase activity for the reasons that they have a certain homology to transposase existing in an insertion sequence IS1202, that ORFs of two polypeptides are in the reverse orientation to ORFs of desulfurization enzymes and are in a position directed to sandwich them (a structure specific for transposon), and that the direct repeat sequence (DR) and the invert repeat sequence (IR) which are specific for transposon exist at each end of SEQ ID NOS: 8 or 9.

(6) Transposase

The transposase of the present invention is selected from the group consisting of:

(a) a protein represented by the amino acid sequence as shown SEQ ID NO: 8,
(b) a protein represented by the amino acid sequence as shown SEQ ID NO: 9, and
(c) a protein comprising a deletion, substitution or addition of one or more amino acids in the amino acid sequence shown in SEQ ID NO: 8 or SEQ ID NO: 9, and having a transposase activity.

The transposase of the present invention can be prepared by using the genes encoding the above-described transposase.

EXAMPLES

The present invention will be illustrated in more detail by the examples described below.

The experiments related to genetic engineering in the examples were carried out mainly according to the methods described in Sambrook, J., Fritsch, E., F. and Maniatis, T. (1989). *Molecular Cloning. A laboratory Manual*, 2nd ed., Cold Spring Harbor Laboratory Press, Cold Spring Harbor, N.Y.

Example 1

Cloning of the Gene Fragment Encoding Desulfurization Enzyme

The amino acid sequences of the amino termini of both a protein having an activity which converts DBTO2 into 2-(2'-hydroxyphenyl) benzensulfinic acid (called "protein A" hereinafter) and a protein having an activity which converts 2-(2'-hydroxyphenyl) benzensulfinic acid into 2-HBP (called "protein B" hereinafter), purified from Paenibacillus sp. A11-2 strain, were determined. The sequences are as follows.

```
Protein A NH2-MXQMXLAGFFAAGNVTXXXGA-----COOH (SEQ ID NO:10)

Protein B NH2-TKSAIGPTRVAYSNXPVANXL-----COOH (SEQ ID NO:11)
(Amino acids are expressed as a one-letter symbol. X means not yet identified.)
```

A homology was found between the amino acid terminal sequences of these two proteins and the ones of DszA and DszB proteins encoded by dsz operon of the mesophile desulfurization bacterium, Rhodococcus sp. IGTS8 strain.

```
Paenibacillus sp. A11-2 strain   Protein A    MXQMXLAGFFAAGNVTXXXGA (SEQ ID NO:10)

Rhodococcus sp. IGTS8 strain     DszA         MTQQTQMHAGFFSAGNVTHAHGA (SEQ ID NO:12)

Paenibacillus sp. A11-2 strain   Protein B    TKSAIGPTRVAYSNXPVANXL (SEQ ID NO:11)

Rhodococcus sp. IGTS8 strain     DszB         GSELDSAIRDT-LTYSNCPVPNAL (SEQ ID NO:13)
```

Regarding Rhodococcus sp. IGTS8 strain, it is known that the 3'-terminus of the coding sequence of dszA overlaps the 5'-terminus of dszB, and dsz A and dsz B are translated in different frames. Regarding the gene sequence encoding the enzymes associated with the desulfurization of DBT, it is presumed that there is some similarity between Paenibacillus sp. A11-2 strain and Rhodococcus sp. IGTS8 strain. Hence, using a coding strand of the 5'-terminal side sequence of dszA which is expected to be upstream as a sense strand and a complementary strand of the 5'-terminal side sequence of dszB which is expected to be downstream as an antisense strand, firstly amplification of a DNA fragment containing the entire dszA was attempted.

First of all, according to the above amino acid sequences, a total of four kinds of sense primers corresponding to the amino terminal sequences of protein A and a total of four kinds of antisense primers corresponding to the amino terminal sequences of protein B were designed and synthesized. The nucleotide sequences of all the primers are as follows.
Sense primers:

```
DSZA-MIX  5'-GGN TTY TTY GCN GCN GGN AAY GTN AC-3'
          (SEQ ID NO:14)

THDSA-SM3 5'-TTY GCN GCN GGN AAY GT-3'
          (SEQ ID NO:15)

THDSA-SM4 5'-TTY TTY GCN GCN GGN AA-3'
          (SEQ ID NO:16)

THDSA-SM5 5'-GCN GGN TTY TTY GCN GC-3'
          (SEQ ID NO:17)
```

Antisense primers:

```
THDSB-AM2 5'-TAN GCN ACY CTN GTN GGN CCD ATN GC-3'
          (SEQ ID NO:18)

THDSB-AM3 5'-TAN GCN ACY CTN GTN GG-3'
          (SEQ ID NO:19)

THDSB-AM4 5'-TCR TTN ACN GCN GTY TC-3'
          (SEQ ID NO:20)

THDSB-AM5 5'-ACY CTN GTN GGN CCD AT-3'
          (SEQ ID NO:21)
```

After combining the sense primers with the antisense primers in different sets, PCR was carried out, using the DNA extracted from Paenibacillus sp. A11-2 strain as a template. The preparation of DNA from Paenibacillus sp. A11-2 strain was carried out as follows. Paenibacillus sp. A11-2 strain cultured in medium A containing DBT (regarding the composition, see the table set forth below) for 24 hours at 50° C. was cultured in medium A containing fresh DBT for 24 hours at 50° C. to collect the cultured cells. The obtained cells were suspended in 1 ml of B1 buffer (50 mM EDTA, 50 mM Tris-HCl, 0.5% Triton X-100, 0.2 mg/ml RNaseA, pH 8.0). To this suspension, 20 µl of lysozyme solution (100 mg/ml) and 45 µl of Proteinase K solution (20 mg/ml) were added, and the suspension was reacted for 10 minutes at 37° C. After adding 0.35 ml of B2 buffer (800 mM guanidine hydrochloride, 20% Tween-20, pH 5.5), the reaction solution was mixed with the buffer while stirring, reacted for 30 minutes at 50° C., stirred by a mixer for 5 seconds to prepare the reaction solution of the cells. After a negative ion-exchange resin-filled QIAGEN GENOMIC-TIP20/G column (QIAGEN) was equilibrated with 2 ml of QBT buffer (750 mM NaCl, 50 mM MOPS, 15% ethanol, 0.15% Triton X-100, pH 7.0), the reaction solution of the cells was applied to the column. After washing the column with 3 ml of QC buffer (1.0M NaCl, 50 mL MOPS, 15% ethanol, pH 7.0), the genomic DNA was eluted with 2 ml of QF buffer (1.25M NaCl, 50 mL Tris-HCl, 15% ethanol, pH 8.5). After 1.4 ml of isopropanol was added to the genomic DNA solution to precipitate DNA, the obtained DNA was collected by winding around a glass rod. The collected DNA was dissolved in 50 µl of TE buffer (10 mM Tris-HCl, 1 mM EDTA, pH 8.0) to prepare a genomic DNA solution.

TABLE 2

Composition of medium A:

| | |
|---|---|
| Glucose | 5.0 g |
| $KH_2PO_4$ | 0.5 g |
| $K_2HPO_4$ | 4.0 g |
| $NH_4Cl$ | 1.0 g |
| $MgCl_2.6H_2O$ | 0.1 g |
| NaCl | 0.01 g |
| $CaCl_2$ | 0.02 g |
| Metal solution | 10 ml |
| Vitamins mix | 1 ml |
| Distilled water | to 1 L |
| pH 7.5 | |
| Metal solution | |
| $FeCl_2.4H_2O$ | 0.5 g |
| $ZnCl_2$ | 0.5 g |
| $MnCl_2.4H_2O$ | 0.5 g |
| $CuCl_2$ | 0.05 g |
| $Na_2MoO_4.2H_2O$ | 0.1 g |
| $Na_2WO_4.2H_2O$ | 0.05 g |
| Conc. HCl | 10 ml |
| Distilled water | to 1 L |
| Vitamins mix | |
| Calcium pantothenate | 400 mg |
| Inositol | 200 mg |
| Niacin | 400 mg |
| p-aminobenzoate | 200 mg |
| pyridoxine-HCl | 400 mg |
| vitamin$B_{12}$ | 0.5 mg |
| Distilled water | to 1 L |

The conditions of PCR wherein the prepared DNA of Paenibacillus sp. A 11-2 strain was used as a template are as follows.
Compositions of the reaction solution:

| | |
|---|---|
| 50 mM | KCl |
| 1.5 mM | $MgCl_2$ |
| 0.2 mM each | dNTP Mixture |
| 0.2 μM | Sense primer |
| 0.2 μM | Antisense primer |
| 200 ng | Template DNA |
| 2.5 U | Taq DNA polymerase |

Annealing temperature: PCR was carried out varying temperatures in two degrees intervals from 44° C. to 66° C.

| PCR cycle: | 95° C. | 1 min | once |
|---|---|---|---|
| | 95° C. | 1 min | ↓ |
| | 44–66° C. | 1 min | repeated for 30 cycles |
| | 72° C. | 5 min | ↑ |
| | 72° C. | 7 min | once |

DNA amplifier: Robocycler™ GRADIENT96 Temperature Cycler (STRATAGENE)

As a result of the PCR under the above conditions, it was determined that an amplified fragment of approximately 1.6 kb is obtained by several combinations of primers, when the annealing temperature is 44–50° C. This 1.6 kb PCR product was cloned into *Escherichia coli* XL1-Blue MRF-Kan strain by using pCR-Script SK(+) vector. By sequencing a part of the cloned DNA fragment, it was found that the 1.6 kb DNA fragment contains nucleotide sequences which can encode amino acid sequences of the amino termini of the purified protein A and protein B. However, the sequence of the amplified DNA fragment contains a sequence which is further downstream of the nucleotide sequence encoding amino terminus of protein B, which corresponds to the nucleotide sequence used as an antisense primer. By analyzing the determined nucleotide sequence, it was found that the 3'-termninal side sequence consists of a complementary nucleotide sequence to the sense primer corresponding to the amino terminal sequence of protein A. Thus, it was confirmed that the 1.6 kb DNA fragment was amplified as a result of annealing the sense primer corresponding to the amino terminus sequence of protein A with the nucleotide sequence downstream of the Inucleotide sequence encoding the amino terminal sequence of protein B; the sense primer acted as an antisense primer.

After deducing an amino acid sequence encoded by the determined DNA sequence, this sequence was compared with each amino terminal sequence of DszA and DszB among the proteins encoded by dsz genes cloned from Rhodococcus sp. IGTS8 strain. As a result, it was determined that the deduced sequence has a significant homology with both DszA and DszB sequences (respectively 73%, 61%). Since the homology with dsz operon DNA sequence for desulfurization genes of Rhodococcus sp. IGTS8 was found, we tried to further clone another DNA sequence adjacent to the DNA sequence cloned from Paenibacillus sp. A 11-2 strain, using that DNA sequence as a probe.

Example 2

Preparation of the Total DNA Library

The method for preparing the total DNA is the same as the one for the DNA used as a template in PCR.
Method for Preparing the Library
The total DNA library from Paenibacillus sp. A 11-2 strain was prepared as follows. Approx. 2 μg of the total DNA sample of Paenibacillus sp. A11-2 strain was digested with 0.1 unit of Sau3AI for respectively 20, 30 and 40 minutes, extracted with phenol-chloroform, and precipitated with ethanol to yield the digest. After centrifuging, the obtained DNA fragment was treated with 8 units of alkaline phosphatase derived from calf small intestine for 60 minutes at 37° C. to remove phosphoric acid. After treating with alkaline phosphatase, DNA was extracted with phenol-chloroform, and precipitated with ethanol to yield the precipitate. Approx. 0.2 μg of the obtained DNA fragment was reacted with approx. 2μg of λ DASHII/BamHI arm in the presence of 2 units of T4 DNA ligase for 18 hours at 4° C. In vitro packaging was carried out by reacting the mixture with Gigapack II XL packaging Extract to prepare a phage library. After packaging, the titer of the phage suspension was $2\times10^6$ pfu.

Example 3

Screening of the Total DNA Library

A DNA probe used for the screening of phage library was prepared as follows. As described in Example 1, there is homology between the nucleotide sequence of DNA of Paenibacillus sp. A 11-2 strain, which is considered to encode protein A having an activity of converting DBTO2 into 2-(2'-hydroxyphenyl) benzensulfinic acid and protein B having an activity of converting 2-(2'-hydroxyphenyl) benzensulfinic acid into 2-HBP, and dsz gene sequence of Rhodococcus sp. IGTS8 strain. Selecting 5' terminal side sequence of dszA of Rhodococcus sp. IGTS8 strain (from $120^{th}$ nucleotide to $137^{th}$ nucleotide), whose homology is relatively high, as a sense strand, and selecting a complementary strand to the sequence from $169^{th}$ nucleotide to $185^{th}$ nucleotide of 5' terminal of dszB coding sequence as an antisense strand, PCR primers were prepared. By carrying out PCR with these primers and with the DNA prepared from Paenibacillus sp. A 11-2 strain as a template, the sequence of the region encoding protein A was amplified. Using the obtained PCR product as a template, DSZA probe labeled with dioxygenin (DIG) was prepared by the random-prime (multi-prime) method. The preparation of DIG-labeled probe was carried out according to the protocol of Boehringer Mannheim. The method for preparing DIG-labeled probe is shown below.

1 μg (5 μl) of the obtained PCR product was denatured in boiled water for 10 minutes, then cooled on ice containing salt. To the obtained denatured DNA solution, 10 μl of hexanucleotide mixed solution (0.5M Tris-HCl, 0.1M MgCl$_2$, 1 mM Dithioerythriol, 2 mg/ml BSA, 3.143 mg/ml Random Primer, pH 7.2 ), 10 μl of dNTP label mixed solution (1 mM dATP, 1 mM dCTP, 1 mM dGTP, 0.65 mM dTTP, 0.35 mM DIG-dUTP, pH7.5 ), 70 μl of sterile distilled water and 5 μl of Klenow enzyme (10 units) were added, then reacted for 18 hours at 37° C. 5 μl of 0.5M EDTA solution was added to the reaction mixture to stop the reaction. Then, 5 μl of 8M LiCl and 275 μl of cold ethanol (−20° C.) were added, left for 30 minutes at −80° C., and centrifuged for 30 minutes at 15,000 rpm to precipitate DNA. The precipitated DNA was washed with cold 70% (w/v) ethanol and dried aspiration, then it was dissolved in 50 μl of TE buffer to yield a DIG labeled probe.

The screening of protein A gene was carried out by plaque hybridization to the plaque transferred to Hybond N+ membrane, using the DIG labeled probe prepared by the above-described method. To detect the hybridized clone, DIG-ELISA (Boehringer Mannheim) was used. Screening approx. 2,000 phage plaques out of the genomic library by using DSZA probe, 6 positive plaques were detected. These 6 plaques were subjected to single plaque separation followed by the plaque hybridization once again, whereby 4 positive plaques were detected. Phage clones were prepared by using the detected DSZA probe positive plaques, then phage DNA was extracted from those clones by using QIAGEN Lambda kit. The phage DNA prepared with 4 positive plaques was cleaved with EcoRI, NotI, HindIII and SalI to create a restriction enzyme map as shown in FIG. 1. Furthermore, using the DSZA probe, Southern blot analysis was carried out for the DNA obtained by digesting 4 kinds of phage DNAs with EcoRI, NotI, SalI, or NotI and SalI. As a result, it was confirmed that No. 2 and No. 4 clones were hybridized to approx. 2 kb of NotI-SalI fragment. However, regarding No. 3 and No. 6 clones, no hybridization was observed. Based on the results of the restriction enzyme map and Southern blot analysis, it was considered that approx. 6 kb deletion and recombination occurred in No. 3 and No. 6 phage DNAs and that dsz genes were encoded in an approx. 8.7 kb EcoRI-HindIII fragment of No. 4 phage DNA. To examine the ability to decompose DBT of *Escherichia coli* having each of the subcloned DNAs, the following culture was carried out. *Escherichia coli* XL1-Blue having sub-cloned DNAs was cultured for a week at 37° C. in the medium prepared by adding 50 μg of yeast extract to M9 medium (Sambrook et al., *Molecular cloning A Laboratory Manual 2$^{nd}$*), followed by adding DBT, DBTO2, sodium sulfate or the like as a sulfur source. As a control strain, XL1 Blue strain having only vector pBluescript II KS(+) was subcultured under the same conditions. Preculturing was performed in LB medium (described in the said reference, Sambrook et al., *Molecular cloning A Laboratory Manual 2$^{nd}$*) overnight at 37° C. The cells were collected by centrifuging the obtained preculture broth, then washed with 66 mM of phosphate buffer, and suspended in M9 modified medium (in which sulfate in the M9 medium was substituted by chloride). The cell suspension 1/100 volume was added to an assay medium (prepared by adding DBT or DBTO2 as a sulfur source to M9 modified medium), the mixture was cultured for 48 hours at 37° C. Then, the decomposition product was extracted in accordance with standard techniques, and gas chromatography was carried out on the product. As a result, it was determined that regarding No. 4 clone, 2-HBP was generated when the No. 4 clone was cultured in the medium containing DBT or DBO2 as sole sulfur source. However, the host XL1 Blue strain did not have such convertion activity at all. Therefore, it was proved that the cloning DNA of No. 4 clone has a sequence which can encode the entire activity of catalyzing the conversion reaction of DBT into 2-HBP.

Next, in order to determine the nucleotide sequence of the entire cloned DNA derived from the Paenibacillus sp. A11-2 strain, a series of deletion DNAs was prepared. Approx. 0.2 μg of DNA prepared from the DSZA probe positive phage clone No. 4 was double-digested using EcoRI and HindIII, and the generated double digest was electrophoresed to purify the approx. 8.7 kb insertion DNA fragment. After ligating this fragment to the double digest which was obtained by treating pBluescript II KS (+) with EcoRI and HindIII and then dephosphorylated, Escherichia coli XL1 Blue strain was transformed by using the obtained hybrid DNA. Restriction enzyme analysis was. carried out for the obtained subclone (p4EM), and it was determined that restriction sites KpnI and SacI did not exist in the insertion fragment. So, to prepare a deletion plasmnid used for sequencing of this insertion fragment, a combination of double digestions, KpnI-HindIII or SacI-EcoRI, was used, on the other hand the deletion was carried out by actions of exonuclease III, Mung bean nuclease and Klenow fragment. More specifically, the DNA fragment obtained by cleaving subcloned DNA with SacI and EcoRI for sequencing of +strand and the DNA fragment obtained by cleaving it with KpnI and HindIII for sequencing of −strand were used, treated by exonuclease III, then treated by Mung Bean Nuclease and Klenow fragment of DNA polymerase I to prepare a series of deletion mutant DNAs. The sequencing reaction of the deletion mutant clone was carried out by Thermo Sequenase (Amersham) and the nucleotide sequence was determined by ALFred (Pharmacia). The obtained data regarding the nucleotide sequence was analyzed by GENETYX-MAC/ATSQ v3.0 and GENETYX-MAC/ATSQ v8.0.

Subsequently, in order to determine the nucleotide sequence upstream (or downstream of transposase) of the cloned desulfurization enzyme genes derived from Paeni-bacillus sp. A11-2, a series of deletion DNAs was prepared. The digest obtained by digesting approx. 0.2 μg of DNA prepared from DSZA probe positive phage clone No. 2 with NotI and the digest obtained by treating pBluescript II KS(+) with NotI and dephosphorylated were litigated, and then *Escherichia coli* JM109 strain was transformed with the obtained hybrid DNA. After separating 20 single colonies, plasmid DNAs were extracted from the transformants and restriction-analyzed by NotI treamtment to obtain subclones pBS2N2 and pBS2N3 into which an approx. 3 kb of NotI fragment was inserted. The pBS2N2 and pBS2N3 are sub-clones wherein the 3 kb NotI fragment was inserted in the reverse direction to each other. Regarding pBS2N2 and pBS2N3, a series of deletion DNAs was prepared by using KpnI, HpaI, NruI, PstI and XhoI. The sequencing reaction of deletion clone was carried out by Thermo Sequenase (Amersham) and the nucleotide sequence was determined by ALFred (Phannacia). The obtained data regarding the nucleotide sequence was analysized by GENETYX-MAC/ATSQ v3.0 and GENETYX-MAC/ATSQ v8.0.

Analyzing ORF in the determined sequence indicated existence of three ORFs whose length was more than lkb in the center of 8.7 kb of the inserted DNA. These ORFs were named ORF1, ORF2 and ORF3 from 5' side. In addition to them, there existed one homologous ORF in the vicinity of each end of the inserted DNA. ORF1, ORF2 and ORF3 respectively encode 454, 353 and 414 amino acids. It was determined that the termination codon TGA of ORF1 and the initiation codon ATG of ORF2 are partially overlapped, and the overlapped sequence is 5'-ATGA-3' which has the same structure as the nucleotide sequence in the dsz operon of IGTS8. When analyzing the nucleotide sequence homology between these ORFs and dsz genes of IGTS8 strain, ORFs 1, 2 and 3 respectively showed approx. 64%, 54% and 48% of homology with dsz A, B and C of IGTS8 strain. In addition, when deducing the amino acid sequences of the proteins encoded by the nucleotide sequence of Paenibacillus sp. A11-2, the polypeptides encoded by ORFs 1, 2 and 3 respectively showed 65%, 54% and 52% of homology with DszA, DszB and DszC of IGTS8 strain.

Comparing the amino acid sequence of the protein encoded by ORF of Paemibacillus sp. A 11-2 strain with that encoded by the dsz sequence of Rhodococcus sp. IGTS8, characteristic differences were found in several points. First, regarding protein A encoded by ORF1 and DszA, their sequences at the amnino terminus and the carboxyl terminus are completely different, standing in sharp contrast to the internal amino acid sequences whose homology is relatively high. Second, protein A has longer amino and carboxyl termini. On the other hand, the amino acid sequences of protein B encoded by ORF2 and DszB are completely different from the relationship between protein A and DszA; the amino and carboxyl termini of DszB extend longer than both termini of protein B, and above all, homology is not found in the amino terminal sequence. Comparing the amino acid sequences of protein C encoded by ORF3 and DszC, then full lengths are almost the same, but the sequences of the amino terminal sides are completely different.

In approx. 8 kb DNA whose nucleotide sequence was determined, one ORF was found upstream of a series of sequences of ORF1, ORF2 and ORF3, and two ORFs were found downstream. The lengths of the upstream ORF and the most downstream ORF are both approx. 1 kb, they show a perfect homology, and the polypeptides encoded by the ORFs was determined to have approx. 30% homology at the amino acid level to the transposase in the insertion sequence IS1202. The ORF encoding this transposase was oriented in the reverse direction to the ORF for desulfurization gene. The fact that a series of ORFs encoding desulfurization activity was sandwiched by the insertion sequence-like sequences suggested the possibility that these DNA sequences form a sort of transposon. Moreover, it was also detected that approx. 0.6 kb ORF, which was found between the insertion sequence-like positioned at the most downstream and a series of ORFs encoding desulfurization activity, encoded the amino acid sequence which showed approx. 40% homology with carbonic anhydrase.

Example 4

Separation of Desulfurization-ability Deficient Strain Paenibacillus sp. M18 and Analysis of its Properties Paenibacillus sp. A 11-2 strain was treated with acridine orange so that the mutant strain M18 which lost the ability to decompose DBT was separated. First, A11-2 strain was cultured in 2×YT medium overnight at 50° C., and 0.1 ml of the obtained overnight-cultured broth was transferred into 5 ml of 2×YT medium containing 30 $\mu$g/ml of acridine orange, then it was cultured overnight at 50° C. The cells were collected by centrifugation and washed once with medium A. The washed cells were suspended in 0.1 ml of medium A, then transferred into 2ml of 2×XY medium and cultured for four hours at 50° C. The cultured broth was applied to a 2×YT agar medium and cultured overnight at 50° C. The generated colony was transferred into medium A whose sulfur source was only DBT, its ability to utilize DBT was detected and finally a desulfurization deficient strain (M18 strain) which cannot utilize DBT was obtained. The fact that the mutant strain M18 lost the activity of decomposing DBT was confirmned by culturing the said strain in a medium containing DBT and various methyl DBT derivatives and analyzing its growth. After collecting cells from M18 strain and its parent strain which were cultured in AYD medium overnight, those cells were washed with AY medium two times, then were suspended in AY medium. 5 ml of AY medium was contained in a screw capped test tube, on which 1 $\mu$l of n-tetradecane containing 50 ppm in sulfur concentrations of each organic sulfur compound was layered, then 100 $\mu$l of the cell suspension prepared by the above-stated method was added, and it was cultured for a day at 50° C. After the culture, 100 $\mu$l of 6N hydrochloric acid was added, was stirred, and was extracted with 1 ml of ethyl acetate. Finally gas chromatography and gas chromatography/mass spectrometry were carried out to the obtained ethyl acetate-n-tetradecane layer. As a result, it was determined that, for any of the detected organic sulfur compounds, M18 strain cannot use them as only sulfur sources and does not show a feature of decomposing them. In the case of a room-temperature desulfurizing strain Rhodococcus sp. IGTS8, DBT is decomposed over a path such as DBT→DBTO→DBTO2-→(2'-hydroxyphenyl) benzene-sulfinic acid→2-HBP+sulfite (Oldfield, C., Pogrebinsky, O., Simmonds, J., Olson, E. S. and Kulpa, C. F. Microbiology, 143:2961–2973, 1997). It is known that 2-(2'-hydroxyphenyl) benzenesulfinic acid provides DBT sultine when it forms a ring (Olson, E. S., Stanley, D. C. and Gallagher, J. R. Energy & Fuels 7:159–164, 1993). Further, it has been reported that, because of the enzyme activity of DszA, Rhodococcus sp. IGTS8 strain, in association with reductase, converts DBT sultone into 2-HBP and sulfite (Oldfield, C., Pogrebinsky, O., Simmonds, J., Olson, E. S. and Kulpa, C. F. Microbiology, 143:2961–2973, 1997). Using a medium containing the intermediate metabolite of this pathway as the only sulfur source, the availability and bioconversion of the sulfur source by M18 strain were studied. The result is that the strain could not use any of DBTO, DBTO2, DBT sultine and DBT sultone as the sulfur source, and conversion activity was not detected either. Taking this result into account, it is considered that M18 strain has lost a whole series of enzyme activity involved in the decomposition reaction pathway wherein DBT is decomposed into 2-HBT.

Example 5

Proof of the Desulfurization Activity of the Protein Encoded by ORF in Recombinant DNA In order to determine that a cloned DNA is the genetic entity which expresses desulfurization activity, that is, the activity of decomposing DBT, a recombinant plasmids were prepared such that a sequence containing a DNA fragment with all or part ORF1, 2 and 3 was positioned downstream of Ptac, a strong promoter acting in *Escherichia coli*, and then *Escherichia coli* JM109 strain was transformed, with each of the obtained recombinant plasmids. The detailed method for preparing various recombinant plasmids is described below. First, 8.7 kb EcoRI-HindIII fragment derived from Paenibacillus sp. A11-2 strain DNA was cloned into phagemid vector pBluescriptII KS(+) to obtain a recombinant DNA p4EH which was then double-digested with ClaI and SmaI thereby obtaining a ClaI-HindIII fragment. Similarly, pBluescript II KS(+) was cut with ClaI and HindIII to recover a larger fragment. This larger fragment was subsequently ligated to the obtained ClaI-HindIII fragment to prepare a recombinant DNA pB14. Second, pB14 was double-digested with XbaI and KpmI, and a DNA fragment containing the entire DNA derived from the cloned Paenibacillus sp. A11-2 strain was collected and ligated to the larger fragment which was obtained by double-digesting pHSG298 plasmid with XbaI and KpnI, thereby to prepare recombinant DNA pSKR6. This pSKR6 was double-digested with EcoRI and HindIII, and was inserted into EcoRI-HindIII site of expression vector pKK223-3 to prepare expression plasmid pSKR7. *Escherichia coli* JM109 strain was transformed with this pSKR7 to obtain transformant strain #121 (pSKR7). In this strain, there are approx. 50 bp between ATG sequence which seemingly corresponds to the initiation codon of ORF1 which is presumed to correspond to dszA on the most 5' side of dsz operon of IGTS8 strain and Shine-Dalgarno (SD) sequence disposed downstream of the expression promoter Ptac on pKK223-3. Experiments on the expression of genes from various *Escherichia coli* and foreign genes have indicated that the distance between the SD sequence and the ATG initiation codon has a very large influence over the translation efficiency of the gene (e.g. Horwich, A, Koop, A. H. and Eckhart, W. Mol. Cell. Biol. 2:88–92, 1982; Gheysen, D., Iserentant, D., Derom, C. and Fiers, W. Gene 17:55–63, 1982). So, in order to shorten the distance between the SD sequence and the ATG initiation codon, plasmid pSKR7 was cleaved at ClaI site immediately followed by ORF of dszA (5'-ATCGAT-3'; G being on the 3' side forms the sequence of the ATG initiation codon) and at EcoRI site, the generated cohesive terminus was treated with T4DNA polymerase to be blunt-ended, and a ring-closure was done again by ligation. By carrying out this treatment, the distance between the SD sequence and the ATG initiation codon was shortened to 11bp. Now, *Escherichia coli* JM109 was transformed with this recombinant plasmid, and the obtained transformant strain was named #361 strain.

6 ml of LB-Amp-DBT medium (containing 10 g of Bacto polypeptone, 5 g of Bacto yeast extract, 10 g of NaCl, 50 mg of Ampicillin, 100 mg of DBT in 1L) was contained in each of screw capped test tubes whose diameter is 18 mm, 1% of #361 strain suspension cultured overnight on the same medium was inoculated, then it was cultured at 37° C. Every two hours after the beginning of the culture, two test tubes were taken out, and the entire cultured broth of each test tube was extracted with 1.2 ml of ethyl acetate and was analyzed and quantified by gas chromatography. Also the turbidity of the cultured broth was measured by spectrophotometer every two hours after the beginning of the culture. Consequently, it was confirmed that DBT was decreasing while cultured for 4–8 hours and that 2-HBP being the metabolite of DBT was generated in the medium FIG. 3 shows the decrease of DBT and the formation of DBT metabolite in this medium, wherein each numerical value represents the average analytical value obtained from the two test tubes. Since DBT remarkably decreased for 4–6 hours after the beginning of the culture, we intended to analyze the activity of the cell free extraction system using the cells cultured for 6 and 8 hours.

The preparation of cell free extracts was carried out as follows. To 100 ml of LB medium (LB-Amp medium) containing 50 mg/ml of Ampicillin, 1 ml of overnight-cultured broth of #361 strain prepared from the same broth was inoculated, and then it was cultured for 6 or 8 hours at 37° C. After collecting and washing the cultured cells, they were suspended in TH buffer (50 mM Tris-HCl, 1mM PMSF, 10% glycerol, pH7.0) so that $OD_{660}$ becomes 25. The cell suspension was treated by an ultraoscillator for 10 minutes two times, and the obtained cell suspension was centrifuged at 11,000 rpm for 60 minutes to prepare cell free extracts. The reaction of the cell free extracts system was carried out as follows. To 0.7 ml of the prepared cell free extracts, 0.3 ml of cell free extracts prepared from the mutant strain M18 of Paenibacillus sp. A11-2 which does not have desulfurization activity in the same manner as stated above, 3 mM of NADH, 10$\mu$M of FMN and approx. 50 ppm of DBT were added, then the reaction was carried out by rotary-shaking for four hours at 37° C. or 50° C. The obtained reaction mixture was extracted in accordance with standard techniques and DBT and DBT metabolite were analyzed by gas chromatography. In addition, using a portion of the cell suspension prepared so that $OD_{660}$ was adjusted to 25, a resting cell reaction was also carried out. Regarding the resting cell reaction, approx. 50 ppm as the final concentration of DBT was added to 1 ml of the cell suspension followed by the reaction for five hours at 37° C. The obtained reaction mixture was analyzed by gas chromatography in accordance with standard techniques.

FIG. 4 shows the result of the reactions carried out at 37° C. and 50° C. adopting DBT as a substrate using the cell free extracts obtained from the cells of #361 strain cultured for 6 and 8 hours. Regarding the cells cultured for 8 hours, the activity of decomposing DBT in a resting cell reaction system which was examined concurrently is also disclosed. As shown in FIG. 4, it was observed that in the reactions at 37° C. of both the cell free extracts system and the resting cell system, the reaction of generating 2-HBP using DBT as a substrate progressed, and it was determined that both of them have desulfurization activity. In addition, regarding the cell free extracts system, the formation of 2-HBP from DBT at 50° C., that is to say, desulfulrization activity was also clearly confirmed. From this result, it was proved that the DNA fragment derived from the cloned Paenibacillus sp. A11-2 strain DNA actually carried on the activity of decomposing DBT at high temperature. On the other hand, when the cell free extracts prepared by the same method as for #361 strain was used, applying the parent strain JM109 and the JM109 containing only vector pBluescript II KS(+), no 2-HBP was generated at all. Moreover, with this cell free extracts of #361 strain, even at 50° C., the conversion of benzothiophene into the desulfurized product o-hydroxystyrene was observed. This shows that the activity of decomposing benzothiophene at high temperature is also carried by the DNA of A 11-2 strain introduced into *Escherichia coli*.

It was presumed that the DNA fragment carrying desulfurization activity derived from Paenibacillus sp. A 11-2 strain contains 3 ORFs and that, considering its nucleotide sequence, it has the same gene structure as desulfurization genes cloned from Rhodococcus sp. IGTS8 strain and Rhodococcus erythropolis KA2-5-1 strain. Hence, various deletion DNA fragments were prepared using recombinant plasmids of #361 strain, and the relation between the deletion DNA fragments and the activity of DBT decomposition system of each ORF was analyzed. The linear DNA obtained by cleaving #121 plasmid at BsrGI site situated 12bp upstream of ATG initiation codon of ORF2 and at EcoRI site downstream of SD sequence was treated with T4DNA polymerase then T4DNA ligase to prepare a recyclized recombinant plasrmid. After transforming *Escherichia coli* JM109 with this plasmid, the obtained transformant strain containing ORF2 and ORF3 on the cloned DNA from Paenibacillus sp. A 11-2 strain was named #233. Following the same method, the transformant strain #234 containing only ORF3 was prepared by using SacII site immediately followed by ORF3 and EcoRI site situated downstream of the SD sequence, and the transformant strain #391 containing only ORF2 was prepared by using BsrGl site and PstI site. Furthermnore, the transformant strain #401 containing ORF1 and ORF2 was prepared by using PstI site situated inside of ORF3 of the transformant strain #361 and PstI site derived from a vector. Each of these transformant strains having deletion DNAs was cultured in LB-Amp medium overnight, and 50 µl of the cultured broth was inoculated upon 5 ml of LB-Amp medium, into which DBT, DBTO2 or DBT-sultine were added, to obtain 50 mg/l as the final concentration, then it was cultured overnight at 37° C. The obtained overnight-cultured broth was extracted with 1 ml of ethyl acetate, and the extract was analyzed/quantified by gas chromatography. The results are shown in Table 3.

421, but was not so in #233, #234 and #391, it is known that ORF1 encodes oxygenase having an activity of generating DBT-sultine from DBTO2. It was observed that a small amount of 2-HBP was generated from DBT-sultine even in the control test wherein only LB-Amp medium without cells but containing DBT-sultine as the only sulfur source was shaken in the same conditions as in the recombinant clones. The present inventors have carried out various control tests and confirmed that this is a spontaneous reaction occurred without enzymes or cells. Consequently, it is necessary to adjust the above result by subtracting the amount of 2-HBP more or less equal to that observed in "Blank" from each of the amounts determined using each transformant strain. As a result of such an adjustment, 2-HBP was generated from DBT-sultine in #361, #233, #391 and #401, but it was not so in #234 and #421. For this reason, it is known that ORF2 encodes desulfinase having an activity of generating 2-HBP from DBT-sultine.

Example 6

Culture of Paenibacillus sp. A 11-2 strain

A medium (150 ml) having the same composition as medium A used in Example 1 was contained in a 500 ml-capacity of sealed screw capped conical flask with a baffle, 50 mg/l of DBT and cultured broth of A 11-2 strain were added thereto, and it was rotary-shaken at 120 rpm at 50° C. After culturing it overnight, the cultured broth was centrifuged at 5,000 rpm for 10 minutes at 4° C. to collect cells.

TABLE 3

| Sample | Contained ORF | substrate | Yield (µM) | | | | | |
|---|---|---|---|---|---|---|---|---|
| | | | DBT | DBTO | DBTO2 | Sultine | 2-HBP | Total |
| Blank | | DBT | 136 | 0 | 0 | 0 | 0 | 136 |
| | | DBTO2 | 0 | 0 | 117 | 0 | 0 | 117 |
| | | Sultine | 0 | 0 | 0 | 54 | 9 | 63 |
| vector | | DBT | 130 | 0 | 0 | 0 | 0 | 130 |
| | | DBTO2 | 0 | 0 | 117 | 0 | 0 | 147 |
| | | Sultine | 0 | 0 | 0 | 61 | 7 | 69 |
| #361 | ORF1 | DBT | 72 | 0 | 0 | 0 | 48 | 119 |
| | ORF2 | DBTO2 | 0 | 0 | 78 | 0 | 34 | 112 |
| | ORF3 | Sultine | 0 | 0 | 0 | 51 | 27 | 78 |
| #233 | ORF2 | DBT | 101 | 0 | 24 | 0 | 0 | 125 |
| | ORF3 | DBTO2 | 0 | 0 | 114 | 0 | 0 | 114 |
| | | Sultine | 0 | 0 | 0 | 55 | 18 | 73 |
| #234 | ORF3 | DBT | 104 | 0 | 21 | 0 | 0 | 125 |
| | | DBTO2 | 0 | 0 | 116 | 0 | 0 | 116 |
| | | Sultine | 0 | 0 | 0 | 60 | 9 | 69 |
| #391 | ORF2 | DBT | 126 | 0 | 0 | 0 | 0 | 126 |
| | | DBTO2 | 0 | 0 | 117 | 0 | 0 | 117 |
| | | Sultine | 0 | 0 | 0 | 52 | 20 | 72 |
| #401 | ORF1 | DBT | 127 | 0 | 0 | 0 | 0 | 127 |
| | ORF2 | DBTO2 | 0 | 0 | 2 | 0 | 99 | 101 |
| | | Sultine | 0 | 0 | 0 | 35 | 44 | 79 |
| #421 | ORF1 | DBT | 126 | 0 | 0 | 0 | 0 | 128 |
| | | DBTO2 | 0 | 0 | 0 | 58 | 7 | 65 |
| | | Sultine | 0 | 0 | 0 | 56 | 7 | 63 |

The amount of the added substrate; DBT: 136 µM, DBTO: 125 µM, DBTO2: 118 µM, Sultine: 107 µM From the data regarding the formation of DBT metabolite by each transformant strain shown in the table, it is known that 3 ORFs in the DNA cloned from Paenibacillus sp A11-2 strain were associated with DBT decomposition. First, due to the fact that DBTO2 was generated from DBT in #361, #233 and #234 but it was not so in #391, #401 and #421, it is clear that ORF3 encodes oxygenase having an activity of generating DBTO2 from DBT. Second, due to the fact that DBT-sultine was generated from DBTO2 in #361, #401 and Example 7

(1) Purification of Protein A

The cells from Example 6 (wet weight 30 g) were suspended in buffer A (20 mM Tris-HCl, pH7.5, 10% glycerol, 1 mM dithiothreitol, 1 mM phenylmethanesulfonylfluoride) and were sonicated by an ultraoscillator (Branson, model 450) for 15 minutes at 4° C. three times. After centrifugation at 5,000×g for 10 minutes to remove intact cells, the supernatant was centrifuged at 100,000 ×g for 60 minutes. The obtained supernatant was passed through a filter whose pore size is 0.22 µm and was applied to an anion exchange column (Phamacia, HiLoad Q 26/10) equilibrated with buffer B (20 mM Tris-HCl, pH7.5, 10% glycerol, 1 mM dithiothreitol). After washing with buffer B, elution was carried out with linear gradient from buffer B to buffer B containing 0.5M sodium chloride. Active fractions (0.35–0.4M sodium chloride) were collected and concentrated by ultrafiltration. After diluting with buffer A, ammonium sulfate was added to prepare 30% saturated solution. This solution was applied to a hydrophobic chromatography column (Pharmacia, HiLoad Phenyl Sepharose HP) which was equilibrated with 30% saturated buffer containing ammonium sulfate. Active fractions were collected, concentrated by ultrafiltration (Millipore, Ultrafree15, molecular weight 10,000 cut-off), desalinated by a desalting column (Pharmacia, PD-10), and then were applied to an anion exchange column (Bio/Rad, Proteinpack DEAE) equilibrated with buffer B. Active fractions were collected, concentrated by ultrafiltration, desalinated by a desalting column, and then were applied to a hydroxyapatite column (Bio/Rad, BioGel HPHT) equilibrated with buffer C (10 mM potassium phosphate, pH7.1, 10% glycerol, 1mM dithiothreitol). After washing with buffer C, elution was carried out with linear gradient from buffer C to buffer C contain 0.2M potassium phosphate. As a result, it was confirmed that the active fractions were electrophoretically uniform.

(2) Measurement of Enzyme Activity

To the buffer containing 3 mM of NADH and 10 μM of FMN (50 mM Tris-HCl, pH7.0) the enzyme solution was added, and further 0.4 ml of cell free extracts of M18 strain, which does not have an ability to utilize DBT, obtained by curing treatment for A11-2 was also added. After a preincubation for two minutes at 50° C., DBTO2 solution (dimethylformamide solution)was added to obtain 50 mg/l as the final concentration (the total amount of solution is 1ml). At the end of the reaction, 10 μl of 6N hydrochloric acid and 0.4 ml of ethyl acetate were added, fully mixed, then centrifuged at 12,000 rpm for 3 minutes. Then, analysis by gas chromatography was carried out to the obtained upper layer (ethyl acetate layer). The specific activity is represented such that 1 denotes activity decomposing 1 nmol of DBT-sulfone per 1 mg of protein per a minute.

Enzyme activities in each step of purification are shown in Table 4 and the activities with various pHs and temperatures are shown in FIGS. 6 and 7.

TABLE 4

|  | Protein (mg) | Specific acitivity (U/mg) | Total Activity (U) |
| --- | --- | --- | --- |
| Crude extract | 1488 | 2.1 | 3125 |
| HiLoad Q 26/10 | 144 | 13.3 | 1915 |
| Hiload Phenyl Sepharose HP | 40 | 31.3 | 1252 |
| Protein Pack DEAE | 5 | 68.3 | 342 |
| BioGel HPHT | 1 | 100 | 100 |

Example 8

(1) Purification of Protein B

The cells from Example 6 (wet weight 13 g) were suspended in buffer A (20 mM Tris-HCl, pH7.5, 10% glycerol, 1 mM dithiothreitol, 1 mM phenylmethanesulfonylfluoride) and were sonicated by an ultraoscillator (Branson, model 450) for 15 minutes at 4° C., three times. After centrifugation at 5,000×g for 10 minutes to remove intact cells, the supernatant was centrifuged at 100,000×g for 60 minutes. The obtained supernatant was passed through a filter (Millipore Millex GV, pore size 0.22 μm) and was applied to an anion exchange column (Pharmacia, HiLoad Q 26/10) equilibrated with buffer B (20 mM Tris-HCl, pH7.5, 10% glycerol, 1 mM dithiothreitol). After washing with buffer B, elution was carried out with linear gradient from buffer B to buffer B containing 0.5M sodium chloride. Active fractions (0.15–0.2M sodium chloride) were collected and concentrated by ultrafiltration (Millipore, Ultrafree 15, molecular weight 5,000 cut-off). After diluting with buffer A, ammonium sulfate was added to prepare 30% saturation. This solution was applied to a hydrophobic chromatography column (Pharmacia, HiLoad Phenyl Sepharose HP) which was equilibrated with 30% saturated buffer containing ammonium sulfate. Active fractions were collected, concentrated by ultrafiltration, desalted by a desalting column (Pharmacia, PD-10), and then were applied to an anion exchange column (Bio/Rad, Bioscale DEAE) equilibrated with buffer B. Active fractions were collected, concentrated, desalted, and then were applied to a hydroxyapatite column (Bio/Rad, BioGel HPHT) equilibrated with buffer C (10 mM potassium phosphate, pH7.1, 10% glycerol, 1 mM dithiothreitol). After washing with buffer C, elution was carried out with linear gradient from buffer C to buffer C containing 0.2M potassium phosphate and then it was applied to an anion exchange column (Pharmacia, Mono Q HR5/5) equilibrated with buffer B. After washing with buffer B, elution was carried out with linear gradient from buffer B to buffer B containing 0.5M sodium chloride. As a result, it was confirmed that the active fractions were electrophoretically uniform.

(2) Measurement of Enzyme Activity

Enzyme solution was added to buffer D (50 mM Tris-HCl, pH7.0), and after preincubation for two minutes at 50° C., sultine (in N, N-dimethylformamide) was added to obtain 50 mg/l as the final concentration (total volume 1 ml). At the end of the reaction, 10 μl of 6N hydrochloric acid and 0.4 ml of ethyl acetate were added, fully mixed, then analysis by gas chromatography was carried out to the obtained upper layer (ethyl acetate layer). The measurement of activity was carried out by quantifying 2-HBP produced. The specific activity is represented such that 1 unit denotes activity producing 1 nmol of 2-HBP per 1 mg of protein per minute. To prevent the influence of 2-HBP inhibiting the activity, sodium 2-phenylbenzensulfinate was used as a substrate, and the activity was measured by quantifying the generated biphenyl.

Enzyme activities in each step of purification are shown in Table 5 and the activities at various pHs and temperatures are shown in FIGS. 8 and 9.

TABLE 5

|  | Protein (mg) | Specific activity (U/mg) | Total Activity (U) |
| --- | --- | --- | --- |
| Crude extract | 504 | 2.2 | 1109 |
| HiLoad Q 26/10 | 120 | 10 | 1200 |
| Hiload Phenyl Sepharose HP | 18 | 31 | 558 |
| Protein Pack DEAE | 7 | 16 | 112 |
| BioGel HPHT | 1 | 85 | 85 |
| Mono Q | 0.2 | 139 | 28 |

All publications, patents and patent applications cited herein are incorporated herein by reference in their entirety.

Advantage of the Invention

The present invention provides novel genes and enzymes associated with desulfurization. By using these genes and enzymes, sulfur existing in fossil fuel can be easily removed.

What is claimed is:

1. An isolated nucleic acid comprising a sequence that encodes:
a protein comprising an amino acid sequence of SEQ ID NO: 6.

2. A vector comprising:
a sequence that encodes a polypeptide with an amino acid sequence of SEQ ID NO: 6.

3. A transformed cell comprising:
a vector comprising a sequence that encodes a polypeptide with an amino acid sequence of SEQ ID NO: 6.

4. A transformed cell comprising:
a first vector comprising a sequence that encodes a first polypeptide with an amino acid sequence of SEQ ID NO: 6 for converting a first compound into a second compound;
a second vector comprising a sequence that encodes a second polypeptide for converting the second compound into a third compound; and
a third vector comprising a sequence that encodes a third polypeptide for converting the third compound into a fourth compound.

5. The transformed cell according to claim 4 wherein the first, second, and third compounds are sulfur compounds; and the fourth compound is a desulfurized compound.

6. The transformed cell according to claim 4 wherein the first compound comprises dibenzothiophene; the second compound comprises dibenzothiophenesulfone; the third compound comprises 2-(2'-hydroxyphenyl) benzenesulfinic acid; and the fourth compound comprises 2-hydroxylbiphenyl.

7. A transformed cell according to claim 4 wherein the; the second polypeptide comprises an amino acid sequence of SEQ ID NO: 2; and third polypeptide comprises an amino acid sequence of SEQ ID NO: 4.

8. The transformed cell according to claim 4, wherein the second polypeptide has the following characteristics:

(1) Function: it converts dibenzothiophenesulfone into 2-(2'-hydroxyphenyl) benzenesulfinic acid
(2) Optimum pH: 5.5, stable pH: 5–10;
(3) Optimum temperature: 45° C.
(4) Molecular weight: 120,000 (as determined by gel filtration);
(5) Inhibition of activity: it is inhibited by chelating agents or SH inhibitors, but no by 2-HBP or sulfate; and
(6) Requirement for coenzyme: NADH and FMN are required; NADPH can be substituted for NADH, but FAD cannot be substituted for FMN.

9. The transformed cell according to claim 4, wherein the third polypeptide has the following characteristics:

(1) Function: 2-(2'-hydroxyphenyl) benzenesulfinic acid into 2-hydroxylbiphenyl;
(2) Optimum pH: 8, stable pH: 5.5–9.5;
(3) Optimum temperature: 55° C.;
(4) Molecular weight: 31,000 (as determined by gel filtration);
(5) Inhibition of activity: it is inhibited by chelating agents and SH inhibitors, but not by 2-HBP or sulfate; and
(6) Requirement for coenzyme; coenzyme is not required.

10. A process of producing polypeptides comprising:
expressing in the transformed cell of claim 4, the first polypeptide to convert the first compound into the second compound;
expressing in the transformed cell the second polypeptide to convert the second compound into the third compound; and
expressing in the transformed cell the third polypeptide to convert the third compound into the fourth compound.

11. A process of producing polypeptides comprising:
expressing in the transformed cell of claim 4, the first polypeptide to convert dibenzothiophene into dibenzothiophenesulfone;

expressing in the transformed cell the second polypeptide to convert dibenzothiophenesulfone into 2-(2'-hydroxyphenyl) benzenesulfinic acid; and expressing in the transformed cell the third polypeptide to convert 2-(2'-hydroxyphenyl) benzenesulfinic acid into 2-hydroxylbiphenyl.

12. A process of producing a transformed cell comprising:

providing into a cell a first vector comprising a sequence that encodes a first polypeptide with an amino acid sequence of SEQ ID NO: 6 to convert a first compound into a second compound;

providing into the cell a second vector comprising a sequence that encodes a second polypeptide to convert the second compound into a third compound; and providing into the cell a third vector comprising a sequence that encodes a third polypeptide to convert the third compound into a fourth compound.

13. The process according to claim 12 wherein the first compound comprises dibenzothiophene; the second compound comprises dibenzothiophenesulfone; the third compound comprises 2-(2'-hydroxyphenyl) benzemesulfinic acid; and the fourth compound comprises 2-hydroxylbiphenyl.

14. A process of producing a transformed cell according to claim 12 wherein:

the second polypeptide comprises an amino acid sequence of SEQ ID NO: 2; and the third polypeptide comprises an amino acid sequence of SEQ ID NO: 4.

15. The process according to claim 12, wherein the second polypeptide has the following characteristics:

(1) Function: it converts dibenzothiophenesulfone into 2-(2'-hydroxyphenyl) benzenesulfinic acid (2) Optimum pH: 5.5, stable pH: 5–10;

(3) Optimum temperature: 45° C.

(4) Molecular weight: 120,000 (as determined by gel filtration);

(5) Inhibition of activity: it is inhibited by chelating agents or SH inhibitors, but no by 2-HBP or sulfate; and (6) Requirement for coenzyme: NADH and FMN are required; NADPH can be substituted for NADH, but FAD cannot be substituted for FMN.

16. The process according to claim 12, wherein the third polypeptide has the following characteristics:

(1) Function: 2-(2'-hydroxyphenyl) benzenesulfinic acid into 2-hydroxylbiphenyl;

(2) Optimum pH: 8, stable pH: 5.5–9.5;

(3) Optimum temperature: 55° C.;

(4) Molecular weight: 31,000 (as determined by gel filtration);

(5) Inhibition of activity: it is inhibited by chelating agents and SH inhibitors, but not by 2-HBP or sulfate; and (6) Requirement for coenzyme; coenzyme is not required.

17. The process according to claim 12 wherein the first, second, and third compounds are sulfuir compounds; and the fourth compound is a desulfurized compound.

* * * * *